US008309059B2

(12) United States Patent
Corona et al.

(10) Patent No.: US 8,309,059 B2
(45) Date of Patent: Nov. 13, 2012

(54) REACTIVE CYANINE COMPOUNDS

(75) Inventors: Cesear Corona, Paso Robles, CA (US); Dieter Klaubert, Arroyo Grande, CA (US); Mark McDougall, Arroyo Grande, CA (US)

(73) Assignee: Promega Corporation, Madison, WI (US)

( * ) Notice: Subject to any disclaimer, the term of this patent is extended or adjusted under 35 U.S.C. 154(b) by 273 days.

(21) Appl. No.: 12/872,467

(22) Filed: Aug. 31, 2010

(65) Prior Publication Data

US 2011/0053162 A1    Mar. 3, 2011

Related U.S. Application Data

(60) Provisional application No. 61/238,459, filed on Aug. 31, 2009.

(51) Int. Cl.
*A61B 5/00* (2006.01)
*A61B 8/00* (2006.01)
*A61B 10/00* (2006.01)
*C07D 209/02* (2006.01)

(52) U.S. Cl. ......................................... 424/9.6; 548/455
(58) Field of Classification Search .................. 424/9.6; 548/455
See application file for complete search history.

(56) References Cited

U.S. PATENT DOCUMENTS

| | | | |
|---|---|---|---|
| 2,398,999 A | 4/1946 | Brooker et al. |
| 4,711,955 A | 12/1987 | Ward et al. |
| 4,981,977 A | 1/1991 | Southwick et al. |
| 4,997,928 A | 3/1991 | Hobbs, Jr. |
| 5,047,519 A | 9/1991 | Hobbs, Jr. et al. |
| 5,049,673 A | 9/1991 | Tsien et al. |
| 5,171,534 A | 12/1992 | Smith et al. |
| 5,268,486 A | 12/1993 | Waggoner et al. |
| 5,321,130 A | 6/1994 | Yue et al. |
| 5,332,666 A | 7/1994 | Prober et al. |
| 5,405,975 A | 4/1995 | Kuhn et al. |
| 5,453,517 A | 9/1995 | Kuhn et al. |
| 5,486,616 A | 1/1996 | Waggoner et al. |
| 5,516,911 A | 5/1996 | London et al. |
| 5,539,082 A | 7/1996 | Nielsen et al. |
| 5,567,588 A | 10/1996 | Gold et al. |
| 5,569,587 A | 10/1996 | Waggoner |
| 5,569,766 A | 10/1996 | Waggoner et al. |
| 5,580,990 A | 12/1996 | Van Den et al. |
| 5,627,027 A | 5/1997 | Waggoner |
| 5,648,270 A | 7/1997 | Kuhn et al. |
| 5,658,751 A | 8/1997 | Yue et al. |
| 5,659,025 A | 8/1997 | Engels et al. |
| 5,668,268 A | 9/1997 | Tang et al. |
| 5,679,785 A | 10/1997 | Engels et al. |
| 5,684,142 A | 11/1997 | Mishra et al. |
| 5,714,327 A | 2/1998 | Houthoff et al. |
| 5,808,044 A | 9/1998 | Brush et al. |
| 5,877,310 A | 3/1999 | Reddington et al. |
| 5,985,566 A | 11/1999 | Houthoff et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,133,445 A | 10/2000 | Waggoner et al. |
| 6,150,510 A | 11/2000 | Seela et al. |
| 6,492,102 B1 | 12/2002 | Kagawa et al. |
| 6,593,148 B1 | 7/2003 | Narayanan |
| 6,974,873 B2 | 12/2005 | Leung et al. |
| 6,977,305 B2 | 12/2005 | Leung et al. |
| 6,995,274 B2 | 2/2006 | Lugade et al. |
| 7,008,771 B1 | 3/2006 | Schumm et al. |
| 2002/0106593 A1 | 8/2002 | Kagawa et al. |
| 2006/0239922 A1 | 10/2006 | Cooper et al. |

FOREIGN PATENT DOCUMENTS

| | | |
|---|---|---|
| EP | 1065250 | 1/2001 |
| WO | WO 94/05688 | 3/1994 |
| WO | WO 97/40104 | 10/1997 |
| WO | WO 99/51702 | 10/1999 |
| WO | WO 01/21624 | 3/2001 |
| WO | WO 2010/107816 | 9/2010 |

OTHER PUBLICATIONS

Anderson, G.W. et al., "The use of esters of N-hydroxysuccinimide in peptide synthesis," J. Amer. Chem. Soc. (1964) 86:1839-1842.
Atamna, H. et al., "A method for detecting abasic sites in living cells: age-dependent changes in base excision repair," Proc. Natl. Acad. Sci. USA (2000) 97(2):686-691.
Brinkley, M., "A brief survey of methods for preparing protein conjugates with dyes, haptens, and cross-linking reagents," Bioconjugate Chem. (1992) 3:2-13.
Gruber, H.J. et al., "Anomalous fluorescence enhnacement of Cy3 and Cy3.5 versus anomalous fluorescence loss of Cy5 and Cy7 upon covalent linking to IgG and noncovalent binding to avidin," Bioconjugate Chem. (2000) 11:696-704.
Haugland, R. "Fluorophores and their amine-reactive derivatives," Chapter 1 of Molecular Probes. Handbook of Fluorescent Probes and Research Chemicals (1996) p. 7-46.
Haugland, R. "Thiol-reactive probes," Chapter 2 of Molecular Probes. Handbook of Fluorescent Probes and Research Chemicals (1996) p. 47-62.
Haugland, R. "Reagents for modifying groups other than thiols or amines," Chapter 3 of Molecular Probes. Handbook of Fluorescent Probes and Research Chemicals (1996) p. 63-80.

(Continued)

*Primary Examiner* — Michael G Hartley
*Assistant Examiner* — Leah Schlientz
(74) *Attorney, Agent, or Firm* — Michael Best & Friedrich LLP

(57) ABSTRACT

The invention provides compounds and compositions of Formulas I-VII, and methods of using the compounds. The compounds can be used to prepare dye conjugates that are uniformly and substantially more fluorescent on proteins, nucleic acids or other biopolymers, than conjugates labeled with structurally similar known carbocyanine dyes. In addition to having more intense fluorescence emission than structurally similar dyes at virtually identical wavelengths, and decreased artifacts in their absorption spectra upon conjugation to biopolymers, the compounds can have greater photostability and/or higher absorbance (extinction coefficients) at the wavelength(s) of peak absorbance than such structurally similar dyes.

21 Claims, 5 Drawing Sheets

OTHER PUBLICATIONS

Huffman, M.A. et la., "Lithium alkoxides of cinchona alkaloids as chiral controllers for enantioselective acetylide addition to cyclic N-acyl ketimines," J. Org. Chem. (1995) 60:1590-1594.

McMahan, S.A. et al., "Single-step synthesis and characterization of biotinylated nitrilotriacetic acid, a unique reagent for the detection of histidine-tagged proteins immobilized on nitrocellulose," Anal. Biochem. (1996) 236:101-106.

Mishra, A. et al., "Cyanines during the 1990s: a review," Chem. Rev. (2000) 100:1973-2011.

Mujumdar, R.B. et al., "Cyanine dye labeling reagents: sulfoindocyanine succinimidyl esters," Bioconjugate Chem. (1993) 4(2):105-111.

Ogura, H. et al., "Beta-elimination of beta-hydroxyamino acids with disuccinimido carbonate," Tetrahedron Lett. (1981) 22(48):4817-4818.

Ozmen, B. et al., "Infrared fluorescence sensing of submicromolar calcium: pushing the limits of photoinduced electron transfer," Tetrahedron Lett. (2000) 41:9185-9188.

Raju, B. et la., "A fluorescent indicator for measuring cytosolic free magnesium," Am. J. Physiol. (1989) 256:C540-548.

Schumm, J.W. et al., "Development of nonisotopic multiplex amplification sets for analysis of polymorphic STR loci," Fourth International Symposium on Human Identification (1993) 177-187.

Sheehan, J.C. et al., "Total synthesis of a monocyclic peptide lactone antibiotic, etamycin," J. Am. Chem. Soc. (1973) 95:875-879.

Tucker, T.J. et al., "Synthesis of a series of 4-(arylethynyl)-6-chloro-4-cyclopropyl-3,4-dihydroquinazolin-2(1H)-ones as novel non-nucleoside HIV-1 reverse transcriptase inhibitors," J. Med. Chem. (1994) 37:2437-2444.

Tyagi, S. et al., "Multicolor molecular beacons for allele discrimination," Nature Biotech. (1998) 16:49-53.

Ushenko, N.K., "Cyanine dyes," Ukrainskii Khimicheskii Zhurnal (1955) 21:744-749.

Van Wijngaarden, I. et al., "Development of high-affinity 5-HT3 receptor antagonists. Structure-affinity relationships of novel 1,7-annelated indole derivatives," J. Med. Chem. (1993) 36:3693-3699.

Whittung, P. et al., "DNA-like double helix formed by peptide nucleic acid," Nature (1994) 368:561-563.

Zhou, W. et al., "New bioluminogenic substrates for monoamine oxidase assays," J. Am. Chem. Soc. (2006) 128(10):3122-3123.

International Search Report and Written Opinion for Application No. PCT/US2010/047274 dated Feb. 14, 2011 (10 pages).

Labeled untransfected CHO cells:

Labeled U2OS cells stably expressing HaloTag-NLS:

Labeled U2OS cells stably expressing HaloTag-ECS:

REACTIVE CYANINE COMPOUNDS

CROSS-REFERENCE TO RELATED APPLICATIONS

This application claims the benefit of U.S. Provisional Application Ser. No. 61/238,459, filed Aug. 31, 2009, which is incorporated by reference herein.

BACKGROUND

Fluorescent compounds can be covalently or noncovalently attached to other materials to impart color and fluorescence. Bright fluorescent dyes permit detection or location of the attached materials with great sensitivity. Certain carbocyanine dyes have demonstrated utility as labeling reagents for a variety of biological applications, e.g., U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; and 6,133,445; WO 97/40104, WO 99/51702, WO 01/21624, and EP 1 065 250 A1; and Ozmen et al., *Tetrahedron Letters*, 41:9185 (2000). Nevertheless, many carbocyanine dyes are known to share certain disadvantages, e.g., severe quenching of the fluorescence of carbocyanine dyes in biopolymer conjugates, and quenching of Cy5 and Cy7 dye variants on conjugates, as discussed in Gruber et al., *Bioconjugate Chem.*, 11:696 (2000), and in EP 1 065 250 A1. In addition, certain desired sulfoalkyl derivatives of the reactive carbocyanine dyes are difficult to prepare, such as Cy3 and Cy5 variants (see Waggoner et al., *Bioconjugate Chem.*, 4:105 (1993)). Cyanine dyes also have a very strong tendency to self-associate (i.e., stack), which can significantly reduce the fluorescence quantum yields (Mishra et al., *Chem. Rev.*, 100:1973 (2000)). Accordingly, new labeling reagents are needed to aid research in the field of biotechnology.

SUMMARY OF THE INVENTION

The invention provides a compound of Formula I:

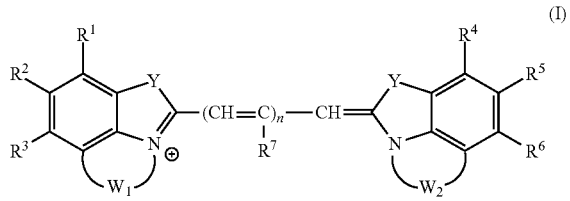

(I)

or Formula II:

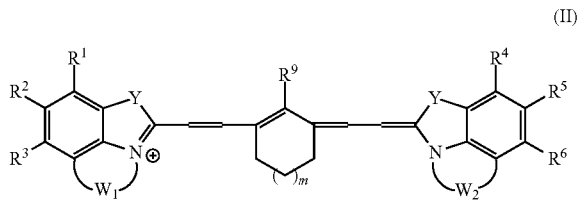

(II)

wherein $R^1$, $R^2$, $R^3$, $R^4$, $R^5$, and $R^6$ are each independently H, alkyl, cycloalkyl, aryl, (aryl)alkyl, heteroaryl, amino, hydroxy, halo, sulfo, or $-L-R^x$; or two adjacent groups of $R^1$, $R^2$, $R^3$, $R^4$, $R^5$, or $R^6$ taken together with the atoms to which they are attached form a fused benzo ring that is optionally substituted with 1, 2, 3, or 4 alkyl, cycloalkyl, aryl, (aryl)alkyl, heteroaryl, amino, hydroxy, halo, sulfo, or $-L-R^x$ groups;

each $W_1$ and $W_2$ taken together with the atoms to which it is attached is independently a 5-, 6-, 7-, or 8-membered heterocyclic ring, wherein the ring optionally includes a second heteroatom selected from O, S, or N, wherein the N, if present, is substituted by H, alkyl, (aryl)alkyl, or $-L-R^x$, and wherein at least one carbon atom of $W_1$ or $W_2$ is optionally substituted by $R^7$;

each Y is independently $CR^7R^7$, S, O, $CF_2$, or $NR^7$;

each $R^7$ is independently H, $(C_1-C_8)$alkyl, aryl, (aryl)alkyl, oxo, or $-L-R^x$;

each L is independently a direct bond or a linker, wherein the linker is a divalent radical of the formula -A-B-Z- wherein A is a direct bond or a $(C_1-C_{12})$alkyl chain optionally comprising one or more unsaturations, optionally substituted by one or more oxo groups, and optionally interrupted by one or more O atoms; B is a direct bond or a —NHC(=O)—, —C(=O)NH—, —OC(=O)—, —C(=O)O—, —O—, or —N($R^8$)— group; and Z is a direct bond or a $(C_1-C_{20})$alkyl chain optionally comprising one or more unsaturations, optionally substituted by one or more oxo groups, and optionally interrupted by one or more O atoms;

each $R^8$ is independently H, $(C_1-C_6)$alkyl, or a nitrogen protecting group;

$R^9$ is $-L-R^x$, —O-Ph-$R^x$, —O-Ph-L-$R^x$;

each $R^x$ is independently an activated ester of a carboxylic acid, a maleimide, an amine, an alcohol, a sulfonyl halide, a mercaptan, a boronate, a phosphoramidite, an isocyanate, a haloacetamide, an aldehyde, an azide, an acyl nitrile, a photoactivatable group, a 4-cyanobenzothiazole, a $(C_1-C_8)$alkylhalide, a carboxylic acid, or a sulfo group;

provided that at least one $-L-R^x$ group is present and provided that at least one $R^x$ is not a sulfo group;

wherein any alkyl, cycloalkyl, aryl, (aryl)alkyl, or heteroaryl is optionally substituted with one, two, or three halo, hydroxy, or sulfo groups;

m is 0 or 1; n is 0, 1, or 2; and an organic or inorganic anion, present when the compound of Formula I or II is cationic.

Modification of an indolium ring of a carbocyanine dye to include a reactive group, may unexpectedly result in dye conjugates that are uniformly and substantially more fluorescent on proteins, nucleic acids and other biopolymers, than conjugates labeled with structurally similar carbocyanine dyes. In one embodiment, in addition to having more intense fluorescence emission than structurally similar dyes at virtually identical wavelengths, and decreased artifacts in their absorption spectra upon conjugation to biopolymers, certain compounds of the invention may also have greater photostability and/or higher absorbance (extinction coefficients) at the wavelength(s) of peak absorbance than such structurally similar dyes. Thus, the compounds of the invention may have significantly greater sensitivity in assays. Moreover, certain dyes described herein may exhibit a spectral shift of at least about 2 to about 5 nm, e.g., about 10 to about 20 nm.

In one embodiment, the dyes of the invention exhibit emission bands, for instance, at least about 620 nm, e.g., at least about 650, 670, 690, or 700, and some greater than about 750, nm, and so are particularly useful when employed with other dyes that have distinct emission bands, e.g., at 535 to 545 nm, 555 to 565 nm, 575 to 585 nm, 605 to 615 nm, or any combination of dyes with distinct emission bands. In one embodiment, the dyes of the invention exhibit emission bands of at least about 400 nm, e.g., at least about 420, 440, 460, 480, or 500 nm, and so are particularly useful when employed with other dyes that have distinct emission bands, e.g., at 515 to 525 nm, 535 to 545 nm, 555 to 565 nm, 575 to 585 nm, 605 to 615 nm, or any combination of dyes with distinct emission bands.

The compounds of the invention can provide better spectral resolution at the far ends of the spectrum, e.g., more blue or more red (laser detection) and also may have increased photostability, e.g., due to negative charges, for instance, di or tri sulfonated, fluorinated or phosphoramide derivatives, relative to other cyanine dyes such as Cy5.

DETAILED DESCRIPTION OF THE INVENTION

Figure 1:
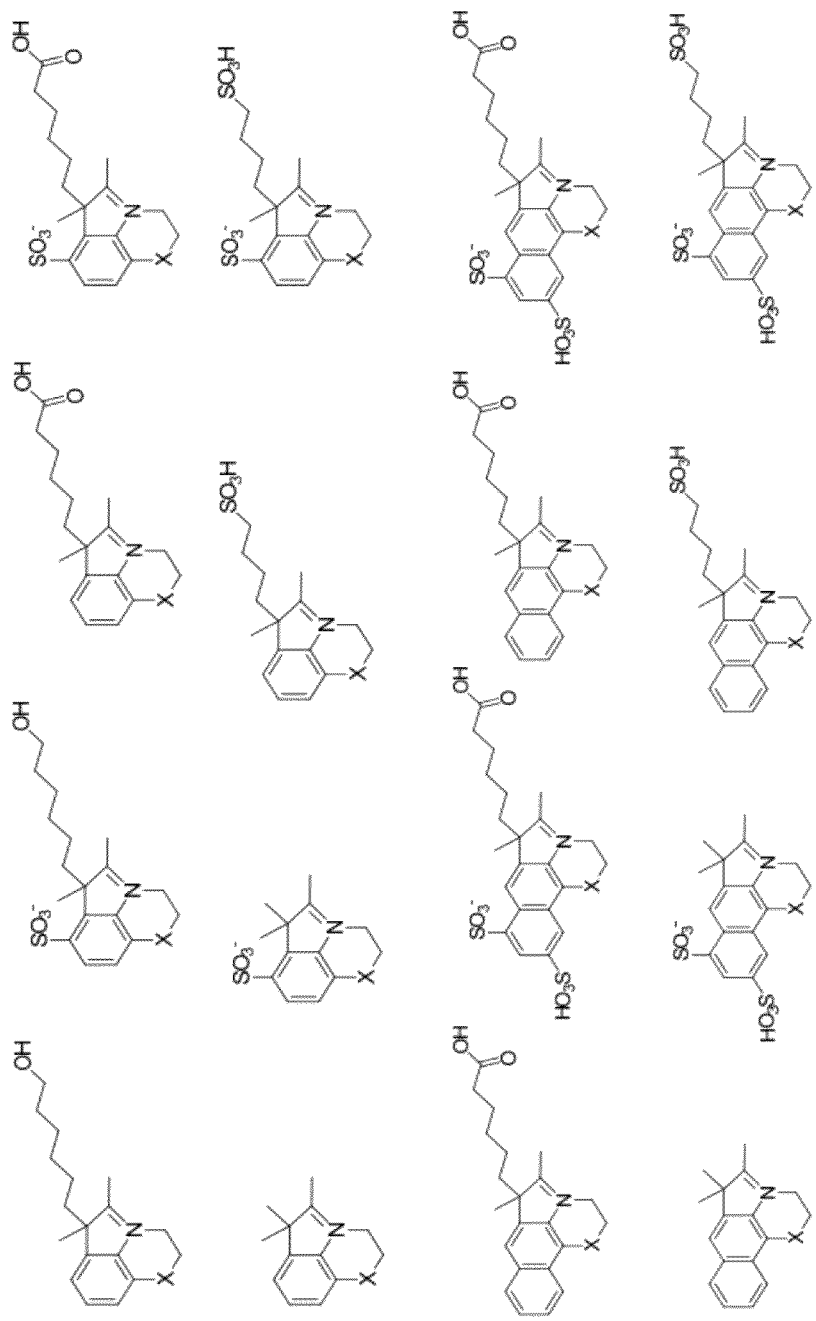
FIG. 1 illustrates various indolium derivatives that are intermediates that can be used to prepare compounds of Formula I or II, according to various embodiments.

The invention provides modified carbocyanine dyes and their conjugates. In one embodiment, the dye compounds of the invention have at least one substituted indolium ring system that contains a chemically reactive group or a conjugated substance. In one embodiment, the compounds incorporate an indolium moiety comprising three or more rings and optionally at least one sulfonate moiety. The dyes and dye conjugates may be employed to detect the interaction, presence or location of analytes or ligands in a sample. Kits incorporating the compounds or conjugates thereof are useful in such methods.

DEFINITIONS

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001. Specific values listed below for radicals, substituents, and ranges, are for illustration only; they do not exclude other defined values or other values within the defined ranges for the radicals, substituents, or term.

References in the specification to "one embodiment", "an embodiment", "an exemplary embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to use such aspect, feature, structure, moiety, or characteristic in connection with other embodiments, whether or not explicitly described.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, one or more substituents on a phenyl ring refers to one to five, or one, two, three, or four, for example if the phenyl ring is disubstituted.

The terms "stable compound" and "stable structure" indicate a compound that is sufficiently robust to survive isolation to a useful degree of purity from a reaction mixture. Typically stable compounds are claimed in the present invention, however, certain unstable compounds, for example, those that cannot easily be isolated, are also useful and can be employed, for example, in the methods described herein.

As used herein, the term "alkyl" refers to a branched or unbranched hydrocarbon having, for example, from 1 to about 20 carbon atoms, and often 1 to about 12, 1 to about 6, or 1 to about 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, nonyl, decyl, undecyl, dodecyl, and the like. The alkyl can be unsubstituted or substituted with one or more (e.g., 1, 2, 3, 4, or 5) substituents as described below. The alkyl can be a monovalent hydrocarbon radical, as described and exemplified above, or it can be a divalent hydrocarbon radical (i.e., an alkylene).

The term "alkenyl" refers to a branched, unbranched, or cyclic partially unsaturated hydrocarbon chain (i.e., one that includes a carbon-carbon, sp$^2$ double bond). In one embodiment, an alkenyl group can have from 2 to 10 carbon atoms, or 2 to 6 carbon atoms, or 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a branched or unbranched hydrocarbon chain, having a point of complete unsaturation (i.e., one that includes a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to about 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, so long as an aromatic ring is not formed. For example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "heteroaryl" refers to a monocyclic, bicyclic, or tricyclic ring system containing one, two, or three aromatic rings and containing at least one nitrogen, oxygen, or sulfur atom in an aromatic ring. Heteroaryl rings can be unsubstituted or substituted, for example, with one or more, and in particular one to three, substituents, as described above in the definition of "substituted". Typical heteroaryl groups contain 2-10 carbon atoms in addition to the one or more heteroatoms, for example, as additional rings or as alkyl substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)(alkyl)aryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. Accordingly, in some embodiments, a heterocycle can be a heteroaryl group.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.*, 82: 5566 (1960). In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroxypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —$NH_2$. The amino group can be optionally substituted as defined herein for the term "substituted". The term "alkylamino" refers to —$NR_2$, wherein at least one R is alkyl and the second R is alkyl or hydrogen. The term "acylamino" refers to —N(R)C(=O)R, wherein each R is independently hydrogen, alkyl, aryl, or (aryl)alkyl.

The term "sulfo" refers to a sulfonic acid moiety, or a salt of sulfonic acid moiety (e.g., a sulfonate). Similarly, "carboxy" refers to a carboxylic acid moiety or a salt of carboxylic acid moiety. The term "phosphate" refers to an ester of phosphoric acid, and includes salts of a phosphate moiety. The term "phosphonate" refers to a phosphonic acid moiety and includes salts of a phosphonate moiety. As used herein, unless otherwise specified, the alkyl portions of substituents such as alkyl, alkoxy, arylalkyl, alylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, hydroxy, or a combination thereof.

Protecting groups are well known in the art. Various classes of protecting groups, such as amino, hydroxyl, and carboxy protecting groups, have been extensively reviewed. See, for example, T. W. Greene, *Protecting Groups In Organic Synthesis*; Wiley: New York, Third Edition, 1999, and references cited therein; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; and F. Carey and R. Sundberg, *Advanced Organic Chemistry, Part B: Reactions and Synthesis*, (2nd Ed.), Plenum: New York, 1977; and references cited therein. Specific useful protecting groups include, for example, benzyl, benzoyl, acetyl, trimethylsilyl, tetrahydropyranyl, and t-butyldiphenylsilyl groups.

The term "interrupted" indicates that another atom or group of atoms is inserted between two adjacent carbon atoms, or between a terminal carbon atom and its adjacent group, of a particular carbon chain being referred to in the expression using the term "interrupted" to provide a heteroalkyl group, provided that each of the indicated atoms' normal valency is not exceeded, and that the interruption results in a stable compound. For example, an interrupted chain can refer to an oxygen atom being inserted between two carbons to provide an ether linkage within the carbon chain (alkyl group). Suitable groups that can interrupt a carbon chain include, e.g., with one or more non-peroxide oxy (—O—), thio (—S—), imino (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imine (C=NH), sulfinyl (SO) or sulfonyl ($SO_2$) groups. Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. In certain embodiments, one or more of the aforementioned groups are excluded from an embodiment.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

It will be appreciated that the compounds of the present invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

One diastereomer may display superior properties or activity compared with another. When required, separation of the racemic material can be achieved by HPLC using a chiral column or by a resolution using a resolving agent such as camphonic chloride as described by Tucker et al., *J. Med. Chem.*, 37: 2437 (1994). A chiral compound may also be directly synthesized using a chiral catalyst or a chiral ligand, e.g. Huffman et al., *J. Org. Chem.*, 60: 1590 (1995).

The term "linker" as used herein is an atom chain, typically a carbon chain, that covalently attaches two chemical groups together and may include a substrate for an enzyme that may be cleaved by that enzyme or another molecule, or may be photosensitive. The chain is optionally interrupted by one or more nitrogen atoms, oxygen atoms, carbonyl groups, (substituted)aromatic rings, or peptide bonds, and/or one of these groups may occur at one or both ends of the atom chain that forms the linker. Many linkers are well known in the art, and can be used to link a compound or formula described herein to another group, such as a solid support or resin. See for example, the linkers and solid supports described by Sewald and Jakubke in *Peptides: Chemistry and Biology*, Wiley-VCH, Weinheim (2002), pages 212-223; and by Dorwald in *Organic Synthesis on Solid Phase*, Wiley-VCH, Weinheim (2002).

An "effective amount" generally means an amount that provides a desired effect, for example, an amount sufficient to bring about a reaction.

As used herein, "contacting" refers to the act of touching, making contact, or of bringing to immediate or close proximity, including at the molecular level, for example, to bring about a chemical reaction or physical change, e.g., in a solution, cell, or other reaction mixture.

Dyes

The carbocyanine dyes of the invention generally include two heterocyclic ring systems bound together by a linker or bridge, where one ring system ("A") is a first heterocyclic ring system that can be a substituted benzazolium ring that optionally incorporates one or more nitrogen atoms (e.g., forming a azabenzazolium ring system), and the second ring system ("B") can be a heterocyclic ring system that is an optionally substituted benzazolium or azabenzazolium ring system.

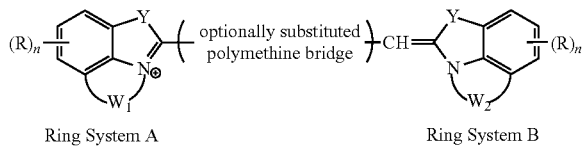

Ring System A           Ring System B

The ring systems are linked together by an optionally substituted methane or polymethine linker. The first and second ring systems and linker are optionally further substituted by a variety of substituents. The can also be fused to additional rings that are optionally further substituted. In one aspect of the invention, the carbocyanine dye contains a chemically reactive group or a conjugated substance that is attached to an indolium ring system. In one embodiment, the carbocyanine dye is further substituted by $R_1$, $R_2$ and $R_3$ so as to form a fused benzo ring that is substituted one or more times by sulfo groups, fluoro, or sulfoalkyl groups.

As described above, compounds of the invention include compounds of Formula I, and/or compounds of Formula II:

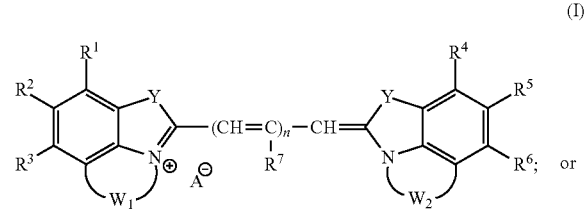

where each variable is as described above or herein below.

A compound of Formula I can also be a compound of Formula III:

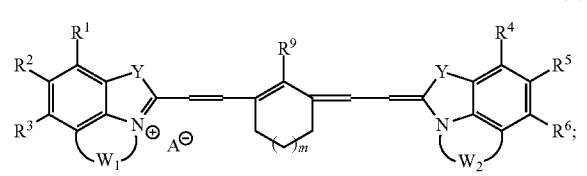

where $X_1$ and $X_2$ are each independently $CH_2$, $(CH_2)_2$, $(CH_2)_3$, NH, O, or S, and each other variable is as described above for Formula I or herein below.

In another embodiment, a compound of Formula III can also be a compound of Formula IV:

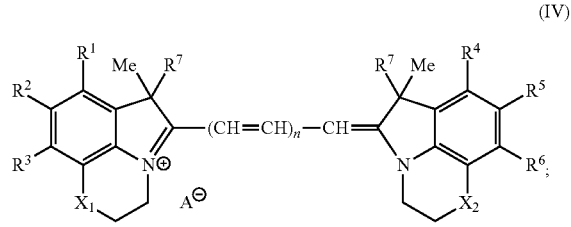

where each variable is as described above for Formula III or herein below.

A compound of Formula I can also be a compound of Formula V:

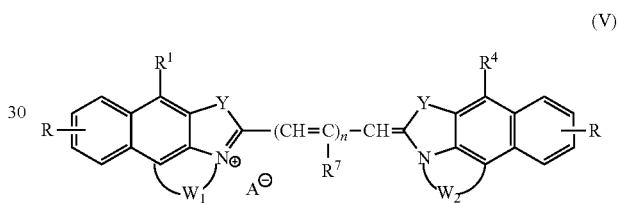

where each R is independently an alkyl, cycloalkyl, aryl, (aryl)alkyl, heteroaryl, amino, hydroxy, halo, sulfo, -L-$R^x$, $R^2$, or $R^7$, and each other variable is as described above for Formula I or herein below. One, two, three or four R groups may be present on each of the benz fused rings substituted by an R group.

A compound of Formula I can also be a compound of Formula VI:

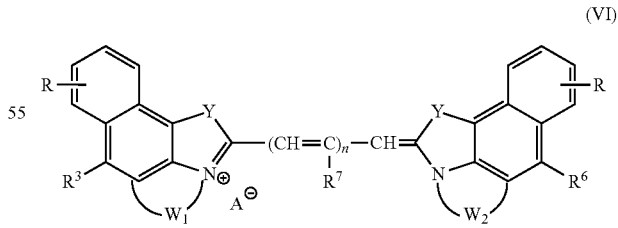

where each R is independently an alkyl, cycloalkyl, aryl, (aryl)alkyl, heteroaryl, amino, hydroxy, halo, sulfo, -L-$R^x$, $R^2$, or $R^7$, and each other variable is as described above for Formula I or herein below. One, two, three or four R groups may be present on each of the benz fused rings substituted by an R group.

A compound of Formula II can also be a compound of Formula VII:

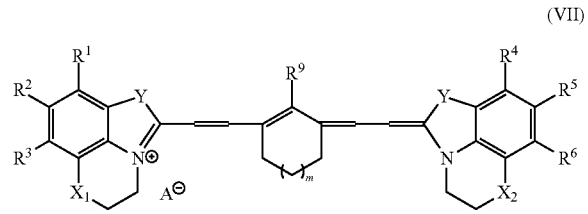

Figure 2:
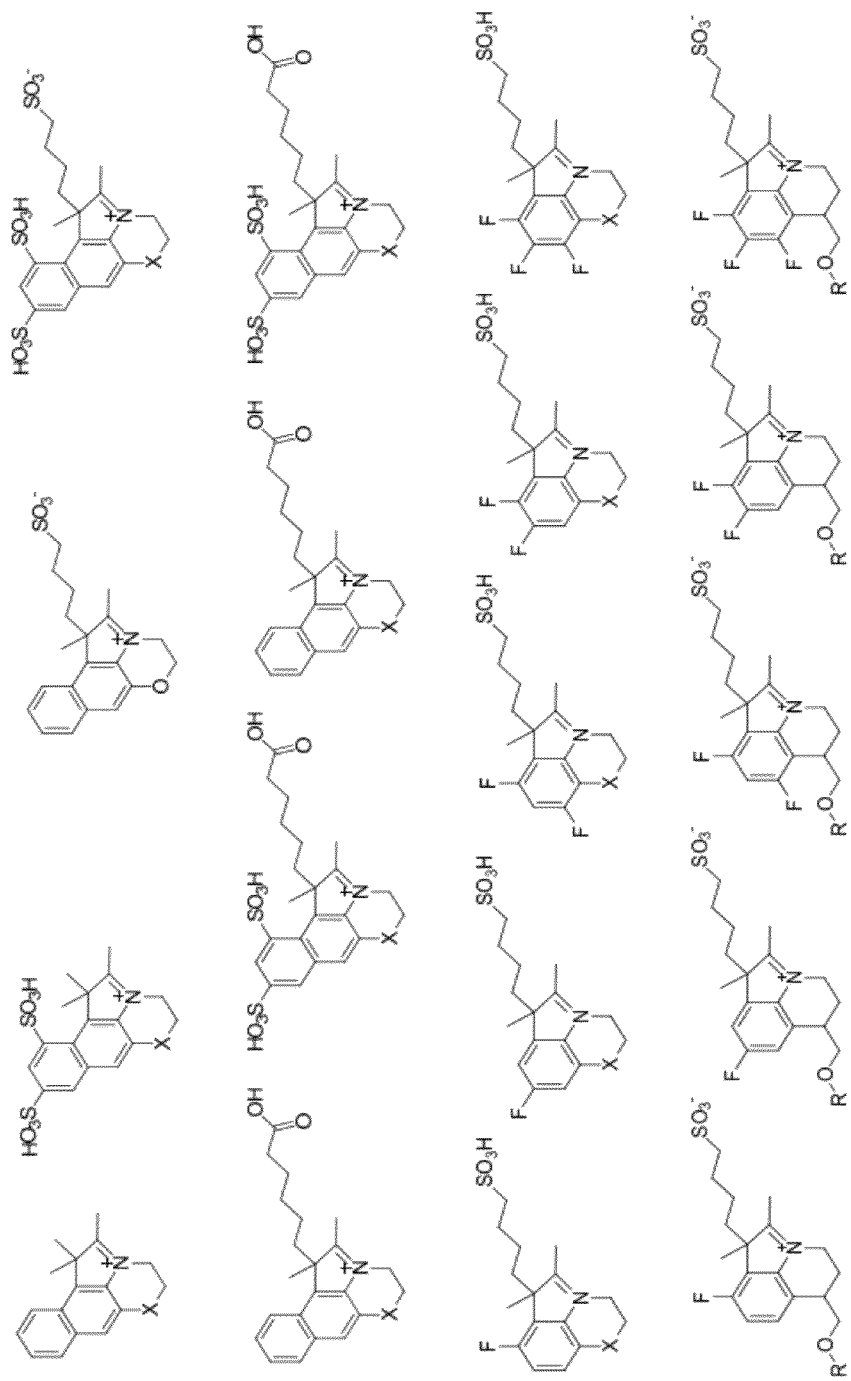
FIG. 2 illustrates various indolium derivatives that are intermediates that can be used to prepare compounds of Formula I or II, according to various embodiments.

(VII)

where $X_1$ and $X_2$ are each independently $CH_2$, $(CH_2)_2$, $(CH_2)_3$, NH, O, or S, and each other variable is as described above for Formula II or herein below. The modifications made to provide Formulas IV to VI from Formula I can also be employed to provide the corresponding formulas based on Formula II. The intermediates illustrated in FIGS. 1 and 2 provide further guidance for the variety of compounds that can be prepared within the scope of Formulas I and II.

In the various embodiments, $R^x$ can be a reactive group that can link the compound to a substance of interest, for example, to form a labeled substance. Examples of $R^x$ groups include an activated ester of a carboxylic acid comprising a —C(=O)O— group covalently bonded to a succinimidyl, a sulfosuccinimidyl, or a 1-oxybenzotriazolyl group; —NH$_2$; —OH; —SO$_2$Cl; —SO$_2$Br; —SH; —B(OH)$_2$; —B(OR)$_2$ wherein R is alkyl or aryl; —O—P(N(alkyl)$_2$)(O-alkylene-CN) (for example, a —O—P(N(iPr)$_2$)(OCH$_2$CH$_2$CN) group); —N=C=O; —C(=O)—Cl; —C(=O)—Br; —C(=O)—I; —C(=O)—NHCl; —C(=O)—NHBr; —C(=O)—NHI; —C(=O)H; —N$_3$; —C(=O)CN; a maleimide group, a diazirinyl group; an azidoaryl group; a psoralen derivative (for example, angelicin, xanthotoxin, bergapten, or nodakenetin attached an available carbon such as at carbon 3, 4, 5, 8, 4', 5', or though one of its substituents or through a linker); a benzophenone (for example, linked at a carbon ortho, meta, or para to the benzophenone carbonyl); a 4-cyanobenzothiazole (for example, linked through a oxygen atom at the benzothiazole 4', 5', 6', or 7' carbon), a ($C_1$-$C_7$)alkyl-methylene chloride, a ($C_1$-$C_7$)alkyl-methylene bromide, a ($C_1$-$C_7$)alkyl-methylene iodide, —CO$_2$H, or —SO$_3$H. Examples of the ($C_1$-$C_7$)alkyl-methylene halide groups include ethyl halide, propyl halide, butyl halide, pentyl halide, hexyl halide, or heptyl halide, and branched derivatives thereof.

In one embodiment, $R^1$, $R^2$, $R^3$, $R^4$, $R^5$, and $R^6$ are each independently H, halo (e.g., F, Cl, Br, or I), sulfo, or ($C_1$-$C_8$) sulfo.

In one embodiment, $W_1$ forms a 6-membered ring having a —CH$_2$—, —O—, —S—, or —NH— para to the N of the $W_1$ ring in Formula I or II. In another embodiment, $W_1$ forms a 7- or 8-membered ring that includes a —CH$_2$—, —O—, —S—, or —NH— within the $W_1$ ring in Formula I or II, for example, one, two, three, four, or five atoms away from the N of Formula I or II.

In another embodiment, $W_2$ forms a 6-membered ring having a —CH$_2$—, —O—, —S—, or —NH— para to the N of the $W_2$ ring in Formula I or II. In another embodiment, $W_2$ forms a 7- or 8-membered ring that includes a —CH$_2$—, —O—, —S—, or —NH— within the $W_2$ ring in Formula I or II, for example, one, two, three, four, or five atoms away from the N of Formula I or II.

In one embodiment, $W_1$, $W_2$, or both, are substituted on a carbon of the ring with —(CH$_2$)$_m$—OH, —(CH$_2$)$_m$—CO$_2$H, or —(CH$_2$)$_m$—$R^x$ where m is 1 to about 12.

In one embodiment, $R^1$ and $R^2$ taken together with the atoms to which they are attached form a fused benzo ring. The benzo ring can be substituted with 1, 2, 3, or 4 alkyl, cycloalkyl, aryl, (aryl)alkyl, heteroaryl, amino, hydroxy, halo, sulfo, or -L-$R^x$ groups. In another embodiment, $R^2$ and $R^3$ form such a fused benzo ring. In another embodiment, $R^4$ and $R^5$ form such a fused benzo ring. In yet another embodiment, $R^5$ and $R^6$ form such a fused benzo ring.

In one embodiment, each Y is independently $CR^7R^7$, S, O, $CF_2$, or $NR^7$. In another embodiment, each Y is $CR^7R^7$, S, O, $CF_2$, or $NR^7$. When a Y is $CR^7R^7$, one $R_7$ of Y can be an alkyl group, such as methyl, and the other $R^7$ of Y can be -L-$R^x$.

Each L is independently a direct bond or a linker, wherein the linker is a divalent radical of the formula -A-B-Z- wherein each A is independently a direct bond or a ($C_1$-$C_{12}$)alkyl chain optionally comprising one or more unsaturations, optionally substituted by one or more oxo groups, and optionally interrupted by one or more O atoms. The interruption by the O atom can be between two carbon atoms, before the first carbon atom, or after the last carbon atom, of the group A. Each B is independently a direct bond or a —NHC(=O)—, —C(=O)NH—, —OC(=O)—, —C(=O)O—, —O—, or —N($R^8$)— group; where each $R^8$ is independently H, ($C_1$-$C_6$)alkyl, or a nitrogen protecting group. Each Z is independently a direct bond or a ($C_1$-$C_{20}$)alkyl chain optionally comprising one or more unsaturations, optionally substituted by one or more oxo groups, and optionally interrupted by one or more O atoms; The interruption by the O atom can be between two carbon atoms, before the first carbon atom, or after the last carbon atom, of the group Z.

In one embodiment, L is ($C_1$-$C_{12}$)alkyl or ($C_1$-$C_{12}$)alkyl-B-(CH$_2$CH$_2$O)$_n$(CH$_2$)$_m$— wherein n is 1-6, m is 1-8, and B is —NHC(=O)—, —C(=O)NH—, —OC(=O)—, —C(=O)O—, —O—, —NH—, or a direct bond. In another embodiment, at least one L is ($C_1$-$C_{10}$)alkyl or ($C_1$-$C_{12}$)alkyl-C(=O)NH—(CH$_2$CH$_2$O)$_n$(CH$_2$)$_m$— wherein n is 1-6 and m is 1-8.

In another embodiment, each B can be independently a direct bond or —X—C(=Z)—X— where Z is O or S; and X is O, NH, or S. Specific values of B can include O, S, NH, —O—C(=O)—, —NH—C(=O)—, —S—C(=O)—, —C=N—, carbonyl, —O—C(=O)—O—, —O—C(=O)—NH—, —O—C(=O)—S—, —O—C(=S)—O—, —O—C(=S)—NH—, and —O—C(=S)—S—.

In another embodiment, each L is independently a direct bond or a linker, wherein the linker is a divalent radical of the formula -Z-A-Z- wherein each Z is independently —(CH$_2$)$_n$— where n is 1-12, —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H, ($C_1$-$C_6$)alkyl, or a nitrogen protecting group; and A is ($C_1$-$C_{20}$)alkyl, ($C_2$-$C_{16}$)alkenyl, ($C_2$-$C_{16}$)alkynyl, ($C_3$-$C_8$)cycloalkyl, ($C_6$-$C_{10}$)aryl, —(OCH$_2$—CH$_2$)$_n$— where n is 1 to about 20, —C(O)NH(CH$_2$)$_n$ wherein n is 1 to about 6; or ($C_1$-$C_{20}$)alkyl, ($C_2$-$C_{16}$)alkenyl, ($C_2$-$C_{16}$)alkynyl, or —(OCH$_2$—CH$_2$)$_n$— interrupted between two carbons, or between a carbon and an oxygen, with a ($C_3$-$C_8$)cycloalkyl or ($C_6$-$C_{10}$)aryl group.

In certain embodiments, the linking group L can be a divalent radical of the formula W-A wherein A is ($C_1$-$C_6$) alkyl, ($C_2$-$C_6$)alkenyl, ($C_2$-$C_6$)alkynyl, ($C_3$-$C_8$)cycloalkyl, or ($C_6$-$C_{10}$)aryl; W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; each R is independently H, ($C_1$-$C_6$)alkyl, or a protecting group; and the linking group L links together the reactive group $R^x$ and the illustrated portion of Formula I or II.

In some embodiments, the linking group L can be a linking group comprising $(C_1-C_{16})$alkyl optionally substituted with one or more (e.g., 1, 2, 3, 4, 1-5, or 1-6) halo, hydroxy, oxo, $(C_1-C_6)$alkyl, or $(C_1-C_6)$alkoxy, and optionally interrupted with one or more (e.g., 1, 2, 3, 4, 1-5, or 1-6) $N(R^1)$, O, S, or —N—C(=O)— groups. The term "optionally interrupted" can means that one or more, e.g., 1, 2, 3, 4, 1-5, or 1-6, carbon atoms of the linking group, including one or both terminal carbons of the linking group, can be replaced with an O, $N(R^1)$, S, or —N—C(=O)— group. In some embodiments, L can optionally be absent, for example, when $R^x$ is azido ($N_3$). In some embodiments, L can be —$(C_1-C_6)$alkyl-, —O—$(C_1-C_6)$alkyl-, —O—$(C_1-C_6)$alkyl-O—, —O—$(C_1-C_6)$alkyl-NH—, —O—$(C_1-C_6)$alkyl-(CO)NH—, —NH—$(C_1-C_6)$alkyl-NH—, —NH—(CO)$(C_1-C_6)$alkyl-NH—, —NH—(CO)$(C_1-C_6)$alkyl-(CO)—NH—, or —O—$(C_1-C_6)$alkyl-(CO)NH—$(C_1-C_6)$alkyl-.

In one embodiment, $R^9$ of Formula II is —OPh-CO$_2$H; —OPh-NH—$(C_1-C_{12})$alkyl-$R^x$, or —OPh-C(=O)NH—(CH$_2$CH$_2$O)n(CH$_2$)m-$R^x$, wherein n is 1-6, m is 1-8.

In some embodiment, each $R^7$ is independently H, $(C_1-C_8)$alkyl, aryl, (aryl)alkyl, or -L-$R^x$.

In one embodiment, m of Formula II is 1. In another embodiment, m is 0.

In one embodiment, n of Formula I is 1 or 2. In another embodiment, n is 0.

In one embodiment, two, three, or four -L-$R^x$ group are present in the compound of Formula I or II.

In one embodiment, Formula I or Formula II is cationic and the compound includes a counterion, for example, an inorganic anion, such as a halo anion, a sulfate anion, or a halosulfate anion. In another embodiment, the counterion is an organic anion, such as carbonate, acetate, or trifluoroacetate. In some embodiments, Formula I and/or Formula II is overall neutral. In such cases, counterions may optionally be present in conjunction with charged groups on the molecule.

In one embodiment, the compound is:

5-((1E,3E,5E)-5-(1,1-dimethyl-5,6-dihydro-1H-pyrrolo[3,2,1-ij]quinolin-2(4H)-ylidene)penta-1,3-dienyl)-6-(6-(2,5-dioxopyrrolidin-1-yloxy)-6-oxohexyl)-6-methyl-1,2,3,6-tetrahydropyrrolo[3,2,1-ij]quinolinium trifluoroacetate (3525);

6-(6-((2-Cyanoethoxy)(diisopropylamino)phosphinooxy) hexyl)-5-((1E,3E,5E)-5-(1,1-dimethyl-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij] quinolinium chloride (3742);

(E)-2-((2E,4E)-5-(6-(6-(2,5-Dioxopyrrolidin-1-yloxy)-6-oxohexyl)-6-methyl-7-sulfo-1,2,3,6-tetrahydropyrrolo[3,2,1-ij]quinolinium-5-yl)penta-2,4-dienylidene)-1,1-dimethyl-2,4,5,6-tetrahydro-1H-pyrrolo[3,2,1-ij]quinoline-9-sulfonate (3526);

6-(25-chloro-6-oxo-10,13,16,19-tetraoxa-7-azapentacosyl)-5-((1E,3E,5E)-5-(1,1-dimethyl-9-sulfo-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium-7-sulfonate (3665);

5-((1E,3E)-3-((E)-2-(1,1-Dimethyl-5,6-dihydro-1H-pyrrolo[3,2,1-ij]quinolin-2(4H)-ylidene)ethylidene)-6-hydroxyhex-1-enyl)-6,6-dimethyl-1,2,3,6-tetrahydropyrrolo[3,2,1-ij]quinolinium chloride (3688);

(E)-2-((E)-3-((E)-2-(6,6-Dimethyl-7-sulfo-1,2,3,6-tetrahydropyrrolo[3,2,1-ij]quinolinium-5-yl)vinyl)-6-hydroxyhex-2-enylidene)-1,1-dimethyl-2,4,5,6-tetrahydro-1H-pyrrolo[3,2,1-ij]quinoline-9-sulfonate (3786);

5-((1E,3E)-3-(1,1-Dimethyl-5,6-dihydro-1H-pyrrolo[3,2,1-ij]quinolin-2(4H)-ylidene)prop-1-enyl)-6-(6-hydroxyhexyl)-6-methyl-1,2,3,6-tetrahydropyrrolo[3,2,1-ij] quinolinium chloride (3785);

Sodium 2-((1E,3Z)-3-(1-(5-carboxypentyl)-1-methyl-9-sulfonato-5,6-dihydro-1H-pyrrolo[3,2,1-ij]quinolin-2(4H)-ylidene)prop-1-enyl)-1-methyl-1-(4-sulfonatobutyl)-1,4,5,6-tetrahydropyrrolo[3,2,1-ij]quinolinium-9-sulfonate (3845);

Sodium 2-((1E,3Z)-3-(1-(6-(2-(2-(6-chlorohexyloxy) ethoxy)ethylamino)-6-oxohexyl)-1-methyl-9-sulfonato-5,6-dihydro-1H-pyrrolo[3,2,1-ij]quinolin-2(4H)-ylidene) prop-1-enyl)-1-methyl-1-(4-sulfonatobutyl)-1,4,5,6-tetrahydropyrrolo[3,2,1-ij]quinolinium-9-sulfonate (3838);

6-((Z)-5-((2E,4E)-5-(6,6-Dimethyl-1,2,3,6-tetrahydrobenzo [f]pyrrolo[3,2,1-ij]quinolinium-5-yl)penta-2,4-dienylidene)-6-methyl-2,3,5,6-tetrahydro-1H-benzo[f]pyrrolo[3,2,1-ij]quinolin-6-yl)hexanoate (3846);

Sodium 2-((1E,3E,5Z)-5-(1-(6-(2-(2-(6-chlorohexyloxy) ethoxy)ethylamino)-6-oxohexyl)-1-methyl-9-sulfonato-5,6-dihydro-1H-pyrrolo[3,2,1-ij]quinolin-2(4H)-ylidene) penta-1,3-dienyl)-1-methyl-1-(4-sulfonatobutyl)-1,4,5,6-tetrahydropyrrolo[3,2,1-ij]quinolinium-9-sulfonate (3847);

Sodium 5-((1E,3E,5Z)-5-(1-(5-carboxypentyl)-1-methyl-9-sulfonato-5,6-dihydro-1H-pyrrolo[3,2,1-ij]quinolin-2 (4H)-ylidene)penta-1,3-dienyl)-6-methyl-6-(4-sulfonatobutyl)-1,2,3,6-tetrahydropyrrolo[3,2,1-ij]quinolinium-7-sulfonate (3848);

Sodium 5-((E)-2-((E)-2-(4-carboxyphenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl)vinyl)-6-methyl-6-(4-sulfonatobutyl)-1,2,3,6-tetrahydropyrrolo[3,2,1-ij]quinolinium-7-sulfonate (3855);

Sodium 2-((E)-2-((E)-2-(4-(2-(2-(6-chlorohexyloxy)ethoxy) ethylcarbamoyl)phenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl) vinyl)-1-methyl-1-(4-sulfonatobutyl)-1,4,5,6-tetrahydropyrrolo[3,2,1-ij]quinolinium-9-sulfonate (3856); or 5-((E)-2-((E)-3-((Z)-2-(1-(25-Chloro-6-oxo-10,13,16,19-tetraoxa-7-azapentacosyl)-1-methyl-9-sulfo-5,6-dihydro-1H-pyrrolo[3,2,1-ij]quinolin-2(4H)-ylidene)ethylidene)-2-(4-sulfophenoxy)cyclohex-1-enyl)vinyl)-6-methyl-6-(4-sulfobutyl)-1,2,3,6-tetrahydropyrrolo[3,2,1-ij] quinolinium-7-sulfonate (3921).

Conjugates of Reactive Dyes

In one embodiment of the invention, the dye contains at least one group -L-$R^x$, where $R^x$ is a reactive group that is attached to the dye by a covalent linkage L. In some embodiments, the dye contains 1, 2, 3, 4, 5, 6, 7, 8, 9, or 10 -L-$R^x$ groups, where each $R^x$ can be a sulfo group or a reactive group that is attached to the dye by a covalent linkage L. In certain embodiments, the covalent linkage attaching the dye to $R^x$ contains multiple intervening atoms that serve as a spacer. Dyes with a reactive group ($R^x$) label a wide variety of organic or inorganic substances that contain or are modified to contain functional groups with suitable reactivity, resulting in chemical attachment of the conjugated substance ($S_c$), represented by -L-$S_c$. As used herein, the term "reactive group" includes a moiety on the compound that is capable of chemically reacting with a functional group on a different compound to form a covalent linkage. Typically, the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group $R^x$ incorporated into a new linkage L attaching the dye to the conjugated substance $S_c$. Selected examples of reactive groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group.
**Acyl azides can also rearrange to isocyanates.

Suitable leaving group are well known in the art and include groups such as succinimidyloxy (—OC$_4$H$_4$O$_2$), sulfosuccinimidyloxy (—OC$_4$H$_3$O$_2$SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are $C_1$-$C_6$ alkyl, $C_1$-$C_6$ perfluoroalkyl, $C_1$-$C_8$ alkoxy, cycloalkyl (e.g., cyclohexyl), N,N-dialkylaminoalkyl (e.g., 3-dimethylamino-propyl), or N-morpholinoethyl.

The covalent linkage L binds the reactive group $R^x$ or conjugated substance $S_c$ to the compound, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and nitrogen-platinum bonds. L typically includes ether, thioether, carboxamide, sulfonamide, urea, urethane or hydrazine moieties. L moieties may have 1 to 20 nonhydrogen atoms selected from the group consisting of C, N, O, P, and S; and may be composed of any combination of ether, thioether, amine, ester, carboxamide, sulfonamide, hydrazide bonds and aromatic or heteroaromatic bonds.

In one embodiment, L is a combination of single carbon-carbon bonds and carboxamide or thioether bonds. In one embodiment, the longest linear segment of the linkage L may contain 4 to 10 nonhydrogen atoms, including one or two heteroatoms. Examples of L include substituted or unsubstituted polymethylene, arylene, alkylarylene, arylenealkyl, or arylthio. In one embodiment, L may contain 1 to 6 carbon atoms; in another, L may include a thioether linkage and 1 to 6 carbon atoms. In yet another embodiment, L is or has the formula —(CH$_2$)$_d$(CONH(CH$_2$)$_e$)$_z$'—, or —(CH$_2$)$_d$(CON(CH$_2$)$_4$NH(CH$_2$)$_e$)$_z$'—, —(CH$_2$)$_d$(CONH(CH$_2$)$_e$NH$_2$)$_z$'—, —(CH$_2$)$_d$(CONH(CH$_2$)$_e$NHCO)$_z$'—, where d is 0 to 5, e is 1 to 5, and z' is 0 or 1.

Selection of the reactive group used to attach the dye to the substance to which it is be conjugated typically depends on the functional group on the substance to be conjugated and the type or length of covalent linkage desired. Functional groups typically present on the organic or inorganic substances include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g., amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, $R^x$ will react with an amine, a thiol, an alcohol, an aldehyde or a ketone. In one embodiment, $R^x$ reacts with an amine or a thiol functional group. In one embodiment, $R^x$ is an acrylamide, a reactive amine (including a cadaverine (—NH(CH$_2$)$_5$NH$_2$) or ethylenediamine (—NH(CH$_2$)$_2$NH$_2$)), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. The term "reactive platinum complex" refers to chemically reactive platinum complexes such as those described in U.S. Pat. Nos. 5,580,990; 5,714,327; and 5,985,566.

When the reactive group is a photoactivatable group, such as an azide, diazirinyl, azidoaryl, or psoralen derivative, the dye becomes chemically reactive only after illumination with light of an appropriate wavelength.

When $R^x$ is an activated ester of a carboxylic acid, the reactive dye may be useful for preparing dye-conjugates of proteins, nucleotides, oligonucleotides, or haptens. When $R^x$ is a maleimide or haloacetamide, the reactive dye may be useful for conjugation to thiol-containing substances. When $R^x$ is a hydrazide, the reactive dye may be useful for conjugation to periodate-oxidized carbohydrates and glycoproteins, and in addition may be an aldehyde-fixable polar tracer for cell microinjection.

In one embodiment, $R^x$ is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. In one embodiment, $R^x$ is a succinimidyl ester of a carboxylic acid, a maleimide, an iodoacetamide, or a reactive platinum complex. In one embodiment, $R^x$ is a reactive platinum complex, or a succinimidyl ester of a carboxylic acid. When $R^x$ is a reactive platinum complex, it is typically a haloplatinate or a platinum nitrate.

Based on the above-mentioned attributes, the appropriate reactive dye of the invention is selected for the preparation of a desired dye-conjugate.

Useful dye-conjugates include, but are not limited to, conjugates where $S_c$ is an antigen, steroid, vitamin, drug, hapten, metabolite, toxin, environmental pollutant, amino acid, peptide, protein, nucleotide, nucleic acid polymer (oligonucleotide or polynucleotide), carbohydrate, lipid, ion-complexing moiety, or glass, plastic or other non-biological polymer. $S_c$ may be a cell, such as animal cell, plant cell, bacteria, yeast, or protest, or subcellular particle, e.g., a virus particle or component thereof, or subcellular component of a bacterium or eukaryotic cell. Reactive dyes may label functional groups at the cell surface, in cell membranes, organelles, or the cytoplasm.

In one embodiment, $S_c$ is an amino acid, peptide, protein, tyramine, polysaccharide, ion-complexing moiety, nucleoside, nucleotide, oligonucleotide, polynucleotide, hapten, psoralen, drug, hormone, lipid, lipid assembly, polymer, polymeric microparticle, biological cell or virus. In one embodiment, $S_c$ is a peptide, a protein, a nucleotide, an oligonucleotide, or a polynucleotide. When conjugating dyes of the invention to such biopolymers, more than one dye molecule per biopolymer may be incorporated to increase the fluorescent signal. For example, at least four molecules of a dye may be conjugated per molecule of antibody. The fluorescence of labeled conjugates of the invention to available conjugates of the formulas described herein may show at least a two-fold enhancement in fluorescence.

In one embodiment, $S_c$ is a ligand or a hapten, such as biotin, or a phenol such as tyramine, or a molecule useful as a substrate for horseradish peroxidase.

In one embodiment, $S_c$ is a biological polymer such as a peptide, protein, oligonucleotide, or polynucleotide that is also labeled with at least a second non-fluorescent or fluorescent dye (e.g., optionally an additional dye of the invention), to form an energy-transfer pair. In some aspects of the invention, the labeled conjugate functions as an enzyme substrate, and enzymatic hydrolysis disrupts the energy transfer. Alternatively, $S_c$ is a fluorescent or nonfluorescent dye, optionally an additional dye of the present invention, which dye-conjugate forms a labeling complex that exhibits a large Stokes shift due to internal energy-transfer (as described in U.S. Pat. No. 6,008,373), which complex is useful to label an organic or inorganic substance.

In one embodiment, $S_c$ is an amino acid (including those that are protected or are substituted by phosphates, carbohydrates, or $C_1$ to $C_{22}$ carboxylic acids), or is a polymer of amino acids such as a peptide or protein. In one embodiment, conjugates of peptides contain at least five amino acids, e.g., 5 to 36 amino acids. Exemplary peptides include, but are not limited to, neuropeptides, cytokines, toxins, protease substrates, and protein kinase substrates. Exemplary protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one embodiment, the conjugated protein is a phycobiliprotein, such as allophycocyanin, phycocyanin, phycoerythrin, allophycocyanin B, B-phycoerythrin, phycoerythrocyanin, and b-phycoerythrin (for example, see U.S. Pat. No. 5,714, 386). In one embodiment, conjugates of R-phycoerythrin and of allophycocyanin with selected dyes of the invention that serve as excited-state energy acceptors or donors. In these conjugates, excited state energy transfer may result in long wavelength fluorescence emission when excited at relatively short wavelengths. In another aspect of the invention, the conjugated protein is an antibody, an antibody fragment, avidin, streptavidin, a toxin, a lectin, a hormone, a chemokine, or a growth factor. Where the conjugated substance is a toxin, it may be a neuropeptide or a phallotoxin, such as phalloidin.

In another embodiment, $S_c$ is a nucleic acid base, nucleoside, nucleotide, oligonucleotide or a polynucleotide, including those that are modified to possess an additional linker or spacer for attachment of the dyes of the invention, such as an alkynyl linkage (as in U.S. Pat. No. 5,047,519), an aminoallyl linkage (as in U.S. Pat. No. 4,711,955), or a heteroatom-substituted linker (as in U.S. Pat. No. 5,684,142), or other linkage. In another embodiment, the conjugated substance is a nucleoside or nucleotide analog that links a purine or pyrimidine base to a phosphate or polyphosphate moiety through a noncyclic spacer. In another embodiment, the dye is conjugated to the carbohydrate portion of a nucleotide or nucleoside, typically through a hydroxyl group but optionally additionally through a thiol or amino group (see U.S. Pat. Nos. 5,659,025; 5,668,268; and 5,679,785). Typically, the conjugated nucleotide is a nucleoside triphosphate or a deoxynucleoside triphosphate or a dideoxynucleoside triphosphate.

Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g., Atamna et al., *Proc. Natl. Acad. Sci. USA*, 97:686 (2000).

Polynucleotide or oligonucleotide conjugates may contain single- or multi-stranded, natural or synthetic DNA or RNA, or form part of DNA/RNA hybrids, or incorporate a linker such as morpholine derivatized phosphates (AntiVirals, Inc., Corvallis Oreg.), or peptide nucleic acids such as N-(2-aminoethyl)glycine units. When the conjugate includes an oligonucleotide, it typically contains fewer than 50 nucleotides, more typically 25 or fewer nucleotides. Conjugates of peptide nucleic acids (PNA) (U.S. Pat. No. 5,539,082) generally have faster hybridization rates.

Fluorescent oligonucleotides or polynucleotides may be prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Fluorescent RNA polymers may be prepared from labeled nucleotides by transcription. Typically, the dye is attached via one or more purine or pyrimidine bases through an amide, ester, ether or thioether bond; or is attached to the phosphate or carbohydrate by a bond that is an ester, thioester, amide, ether or thioether. Alternatively, a dye conjugate of the invention may be simultaneously labeled with a hapten such as biotin or digoxigenin, or to an enzyme such as alkaline phosphatase, or to a protein such as an antibody. Nucleotide conjugates of the invention are readily incorporated by DNA polymerase and can be used for in situ hybridization and nucleic acid sequencing (e.g., U.S. Pat. Nos. 5,332,666; 5,171,534; and 4,997,928, and WO 94/05688).

In one aspect of the invention, the oligonucleotide incorporates an aliphatic amine, which is subsequently conjugated to an amine-reactive dye of the invention or a thiol or thiophosphate, which is conjugated to a thiol-reactive dye of the invention. In yet another aspect of the invention, the purine bases of the oligonucleotide react with a reactive metal complex (e.g., a platinum complex) bound to a dye of the invention, yielding a dye-conjugate. Nucleic acid conjugates of dyes of the invention may have spectral properties that are superior to those of structurally similar carbocyanine dyes.

In one embodiment, the conjugated oligonucleotides of the invention are aptamers for a particular target molecule, such as a metabolite, dye, hapten, or protein. That is, the oligonucleotides have been selected to bind to the target molecule. Methods of preparing and screening aptamers for a given target molecule have been previously described and are known in the art (for example, U.S. Pat. No. 5,567,588).

In another embodiment, the conjugated substance ($S_c$) comprises a carbohydrate that is typically a polysaccharide, such as a dextran, FICOLL™ polysaccharide, heparin, glycogen, amylopectin, mannan, inulin, starch, agarose, or cellulose. Alternatively, the carbohydrate is a polysaccharide that comprises a lipopolysaccharide. Exemplary polysaccharide conjugates are dextran, FICOLL™ polysaccharide, or lipopolysaccharide conjugates.

In another embodiment, the conjugated substance ($S_c$) comprises a lipid (typically having 6 to 60 carbons), including glycolipids, phospholipids, sphingolipids, and steroids. Alternatively, the conjugated substance includes a lipid assembly, such as a liposome. The lipophilic moiety may be used to retain the conjugated substances in cells, as described in U.S. Pat. No. 5,208,148. Certain polar dyes of the invention may also be trapped within lipid assemblies.

In another embodiment, the conjugated substance ($S_c$) comprises a cyanobenzothiazole moiety. In certain embodiments, the cyanobenzothiazole moiety has the formula (VIII):

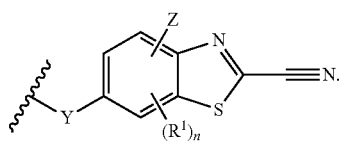

(VIII)

In formula (III), the variable Z can be H, F, Cl, Br, I, CN, amino, alkylamino, dialkylamino, alkyl ester (e.g., —$CO_2$(alkyl)), carboxy, carboxylic acid salt, alkyl amide (—C(=O)NH(alkyl)), phosphate (—OPO(OH)$_2$), alkyl phosphonate, sulfate (—OSO$_3$H), alkyl sulfonate, nitro, or ($C_1$-$C_{10}$) alkyl optionally unsaturated and optionally substituted with amino, hydroxy, oxo (=O), nitro, thiol, or halo. The group Z can be located at the 4', 5', or 7' position of the cyanobenzothiazole. In certain embodiments, Z is located at the 7' position.

In formula (III), each $R^1$ can independently be H, F, Cl, Br, I, CN, ($C_1$-$C_6$)alkyl, ($C_1$-$C_6$)alkoxy, or ($C_1$-$C_6$)alkylthio, wherein each alkyl, alkoxy, or alkylthio is optionally substituted with F, Cl, Br, I, amino, alkenyl, alkynyl, cycloalkyl, aryl, alkyl sulfonate, or $CO_2M$ wherein M is H, an organic cation, or an inorganic cation; wherein n is 0, 1, or 2. The group or groups $R^1$ can be located at the 4', 5', or 7' position of the cyanobenzothiazole. In certain embodiments, Z can be located at the 7' position.

In formula (III), the group Y can be a linking group comprising ($C_1$-$C_{16}$)alkyl optionally substituted with one or more (e.g., 1, 2, 3, 4, 1-5, or 1-6) halo, hydroxy, oxo, ($C_1$-$C_6$)alkyl, or ($C_1$-$C_6$)alkoxy, and optionally interrupted with one or more (e.g., 1, 2, 3, 4, 1-5, or 1-6) N($R^1$), O, S, or —N—C(=O)— groups, or Y can be absent. The term "optionally interrupted" means that one or more, e.g., 1, 2, 3, 4, 1-5, or 1-6, carbon atoms of the linking group, including one or both terminal carbons of the linking group, can be replaced with an O, N($R^1$), S, or —N—C(=O)— group. In some embodiments, Y can optionally be absent, for example, when X is azido ($N_3$). For example, in some embodiments, Y can be —($C_1$-$C_6$)alkyl-, —O—($C_1$-$C_6$)alkyl-, —O—($C_1$-$C_6$)alkyl-O—, —O—($C_1$-$C_6$)alkyl-NH—, —O—($C_1$-$C_6$)alkyl-(CO)NH—, —NH—($C_1$-$C_6$)alkyl-NH—, —NH—(CO)($C_1$-$C_6$)alkyl-NH—, —NH—(CO)($C_1$-$C_6$)alkyl-(CO)—NH—, or —O—($C_1$-$C_6$)alkyl-(CO)NH—($C_1$-$C_6$)alkyl-.

Conjugates having an ion-complexing moiety may serve as indicators for calcium, sodium, magnesium, zinc, potassium, or other biologically important metal ions. Exemplary ion-complexing moieties are crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517; 5,516,911; and 5,049,673); derivatives of 2-carboxymethoxyaniline-N,N-diacetic acid (APTRA chelators; *Am. J. Physiol.*, 256:C540 (1989)); pyridine- and phenanthroline-based metal ion chelators (U.S. Pat. No. 5,648,270); or derivatives of nitrilotriacetic acid, see McMahan et al., *Anal. Biochem.*, 236:101 (1996); incorporated by reference. In one embodiment, the ion-complexing moiety is a crown ether chelator, a BAPTA chelator, an APTRA chelator or a derivative of nitrilotriacetic acid.

Other conjugates of non-biological materials include dye-conjugates of organic or inorganic polymers, polymeric films, polymeric wafers, polymeric membranes, polymeric particles, or polymeric microparticles; including magnetic and non-magnetic microspheres; iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

In one aspect of the invention, $S_c$ comprises an antibody (including intact antibodies, antibody fragments, and antibody sera, and the like), an amino acid, an angiostatin or endostatin, an avidin or streptavidin, a biotin (e.g., an amidobiotin, a biocytin, a desthiobiotin, and the like), a blood component protein (e.g., an albumin, a fibrinogen, a plasminogen, and the like), a dextran, an enzyme, an enzyme inhibitor, an IgG-binding protein (e.g., a protein A, protein G, protein A/G, and the like), a fluorescent protein (e.g., a phycobiliprotein, an aequorin, a green fluorescent protein, and the like), a growth factor, a hormone, a lectin (e.g., a wheat germ agglutinin, a conconavalin A, and the like), a lipopolysaccharide, a metal-binding protein (e.g., a calmodulin, and the like), a microorganism or portion thereof (e.g., a bacteria, a virus, a yeast, and the like), a neuropeptide and other biologically active factors (e.g., a dermorphin, a deltropin, an endomorphin, an endorphin, a tumor necrosis factor, and the like), a non-biological microparticle (e.g., of ferrofluid, gold, polystyrene, and the like), a nucleotide, an oligonucleotide, a peptide toxin (e.g., an apamin, a bungarotoxin, a phalloidin, and the like), a phospholipid-binding protein (e.g., an annexin, and the like), a small-molecule drug (e.g., a methotrexate, and the like), a structural protein (e.g., an actin, a fibronectin, a laminin, a microtubule-associated protein, a tubulin, and the like), or a tyramide.

In one embodiment, conjugates of biological polymers such as peptides, proteins, oligonucleotides, or polynucleotides are also labeled with at least a second fluorescent or nonfluorescent dye, that is optionally an additional dye of the present invention, to form an energy-transfer pair. In some aspects of the invention, the labeled conjugate functions as an enzyme substrate, and enzymatic hydrolysis disrupts the energy transfer. Alternatively, the conjugated substance is itself a fluorescent or nonfluorescent dye, optionally an additional dye of the present invention, that forms a labeling complex that exhibits a large Stokes shift due to internal energy-transfer (as described in U.S. Pat. No. 6,008,373). In another embodiment of the invention, the energy-transfer pair that incorporates a dye of the invention is conjugated to an oligonucleotide that displays efficient fluorescence quenching in its hairpin conformation (the so-called "molecular beacons" of Tyagi et al., *Nature Biotechnology,* 16:49 (1998)) or fluorescence energy transfer.

The preparation of dye conjugates using reactive dyes is well documented, e.g., by R. Haugland, Molecular Probes Handbook Of Fluorescent Probes And Research Chemicals, Chap. 1-3 (1996); and Brinkley, *Bioconjugate Chem.,* 3, 2 (1992). Conjugates typically result from mixing appropriate reactive dyes and the substance to be conjugated in a suitable solvent in which both are soluble. The dyes of the invention may be readily soluble in aqueous solutions, facilitating conjugation reactions with most biological materials. For reactive dyes that are photoactivated, conjugation requires illumination of the reaction mixture to activate the reactive dye.

Labeled members of a specific binding pair are typically used as fluorescent probes for the complementary member of that specific binding pair, each specific binding pair member having an area on the surface or in a cavity that specifically binds to and is complementary with a particular spatial and polar organization of the other. Exemplary specific binding pair members are proteins that bind non-covalently to low molecular weight ligands, such as biotin, drug-haptens and fluorescent dyes (such as an anti-fluorescein antibody). Representative specific binding pairs are shown in Table 2.

TABLE 2

Representative Specific Binding Pairs

| antigen | antibody |
|---|---|
| biotin | avidin (or streptavidin or anti biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |
| psoralen | nucleic acid |
| target molecule | RNA or DNA aptamer |

*IgG is an immunoglobulin
†aDNA and aRNA are the antisense (complementary) strands used for hybridization General Preparatory Methods Dyes and dye conjugates, for example, the compounds described herein, permit the detection of a molecule of interest in a complex mixture after reaction with a reactive group $R^x$. The reactive group may be added to the corresponding precursor of Formula I or Formula II by the synthetic techniques described herein, or by techniques well known to those of skill in the art. For instance, the attachment of reactive groups onto a core molecule can be accomplished by several types of chemical modification. See Greg T. Hermanson, *Bioconjugate Techniques,* Academic Press, San Diego, Calif. (1996). Additional information regarding general synthetic methods that may be used to prepare the compounds described herein may be found in March's *Advanced Organic Chemistry Reactions, Mechanisms, and Structure,* $5^{th}$ Ed. by Michael B. Smith and Jerry March, John Wiley & Sons, Publishers (2001); and Wuts et al., *Protective Groups in Organic Synthesis,* $3^{rd}$ Ed., John Wiley & Sons, Publishers (1999).

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing Linking Groups The general methods for forming a reactive group at the end of a linking group L to form a compound of Formula I or II are well known in the art. Such transformations, e.g., the 'linking' or 'coupling' reactions, are standard techniques. Techniques used to couple various $R^x$ groups to linking groups can be found in standard handbooks such as Hermanson's *Bioconjugate Techniques*. Of course, one skilled in the are would recognize that compounds of Formula I and II can be prepared by not only a reaction between an appropriate $R^x$ and the corresponding Formula-L but also by a reaction between an -L-$R^x$ group with an appropriately functionalized Formula I or II precursor, for example, one with an appropriate electrophile or nucleophile. A primary hydroxyl group on a linking group can be converted to a leaving group, such as a toluenesulfonyl group, which group can then be displaced with a nucleophile, for example, a deprotonated 6'-hydroxycyanobenzothiazole. For example, specific examples of forming cyanobenzothiazole-linker groups are described by Zhou (see *J. Amer. Chem. Soc.* 2006, 128(10), 3122).

One skilled in the art will readily recognize that there are numerous ways to provide the linking group L of the group -L-R$^x$. For example, a linking group that includes a carbamate (urethane) group can be link together two alkyl groups, or an alkyl group and a polyethylene glycol group (e.g., one with two to about 6 repeating units). The terminal hydroxyl group of an L group precursor can be converted to a reactive p-nitrophenyl carbonate, followed by the addition of an amine, to provide the urethane. Other methods are also well known. For example, an alcohol could be treated with 1,1'-carbonyldiimidazole to provide an imidazolide, followed by addition of an amine. The amine can be, for example, a sulfonic acid sodium salt linked to the amine through an organic group. An alcohol can also be treated with phosgene or a phosgene equivalent (e.g., diphosgene or triphosgene) to provide a chloroformate, followed by addition of an amine. Alternatively, an alcohol can be combined with a carbamoyl chloride to afford the urethane. One skilled in the art will readily recognize that there are numerous variations that can provide other linking groups that include groups such as amides, esters, ethers, and amines.

Numerous succinimidyl esters that are useful for preparing -L-R$^x$ groups are commercially available, for example, from Invitrogen Corporation. Additionally, one skilled in the art can use commercially available reagents and well known conditions for preparing succinimidyl esters to provide portions of the linking group moiety -A-B-Z-, as well as -L-R$^x$ groups. Hermanson's *Bioconjugate Techniques* provides an extensive description of coupling reactions and synthetic transformations that can be used to prepare -L-R$^x$ groups, particularly in Part I, which describes "Functional Targets" and "The Chemistry of Reactive Groups" (pages 1-416). For example, common reagents used to prepare succinimidyl esters include N-hydroxysuccinimide ("NHS", *J. Am. Chem. Soc.*, 86:1839 (1964)) and a carbodiimide activating agent such as dicyclohexyl-carbodiimide ("DCC") or 1,3-dimethylaminoproply-ethylcarbodiimide ("EDC"; *J. Am. Chem. Soc.*, 95:875 (1973)). Alternatively, a 'self-activating' NHS derivative can be used, such as N-trifluoroacetyl-succinimide ("TFA-NHS"), N,N-disuccinimidyl carbonate (*Tetrahedron Lett.*, 22:4817 (1981)), or O—(N-succinimidyl)-N,N,N',N'-bis(tetramethylene)uranium hexafluorophosphate. Depending on the reactivity and solubility of the benzothiazole or linking group being activated, the conditions can range from organic to aqueous solvents. For example, a suitable organic solvent can be dimethylformamide ("DMF"). These reactions can be run in the presence of a base, such as a hindered amine base, for example, triethylamine or diethylisopropylamine, whereas aqueous conditions may include adjusting the pH to a range from about 6.5 to about 8.5.

When a linking group L contains an amine, for example, when B of the -A-B-Z- group is —NH—, a succinimidyl ester of such a group can be used in a reaction to form the remaining portion of L. When the group -A- or -A-B- terminates in an acid, the acid can be converted to a succinimidyl ester and combined with an amine-terminated —Z—, —Z—R$^x$, or —R$^x$ group. Other activating groups, such as sulfosuccinimidyl esters, tetrafluorophenyl esters, sulfodichlorophenol esters, isothiocyanates, sulfonyl chlorides, dichlorotriazines, aryl halides, or acyl azides can be used in place of succinimidyl esters, for example, to link with amines. One skilled in the art can readily convert various organic moieties to suitable amines or acids using standard transformations, including oxidations, reductions, and displacement reactions. Furthermore, protecting groups can be used to simplify the preparation of certain compounds of Formula I or II. The use of protecting groups is well known in the art (see for example, see for example, Greene, *Protecting Groups In Organic Synthesis*; Wiley: New York, 1981).

Preparation of Compounds of the Invention

Several methods exist for the preparation of cyanines. The method used to prepare the compounds described herein involves the preparation of a tricyclic indolium derivative (the "A" ring system or the "B" ring system, followed by linking the two tricyclic ring systems together through a bridge, such as a methine or polymethine bridge. Such techniques are well known in the art and relevant techniques have been described in U.S. Pat. Nos. 5,321,130 (Yue et al.); 5,658,751 (Yue et al.); 6,492,102 B1 (Kagawa et al.); 6,974,873 B2 (Leung et al.); 6,977,305 (Leung et al.); and U.S. Publication Nos. 20060239922 (Cooper et al.); and 2002/0106593 (Kagawa et al.); which are incorporated herein by reference.

The A ring system and the B ring system can be the same or different. The can also be modified to include side chains and/or substituents, for example, -L-R$^x$ groups, before or after being linked by a bridge. Various A and B ring systems that can be used to prepare the compounds of the invention are illustrated in FIGS. 1 and 2. Once the two ring systems have been linked the R$^x$ group can be optionally further modified, for example, to convert a hydroxyl group, an amine group, or a carboxyl group to a desired reactive group (e.g., a different R$^x$ group such as an activated ester, a 4-cyanobenzothiazole, or a haloalkane).

Compounds of the invention can be prepared as follows, or by analogous routes that would be readily understood by one of skill in the art. As illustrated in Scheme 1, 1,2,3,4-tetrahydroquinoline or a derivative thereof can be nitrated and reduced to provide 3,4-dihydroquinolin-1(2H)-amine or a corresponding derivative thereof, Intermediate A. The compound 1,2,3,4-tetrahydroquinoline, and many derivatives thereof, are commercially available from suppliers such as Aldrich Chemical Co. (Milwaukee, Wis.).

Scheme 1. Preparation of Dihydroquinolin Derivatives

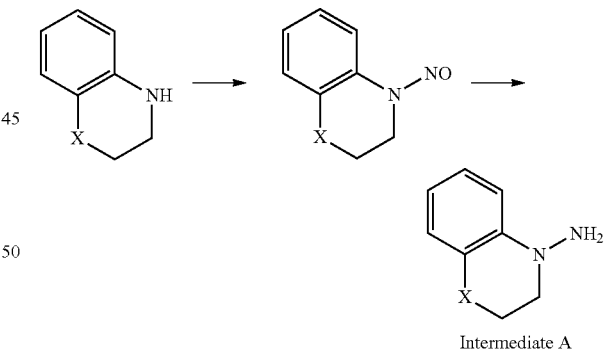

Intermediate A where X is CH$_2$, (CH$_2$)$_2$, (CH$_2$)$_3$, NH, O, or S.

Intermediate A can be converted to a tricyclic indolinium derivative by reacting the intermediate with a branched ketone, such as 3-methyl-2-butanone, or a branched keto carboxylic acid, such 7-methyl-8-oxanonanoic acid. Of course, any suitable length ketone or carboxylic acid and alkyl substituents other than methyl can be employed to provide a variety of derivatives. See for example, the intermediates illustrated in FIGS. 1 and 2. The resulting compounds can be sulfonated by treatment with sulfuric acid. Examples of such tricyclic indolium derivatives and their corresponding sulfonated derivatives are shown in Scheme 2.

Scheme 2.
Tricyclic Indolium Compounds and Sulfonated Derivatives Thereof

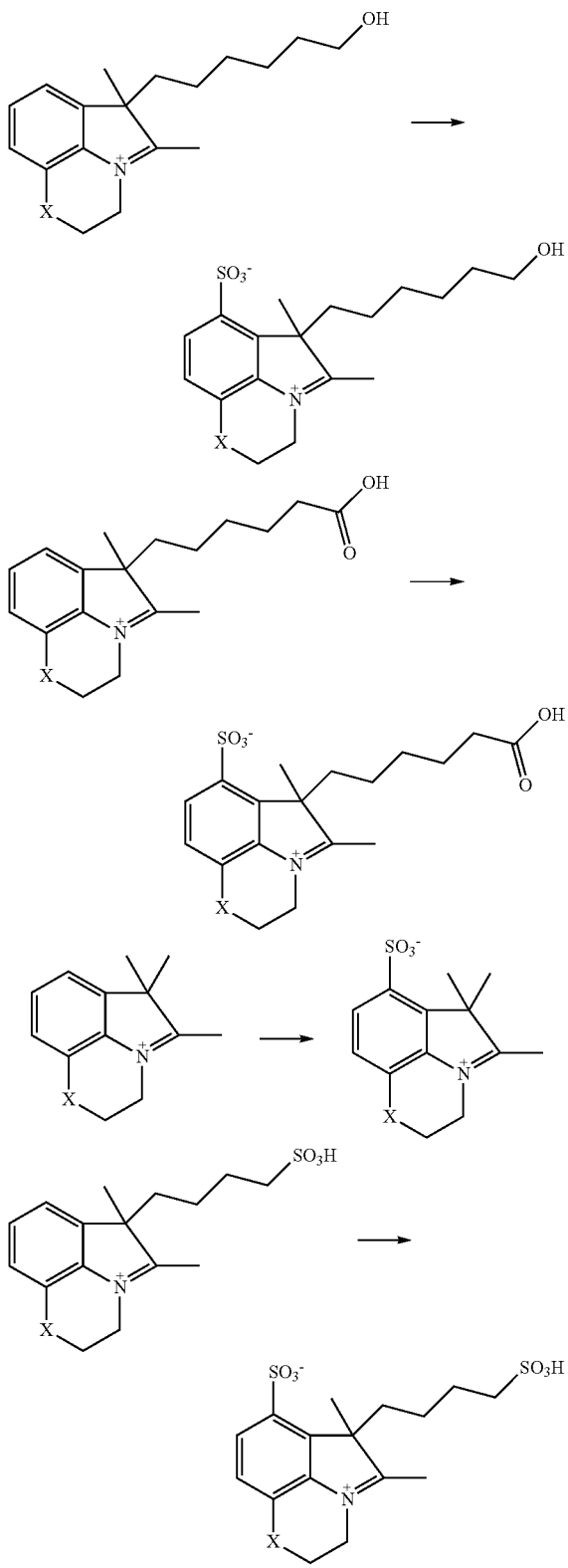

where X is $CH_2$, $(CH_2)_2$, $(CH_2)_3$, NH, O, or S.

Tetracyclic intermediates can be prepared by analogous procedures. By starting with 1,2,3,4-tetrahydrobenzo[f]quinoline or a derivative thereof, the corresponding 2,3-dihydrobenzo[f]quinolin-4(1H)-amine, or derivative thereof, can be obtained, as illustrated in Scheme 3.

Scheme 3. Preparation of Dihydrobenzo[f]quinolin Derivatives

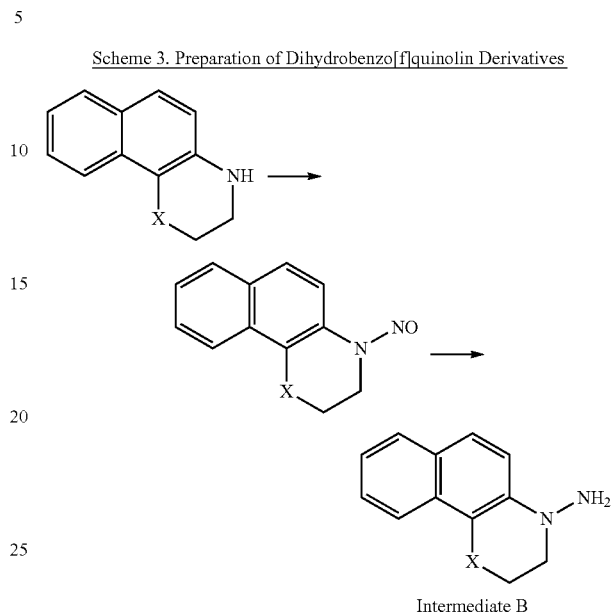

Intermediate B where X is $CH_2$, $(CH_2)_2$, $(CH_2)_3$, NH, O, or S.

Intermediate B can then be converted to the tetracyclic benzo[f]indolium as described for the conversion of Intermediate A to the tricyclic indolinium derivatives Examples of tetracyclic indolium derivatives and their corresponding sulfonated derivatives are shown in Scheme 4.

Scheme 4.
Tetracyclic Benzo[f]indolium Salts and Sulfonated Derivatives Thereof

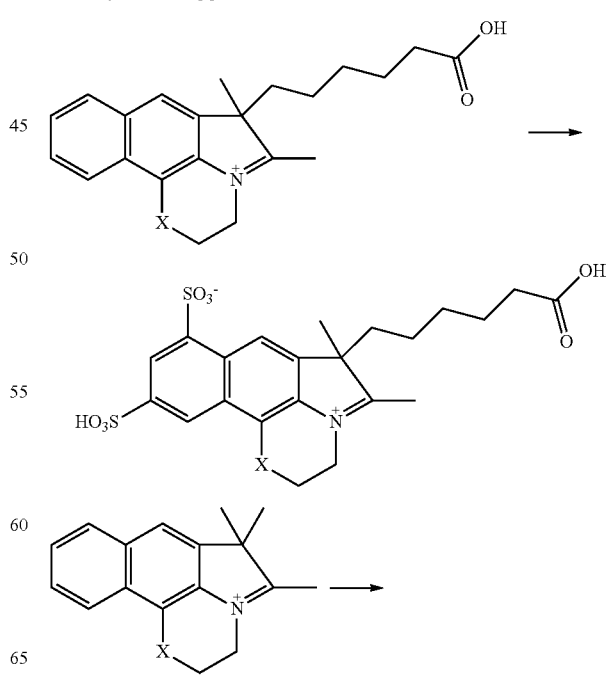

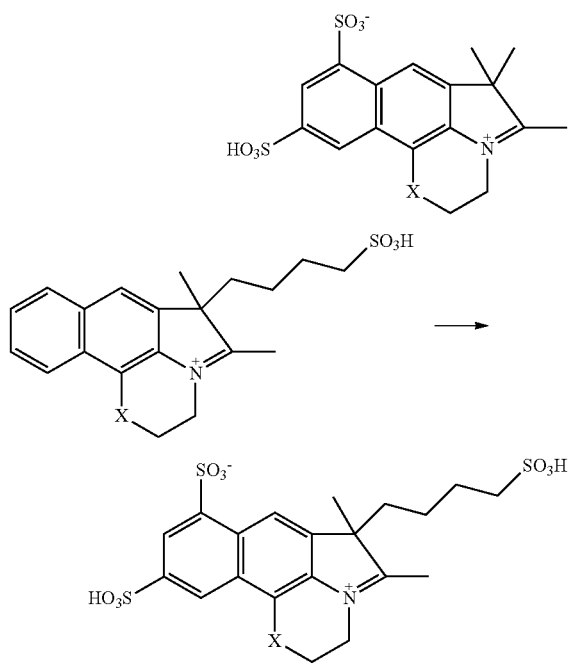

where X is CH$_2$, (CH$_2$)$_2$, (CH$_2$)$_3$, N, O, or S.

In a similar manner, benzo[e]indolium derivatives can be prepared from 1,2,3,4-tetrahydrobenzo[g]quinoline or a suitable derivative to provide 3,4-dihydrobenzo[g]quinolin-1(2H)-amine or the corresponding derivative, Intermediate C, illustrated in Scheme 5.

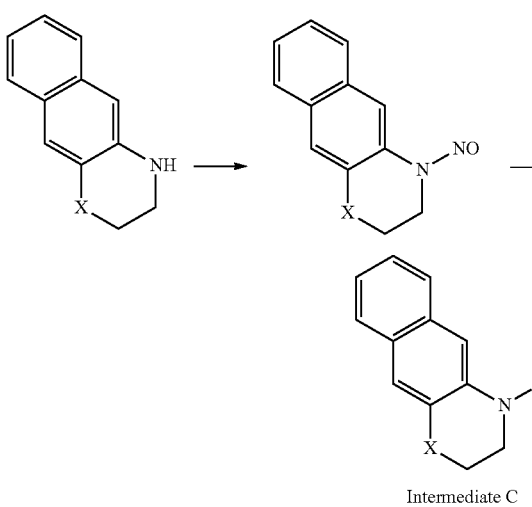

Scheme 5. Preparation of Dihydrobenzo[g]quinolin Derivatives

Intermediate C wherein X is CH$_2$, (CH$_2$)$_2$, (CH$_2$)$_3$, N, O$_5$ or S.

Intermediate C can then be converted to the tetracyclic benzo[e]indolium as described for the conversion of Intermediate A to the tricyclic indolinium derivatives Examples of such tetracyclic indolium derivatives and their corresponding sulfonated derivatives are shown in Scheme 6.

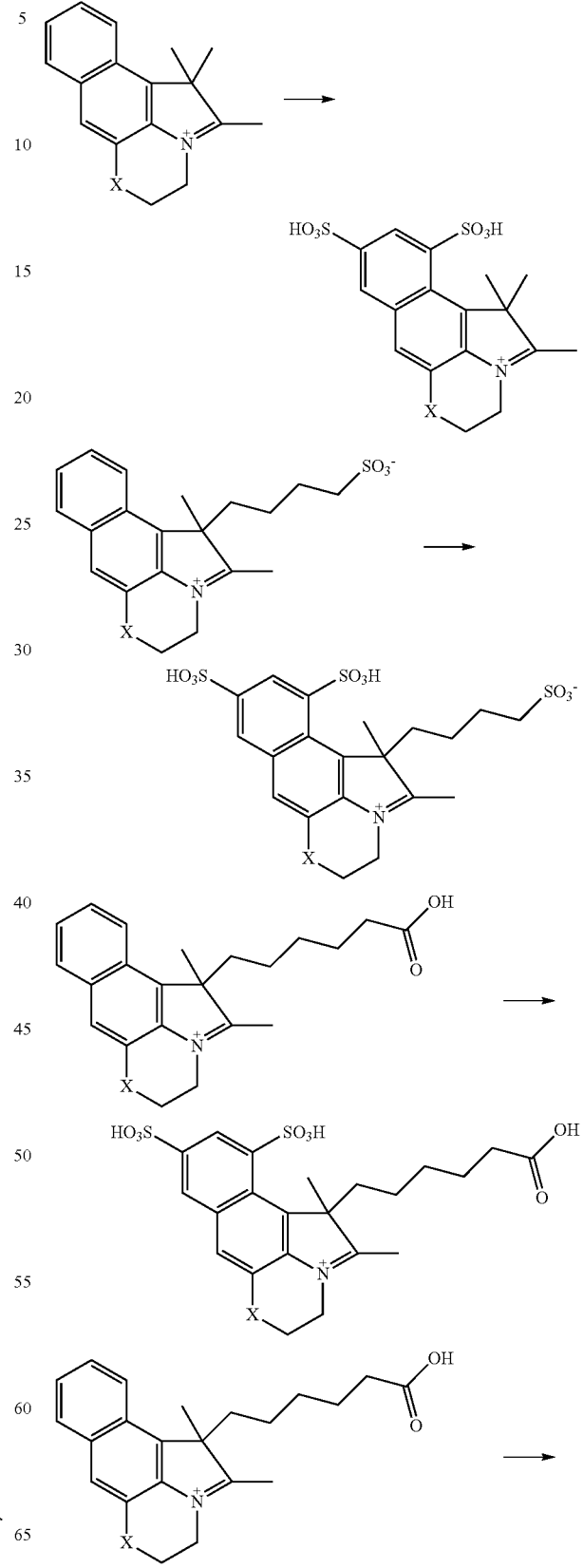

Scheme 6.
Tetracyclic Benzo[e]indolium Salts and Sulfonated Derivatives Thereof

-continued

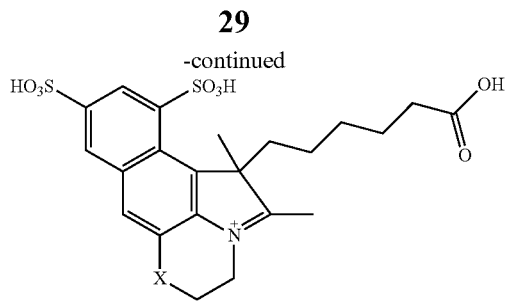

where X is $CH_2$, $(CH_2)_2$, $(CH_2)_3$, NH, O, or S.

For each compound above, fluorinated derivatives can also be prepared by selection of appropriate starting materials. A variety of fluorinated tricyclic and tetracyclic compounds of the invention can be prepared as illustrated in Scheme 7.

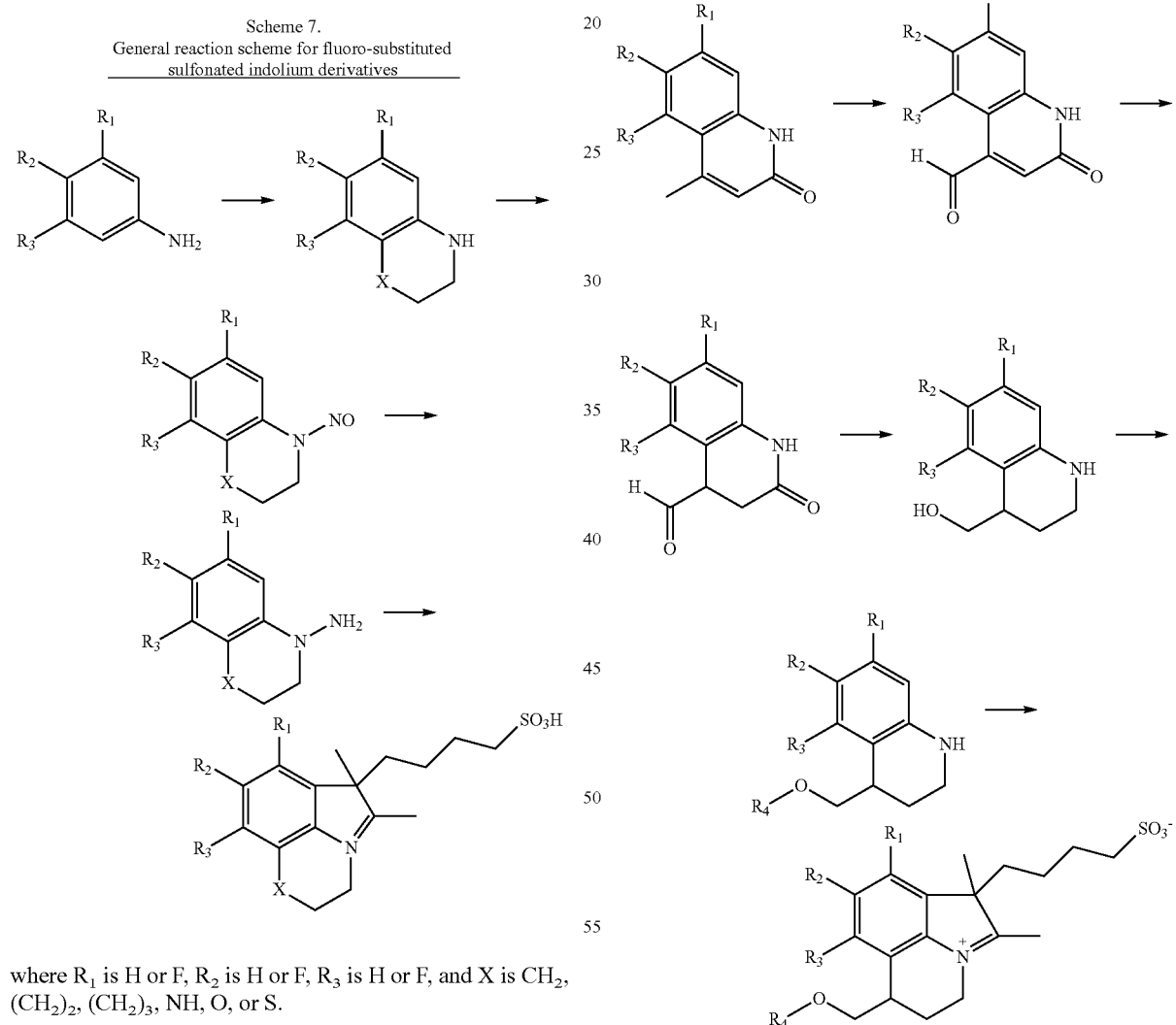

where $R_1$ is H or F, $R_2$ is H or F, $R_3$ is H or F, and X is $CH_2$, $(CH_2)_2$, $(CH_2)_3$, NH, O, or S.

Specific examples include compounds where $R_1$ is F, $R_2$ is H, and $R_3$ is H; where $R_1$ is H, $R_2$ is F, and $R_3$ is H; where $R_1$ is F, $R_2$ is F, and $R_3$ is H; where $R_1$ is F, $R_2$ is F, and $R_3$ is F; and where $R_1$ is F, $R_2$ is H, and $R_3$ is F. Each of these compounds can be converted to the corresponding compounds where X is $CH_2$, $(CH_2)_2$, $(CH_2)_3$, N, O, or S.

Rings of the indolium derivatives can also be substituted as illustrated in Scheme 8.

where $R_1$, $R_2$, and $R_3$ are as defined in Scheme 7 or as defined for Formula I, and $R_4$ is $(CH_2)_xCO_2H$ or $(CH_2)_xOH$, where x is 1 to about 12.

The tricyclic (or tetracyclic) ring systems A and B can then be linked together to provide dyes of the invention, and intermediates thereof. A variety of indolium derivative dyes can be prepared as illustrated below in Schemes 9-11.

Scheme 9.
General reaction scheme for preparation of dyes from indolium derivatives

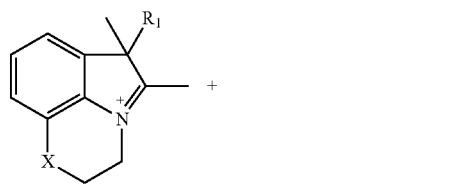

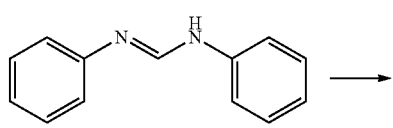

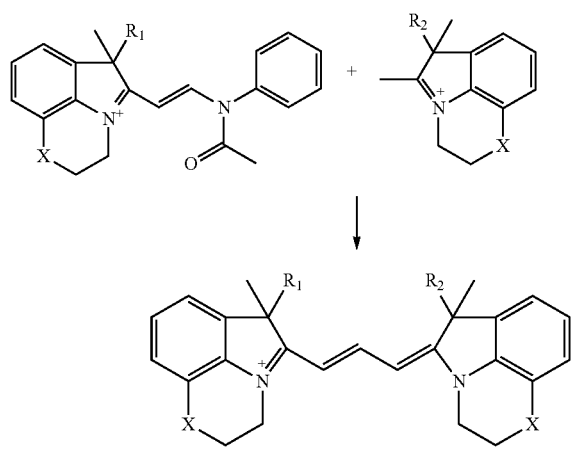

R₁ = CH₃, (CH₂)₄SO₃H, (CH₂)₆OH, (CH₂)₅CO₂H
R₂ = (CH₂)₆OH, (CH₂)₅CO₂H
X = CH₂, (CH₂)₂, (CH₂)₃, N, O, S

Scheme 10.
General reaction scheme for preparation of dyes from indolium derivatives

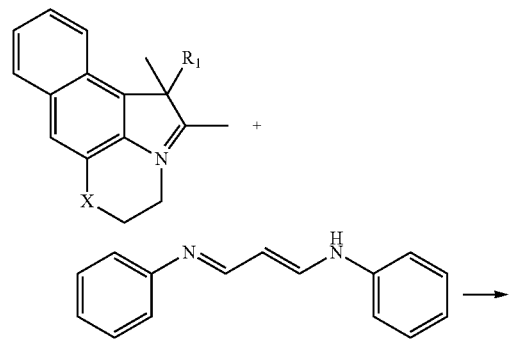

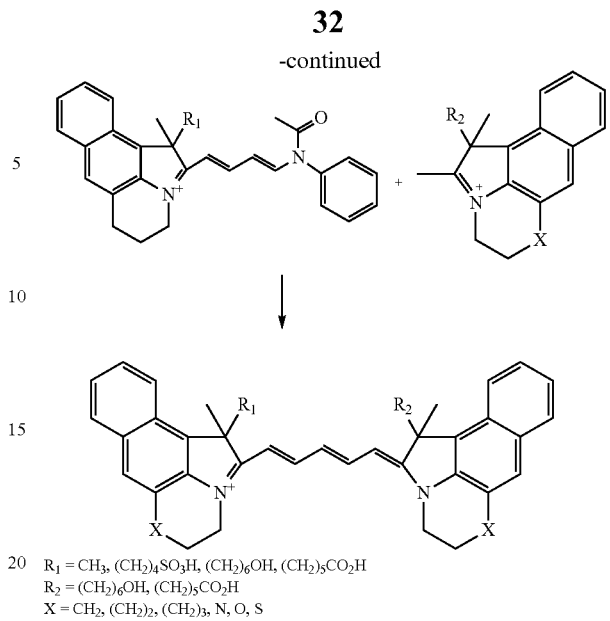

R₁ = CH₃, (CH₂)₄SO₃H, (CH₂)₆OH, (CH₂)₅CO₂H
R₂ = (CH₂)₆OH, (CH₂)₅CO₂H
X = CH₂, (CH₂)₂, (CH₂)₃, N, O, S

Scheme 11.
General reaction scheme for preparation of dyes from indolium derivatives

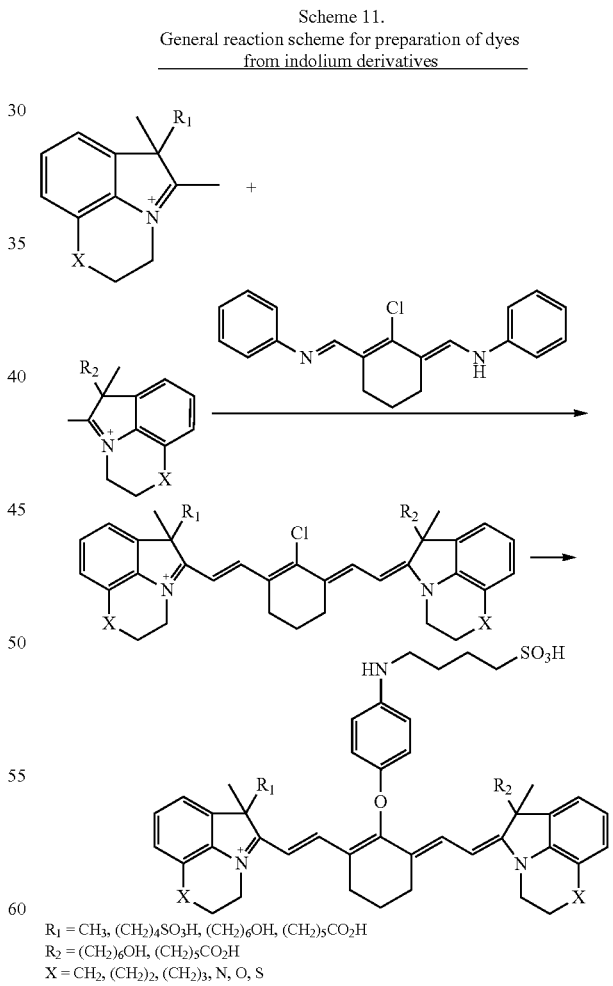

R₁ = CH₃, (CH₂)₄SO₃H, (CH₂)₆OH, (CH₂)₅CO₂H
R₂ = (CH₂)₆OH, (CH₂)₅CO₂H
X = CH₂, (CH₂)₂, (CH₂)₃, N, O, S

The functional groups of R₁ and R₂ can then be converted by standard synthetic transformations to other reactive groups $R^x$, such as activated esters of carboxylic acids, amines, sulfonyl halides, mercaptans, boronates, boronate esters, phosphoramidites, isocyanates, haloacetamides, aldehydes, azides, acyl nitriles, photoactivatable groups, O- or N-linked 4-cyanobenzothiazoles, $(C_1-C_8)$alkylhalides, or a sulfo groups. Dyes of the invention can be modified to include reactive groups that can be substrates for an enzyme, such as a halo alkyl group, for example, as illustrated in Scheme 12.

Dyes of the invention can also be modified to include 4-cyanobenzothiazole moieties, for example, as illustrated in Scheme 13.

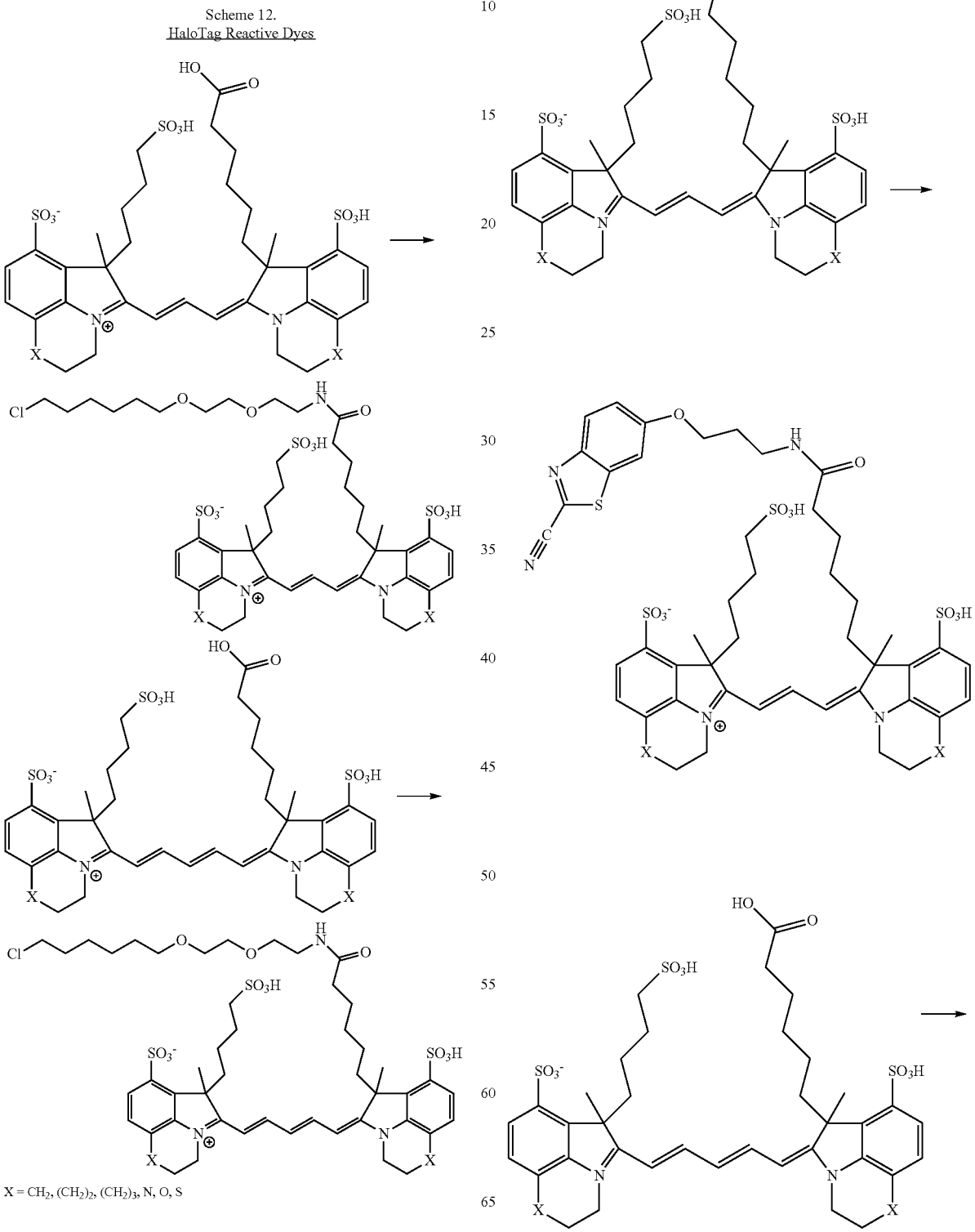

-continued

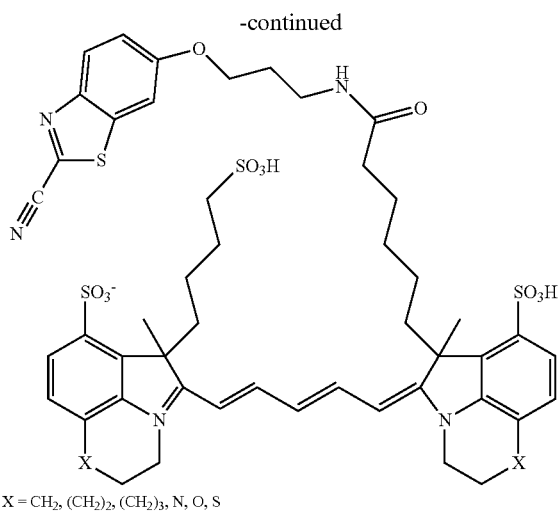

X = CH$_2$, (CH$_2$)$_2$, (CH$_2$)$_3$, N, O, S

By employing other tricyclic intermediates, such as those illustrated in FIGS. 1 and 2, numerous other examples of the compounds of the invention can be prepared, using the corresponding synthetic methods.

Methods of Use

In one aspect of the invention, the dye conjugates of the invention are used to label a sample so that the sample can be identified or quantitated. For instance, such conjugates may be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen. In one embodiment, dye conjugate is used to label a sample that comprises a ligand for which the conjugated substance is a complementary member of a specific binding pair (e.g., see Table 2).

The sample may be obtained directly from biological materials, e.g., a wash from a solid material (organic or inorganic), a growth medium in which cells have been cultured, or a buffer solution in which cells have been placed for evaluation, or physiological sources. When the sample comprises cells, the cells are optionally single cells, including microorganisms, or multiple cells associated with other cells in two or three dimensions, including multicellular organisms, embryos, tissues, biopsies, filaments, biofilms, and the like.

Alternatively, the sample is a solid, optionally a smear or scrape or a retentate removed from a liquid or vapor by filtration. In one aspect of the invention, the sample is obtained from a biological fluid, including separated or unfiltered physiological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g., the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The dye conjugates are generally utilized by combining the conjugate as described above with the sample of interest under conditions selected to yield a detectable optical response. The sample is then illuminated at a wavelength selected to elicit the optical response. Typically, a specified characteristic of the sample is determined by comparing the optical response with a standard or expected response.

A detectable optical response means a change in, or occurrence of, an optical signal that is detectable either by observation or instrumentally. Typically, the detectable response is a change in fluorescence, such as a change in the intensity, excitation or emission wavelength distribution of fluorescence, fluorescence lifetime, fluorescence polarization, or a combination thereof. The degree and/or location of the labeling, compared with a standard or expected response, indicates whether, and to what degree, the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye conjugates are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration may be determined by systematic variation until satisfactory results with minimal background fluorescence is accomplished.

The dye conjugates may be used to label samples with biological components. The sample may comprise heterogeneous mixtures of components (including intact cells, cell extracts, bacteria, viruses, organelles, and mixtures thereof), or a single component or homogeneous group of components (e.g., natural or synthetic amino acid, nucleic acid or carbohydrate polymers, or lipid membrane complexes). The dyes are generally non-toxic to living cells and other biological components, within the concentrations of use.

The dye conjugate is combined with the sample in any way that facilitates contact between the dye conjugate and the sample components of interest. Typically, the dye conjugate or a solution containing the dye conjugate is simply added to the sample. Certain dyes of the invention, e.g., those that are substituted by one or more sulfonic acid moieties, may be less permeant to membranes of biological cells, but once inside viable cells are typically well retained. Treatments that permeabilize the plasma membrane, such as electroporation, shock treatments or high extracellular ATP, may be used to introduce selected dye conjugates into cells. Alternatively, selected dye conjugates can be physically inserted into cells, e.g., by pressure microinjection, scrape loading, patch clamp methods, or phagocytosis.

Dyes that incorporate an aliphatic amine or a hydrazine residue may be microinjected into cells, where they can be fixed in place by aldehyde fixatives such as formaldehyde or glutaraldehyde. This property makes such dyes useful for intracellular applications such as neuronal tracing.

Dyes that possess a lipophilic substituent, such as phospholipids, may non-covalently incorporate into lipid assemblies, e.g., for use as probes for membrane structure, or for incorporation in liposomes, lipoproteins, films, plastics, lipophilic microspheres or similar materials; or for tracing. Lipophilic dyes are useful as fluorescent probes of membrane structure.

Chemically reactive dye compounds may covalently attach to a corresponding functional group on a wide variety of materials, forming dye conjugates as described above. Using dye compounds to label reactive sites on the surface of cells, in cell membranes or in intracellular compartments such as organelles, or in the cytoplasm, permits the determination of their presence or quantity, accessibility, or their spatial and temporal distribution in the sample. Photoreactive dyes may be used similarly to photolabel components of the outer membrane of biological cells or as photo-fixable polar tracers for cells.

Optionally, the sample is washed after labeling to remove residual, excess or unbound dye compound or dye conjugate. The sample is optionally combined with one or more other solutions in the course of labeling, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. When the additional detection reagent has, or yields a product with, spectral properties that differ from those of the subject dye compounds, multi-color applications are possible. This is particularly useful where the additional detection reagent is a dye or dye conjugate having spectral properties that are detectably distinct from those of the labeling dye.

The dye conjugates are used according to methods known in the art; e.g., use of antibody conjugates in microscopy and immunofluorescent assays; and nucleotide or oligonucleotide conjugates for nucleic acid hybridization assays, nucleic acid amplification reactions, and nucleic acid sequencing (e.g., U.S. Pat. Nos. 5,332,666, 5,171,534, and 4,997,928, and WO 94/05688). Dye conjugates of multiple independent dyes of the invention possess utility for multi-color applications.

At any time after or during labeling, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Exemplary Methods of Use

In one embodiment, a dye oligonucleotide conjugate of the present invention is combined with a sample that contains or is thought to contain a nucleic acid polymer, incubating the mixture of dye oligonucleotide conjugate and sample for a time sufficient for the oligonucleotide in the conjugate to combine with nucleic acid polymers in the sample to form nucleic acid hybrids (complexes) (the dye oligonucleotide conjugate is a probe), or to prime nucleic acid synthesis (the dye oligonucleotide conjugate is a primer), which may be detected. The characteristics of the labeled molecules, including the presence, location, intensity, excitation and emission spectra, fluorescence polarization, fluorescence lifetime, and other physical properties of the fluorescent signal can be used to detect, differentiate, sort, quantitate, and/or analyze aspects or portions of the sample. The dye conjugates of the invention are optionally used in conjunction with one or more additional reagents (e.g., detectably different fluorescent reagents), including dyes of the same class having different spectral properties.

Typically, the dye conjugate is prepared for use by dissolving the dye conjugate in an aqueous or aqueous miscible solution that is compatible with the sample and the intended use. For biological samples, where minimal perturbation of cell morphology or physiology is desired, the solution is selected accordingly. High concentrations of organic solvents, cations, and oxidizing agents may reduce fluorescence, as does the ionic detergent sodium dodecyl sulfate (SDS) at concentrations >0.01%. A number of labeling solution additives, however, may not interfere with the fluorescence of the dye-nucleic acid complex (e.g., urea up to 8M; CsCl up to 1 g/mL; formamide up to 50% of the solution; and sucrose up to 40%). The dyes may have greater stability in buffered solutions than in water alone; and agents that reduce the levels of free oxygen radicals, such as $\beta$-mercaptoethanol, may contribute to the stability of the dyes.

The labeling solution is made by dissolving the dye conjugate directly in an aqueous solvent such as water, a buffer solution, such as buffered saline (preferably non-phosphate for some viability discrimination applications), a Tris(hydroxymethyl)aminomethane (TRIS) buffer (preferably containing EDTA), or a water-miscible organic solvent such as dimethylsulfoxide (DMSO), dimethylformamide (DMF), or a lower alcohol such as methanol or ethanol. The dye conjugate is usually preliminarily dissolved in an organic solvent (e.g., 100% DMSO) at a concentration of greater than about 100 times that used in the labeling solution, then diluted one or more times with an aqueous solvent such as water or buffer, such that the dye conjugate is present in an effective amount.

Typically labeling solutions for cellular samples have a dye concentration greater than 0.1 nM and less than 50 $\mu$M, more typically greater than 1 nM and less than 10 $\mu$M, e.g., between 0.5 and 5 $\mu$M. Labeling solutions for electrophoretic gels typically have a dye concentration of greater than 0.1 $\mu$M and less than 10 $\mu$M, more typically about 0.5 to 2 $\mu$M; the same holds true where the dye is added to the gel (pre-cast) before being combined with nucleic adds. Labeling solutions for detection and quantitation of free nucleic acids in solution typically have a concentration of 0.1 $\mu$M to 2 $\mu$M. The optimal concentration and composition of the labeling solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures.

The nucleic acid in the sample may be DNA or RNA, or a mixture or a hybrid thereof. Any DNA is optionally single-, double-, triple-, or quadruple-stranded DNA; any RNA is optionally single stranded ("ss") or double stranded ("ds"). The nucleic acid may be a natural polymer (biological in origin) or a synthetic polymer (modified or prepared artificially). The nucleic acid polymer (for instance, one containing at least 8 bases or base pairs) may be present as nucleic acid fragments, oligonucleotides, or larger nucleic acid polymers with secondary or tertiary structure. The nucleic acid is optionally present in a condensed phase, such as a chromosome. The nucleic acid polymer optionally contains one or more modified bases or links or contains labels that are non-covalently or covalently attached. For example, the modified base can be a naturally occurring modified base such as Ψ (pseudouridine) in tRNA, 5-methylcytosine, 6-methylaminopurine, 6-dimethylaminopurine, 1-methylguanine, 2-methylamino-6-hydroxypurine, 2-dimethylamino-6-hydroxypurine, or other known minor bases (see, e.g., Davidson, The Biochemistry Of The Nucleic Acids (1976)) or is synthetically altered to contain an unusual linker such as morpholine derivatized phosphates (AntiVirals, Inc., Corvallis, Oreg.), or peptide nucleic acids such as N-(2-aminoethyl)glycine units (Wittung et al., Nature, 368:561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide (e.g., CHROMATIDE™ labeled nucleotides, Molecular Probes, Eugene, Oreg.) or on the 3' or 5' end of the polymer, or ligands non-covalently attached to the nucleic acids. The sensitivity of the dyes for polymers containing primarily modified bases and links may be diminished by interference with the binding mode. Some embodiments of the dyes may inhibit non-specific nuclease activity but not restriction endonuclease activity at certain dye:base pair ratios.

The sample that contains the nucleic acid is optionally a biological structure (i.e., an organism or a discrete unit of an organism), or a solution (including solutions that contain biological structures), or a solid or semi-solid material. Consequently, the nucleic acid is optionally free in solution, immobilized in or on a solid or semi-solid material, extracted from a biological structure (e.g., from lysed cells, tissues, organisms or organelles), or remains enclosed within a biological structure. In order for the nucleic acids to bind to the dyes, it is necessary that the nucleic acids be in an aqueous environment to contact the dye, even if the nucleic acids are not enclosed in a biological structure.

The biological structure that encloses the nucleic acid is optionally a cell or tissue, for example where the nucleic acid is present in a cell or interstitial space as a prokaryote or eukaryote microorganism, or as a virus, viroid, chromosome or organelle. Alternatively, the biological structure is not enclosed in a tissue or cell and is present either as a virus or as a microorganism or other cell, or is present as a cellular component removed from its parent cell (e.g., a plasmid or chromosome, or a mitochondrion or nucleus or other organelle). Typically, the biological structure is an organelle, chromosome or cell that is optionally inside a eukaryote cell. The cell that is present inside a eukaryote cell is typically a parasite or other infectious agent such as a bacterium, protozoa, mycoplasma or mycobacterium. When the nucleic acid is contained in a biological structure that is a cell, the cells are viable or dead cells or a mixture thereof, i.e., the integrity of the cell membrane is optionally intact or disrupted by natural (autolytic), mechanical or chemical means or by environmental means such as changes in temperature or pressure. Alternatively, the cells are blebbing or undergoing apoptosis or in a cycle of growth or cell division.

When the nucleic acid is present in a solution, the sample solution can vary from one of purified or synthetic nucleic acids such as oligonucleotides to crude mixtures such as cell extracts or homogenates or other biological fluids, or dilute solutions from biological, industrial, or environmental sources. In some cases it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques, using a variety of supports or solutions or in a flowing stream. Alternatively, mixtures of nucleic acids may be treated with RNase or DNase so that the polymer that is not degraded in the presence of the nuclease can be discriminated from degradation products using the subject dyes.

For most applications, dyes are selected to give a quantum yield greater than about 0.3, preferably greater than 0.6, when bound to nucleic acid; for example, the dyes have a quantum yield <0.01 when not bound to nucleic acid, and a fluorescence enhancement greater than about 200 fold, e.g., greater than 1000 fold. When the fluorescence of the dye-nucleic acid complex is detected utilizing sustained high intensity illumination (e.g., microscopy), dyes with rate of photobleaching lower than commonly used dyes (e.g., fluorescein) may be employed, particularly for use in live cells. The relatively low toxicity of the dyes to living systems generally enables the examination of nucleic acids in living samples with little or no perturbation caused by the dye itself. For use with intact cells or samples in a gel, more permeant dyes may be employed, although some cells readily take up dyes that are shown to be impermeant to other cells by means other than passive diffusion across cell-membranes, e.g., by phagocytosis or other types of ingestion. Dyes that rapidly and readily penetrate cells do not necessarily rapidly penetrate gels. In applications where the nucleic acids are on a gel, the dye may also be selected to have a high binding affinity (such as $K_d > 10^{-6}$ M); whereas in applications where the nucleic acid is prelabeled prior to undergoing a separation step, such as gel or capillary electrophoresis, even a dye with higher binding affinity (such as $K_d > 10^{-8}$ M) may be employed to ensure good separation. When labeling nucleic acids in solution, high binding affinity may translate into greater sensitivity to small amounts of nucleic acid, but dyes with a moderate binding affinity (for instance, $10^{-6}$ M$<K_d<10^{-8}$ M) may be more effective over a greater dynamic range. The photostability, toxicity, binding affinity, quantum yield, and fluorescence enhancement of dyes are determined according to standard methods known in the art.

In one embodiment, a dye oligonucleotide conjugate is employed in methods and kits to detect alleles in a physiological sample at more than one loci. In one embodiment, an appropriate set of loci, primers, and amplification protocols is selected to generate amplified alleles from multiple co-amplified loci which, in one embodiment, do not overlap in size or which are labeled in a way which enables one to differentiate between the alleles from different loci which overlap in size. In addition, this method contemplates the selection of short tandem repeat (STR) loci which are compatible for use with a single amplification protocol. Successful combinations can be generated by trial and error of locus combinations, by selection of primer pair sequences, and by adjustment of primer concentrations to identify an equilibrium in which all included loci may be amplified. The number of loci which may be amplified in a multiplex amplification reaction step may be from 2 to 50, or any integer between 2 and 50, so long as the reaction produces amplified alleles produced from each of the individual. In one embodiment, the amplified fragments are less than 500 bp in length.

Once a multiplex to detect one set of loci is developed, it may be used as a core to create multiplexes to detect other loci in addition to the first set. Exemplary loci for STR analysis are disclosed in U.S. Pat. No. 7,008,771, the disclosure of which is incorporated by reference herein. The loci selected for multiplex analysis generally share the following characteristics: (1) they produce sufficient amplification product to allow evaluation; (2) they generate few if any artifacts due to the addition (or lack of addition) of a base to the amplified alleles during the multiplex amplification step; (3) they generate few, if any, artifacts due to premature termination of amplification reactions by a polymerase; and (4) they produce little or no "trailing" bands of smaller molecular weight from consecutive single base deletions below a given authentic amplified allele. See, e.g., Schumm et al., Fourth International Symposium on Human Identification 1993, pp. 177-187 (published by Promega Corp., 1994).

Once a set of loci for co-amplification in a single multiplex reaction is identified, one can determine primers suitable for co-amplifying each locus in the set. Care should be used in selecting the sequence of primers used in the multiplex reaction. Inappropriate selection of primers can produce several undesirable effects such as lack of amplification, amplification at multiple sites, primer dimer formation, undesirable interaction of primer sequences from different loci, production of alleles from one locus which overlap with alleles from another, or the need for amplification conditions or protocols for the different loci which are incompatible in a multiplex. Primers are selected for use in multiplex systems by employing a re-iterative process of selecting primer sequences, mixing the primers for co-amplification of the selected loci, co-amplifying the loci, then separating and detecting the amplified products. Initially, this process often produces the amplified alleles in an imbalanced fashion (i.e., higher product yield for some loci than for others) and may also generate amplification products which do not represent the alleles themselves. To eliminate such extra fragments from the multiplex systems, individual primers from the total set may be used with primers from the same or other loci to identify which primers contribute to the amplification of the extra fragments. Once two primers which generate one or more of the fragments are identified, one or both contributors are modified and retested, either in a pair alone or in the multiplex system (or a subset of the multiplex system). This process is repeated until evaluation of the products yields amplified alleles with no or an acceptable level of extra fragments in the multiplex system. On occasion, extra fragments can be eliminated by labeling the opposite primer in a primer pair. This change reveals the products of the opposing primer in the detection step. This newly labeled primer may amplify the true alleles with greater fidelity than the previously labeled primer generating the true alleles as a greater proportion of the total amplification product.

The determination of primer concentration may be performed either before or after selection of the final primer sequences. Generally, increasing primer concentration for any particular locus increases the amount of product generated for that locus. However, this is also a re-iterative process because increasing yield for one locus may decrease it for one or more other loci. Furthermore, primers may interact directly affecting yield of the other loci. Linear increases in primer concentration do not necessarily produce linear increases in product yield for the corresponding locus.

Locus to locus balance is also affected by a number of parameters of the amplification protocol such as the amount of template used, the number of cycles of amplification, the annealing temperature of the thermal cycling protocol, and the inclusion or exclusion of an extra extension step at the end of the cycling process. Absolutely even balance across all alleles and loci is generally not achieved.

Synthesis of the primers used in the present method can be conducted using any standard procedure for oligonucleotide synthesis known to those skilled in the art. At least one primer for each locus is covalently attached to a different dye label.

Samples of genomic DNA can be prepared for use in the method of this invention using any method of DNA preparation which is compatible with the amplification of DNA. Many such methods are known by those skilled in the art. When the at least one DNA sample to be analyzed is human genomic DNA, the DNA may be prepared from tissue, selected from the group consisting of blood, semen, vaginal cells, hair, saliva, urine, bone, buccal samples, amniotic fluid containing placental cells or fetal cells, chorionic villus, and mixtures of any of the tissues listed above. Optionally, DNA concentrations can be measured prior to use in the method of the present invention, using any standard method of DNA quantification known to those skilled in the art. Use of too much template DNA in the amplification reactions can produce artifacts which appear as extra bands which do not represent true alleles.

Once a sample of genomic DNA is prepared, the targeted loci can be co-amplified in the multiplex amplification step. Any one of a number of different amplification methods can be used to amplify the loci, including, but not limited to, polymerase chain reaction (PCR), transcription based amplification and strand displacement amplification (SDA). In one embodiment, the DNA sample is subjected to PCR amplification using primer pairs specific to each locus in the set.

At least one primer for each locus can be covalently attached to a dye label, one of which comprises a dye of the present invention. The primers and dyes attached thereto are selected for use in the multiplex amplification reaction, such that alleles amplified using primers for each locus labeled with one color do not overlap with the alleles of the other loci in the set co-amplified therein using primers labeled with the same color, when the alleles are separated, e.g., by gel or capillary electrophoresis. Fluorescent labels suitable for attachment to primers for use in the present invention are commercially available. See, e.g. fluorescein and carboxy-tetramethylrhodamine labels and their chemical derivatives from PE Biosystems and Molecular Probes. In one embodiment, at least three different labels are used to label the different primers used in the multiplex amplification reaction. When a size marker is included to evaluate the multiplex reaction, the primers used to prepare the size marker may be labeled with a different label from the primers used to amplify the loci of interest in the reaction.

Once a set of amplified alleles is produced from the multiplex amplification step, the amplified alleles are evaluated. The evaluation step of this method can be accomplished by any one of a number of different means. Electrophoresis may be used to separate the products of the multiplex amplification reaction, e.g., capillary electrophoresis or denaturing polyacrylamide gel electrophoresis. Gel preparation and electrophoresis procedures and conditions for suitable for use in the evaluating step are known to the art. Separation of DNA fragments in a denaturing polyacrylamide gel and in capillary electrophoresis occurs based primarily on fragment size.

Once the amplified alleles are separated, the alleles and any other DNA in the gel or capillary (e.g., DNA size markers or an allelic ladder) can then be visualized and analyzed. Visualization of the DNA in the gel can be accomplished using any one of a number of prior art techniques, including silver labeling or reporters such as radioisotopes, fluorescers, chemiluminescers and enzymes in combination with detectable substrates. In one embodiment, the method for detection of multiplexes containing numerous loci is fluorescence, where primers for each locus in the multiplexing reaction is followed by detection of the labeled products employing a fluorometric detector. The alleles present in the DNA sample may be determined by comparison to a size standard such as a DNA marker or a locus-specific allelic ladder to determine the alleles present at each locus within the sample. Following the construction of allelic ladders for individual loci, these may be mixed and loaded for gel electrophoresis at the same time as the loading of amplified samples occurs. Each allelic ladder co-migrates with alleles in the sample from the corresponding locus.

The products of the multiplex reactions of the present invention can be evaluated using an internal lane standard, a specialized type of size marker configured to run in the same lane of a polyacrylamide gel or same capillary. The internal lane standard may consist of a series of fragments of known length. The internal lane standard may be labeled with a fluorescent dye which is distinguishable from other dyes in the amplification reaction.

Following construction of the internal lane standard, this standard may also be mixed with amplified sample or allelic ladders and loaded for electrophoresis for comparison of migration in different lanes of gel electrophoresis or different capillaries of capillary electrophoresis. Variation in the migration of the internal lane standard indicates variation in the performance of the separation medium. Quantitation of this difference and correlation with the allelic ladders allows correction in the size determination of alleles in unknown samples.

Exemplary fluorescent labeled primers include a compound of Formula (I) or (II), fluorescein-labeled (FL-), carboxy-tetramethylrhodamine-labeled (TMR-), and 5,6-carboxyrhodamine 6G-labeled (R6G) primers. Separation of the amplified fragments produced using such labeled primers may be achieved by slab gel electrophoresis or capillary electrophoresis. The resulting separated fragments can be analyzed using fluorescence detection equipment. Fluorescent methods of detection generally reveal fewer amplification artifacts than silver labeling. The smaller number of artifacts are due, in part, to the fact that only amplified strands of DNA with labels attached are detected in fluorescent detection, while both strands of every amplified allele of DNA produced from the multiplex amplification reaction is labeled and detected using the silver staining method of detection.

Kits

One aspect of the invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates, or present as a dye-conjugate where the conjugated substance is a specific binding pair member, or, for instance, a nucleoside, nucleotide, oligonucleotide, polynucleotide, peptide, or protein. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

In one embodiment, a kit of the invention includes one or more locus-specific primers. Instructions for use optionally may be included. Other optional kit components may include an allelic ladder directed to each of the specified loci, a sufficient quantity of enzyme for amplification, amplification buffer to facilitate the amplification, loading solution for preparation of the amplified material for electrophoresis, genomic DNA as a template control, a size marker to insure that materials migrate as anticipated in the separation medium, and a protocol and manual to educate the user and to limit error in use. The amounts of the various reagents in the kits also can be varied depending upon a number of factors, such as the optimum sensitivity of the process. It is within the scope of this invention to provide test kits for use in manual applications or test kits for use with automated detectors or analyzers.

The following Examples are intended to illustrate the invention above and should not be construed as to narrow its scope. One skilled in the art will readily recognize that the Examples may suggest other ways in which the present invention could be practiced. It should be understood that variations and modifications may be made while remaining within the scope of the invention.

EXAMPLES

Example 1

Preparation of Intermediates and Biological Labels: Compound PBI 3525

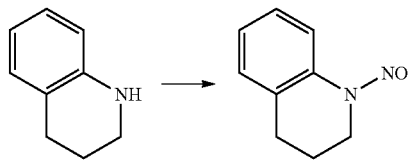

1-Nitroso-1,2,3,4-tetrahydroquinoline. To a stirred solution of 1,2,3,4-tetrahydroquinoline (10.0 g, 75.08 mmol) in 150 mL $CH_2Cl_2$ was added 150 mL 1M $H_2SO_4$, followed by $NaNO_2$ (5.70 g, 82.59 mmol). The reaction was stirred for 1.5 hours. The reaction mixture was partitioned, the organic layer retained, washed with a saturated solution of NaCl (aqueous), dried over $Na_2SO_4$ and concentrated to give the product (13.4 g 100%) as a dark oil. $^1$H-NMR (300 MHz, $CDCl_3$): δ 8.08 (d, 1H), 7.28 (m, 3H), 3.92 (m, 2H), 2.82 (m, 2H), 2.03 (m, 2H) ppm; MS m/z calculated for $C_9H_{10}N_2O$ (M+H): 163.09. Found: 163.1 (M+, ESI+).

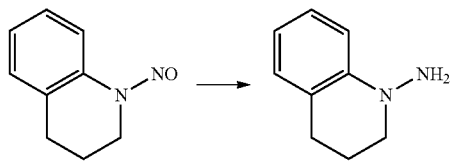

3,4-Dihydroquinolin-1(2H)-amine. A solution of 1-nitroso-1,2,3,4-tetrahydroquinoline (10.0 g, 61.66 mmol) in 60 mL dry THF was added dropwise to a refluxing suspension of $LiAlH_4$ (4.26 g, 112.21 mmol) in 130 mL THF. The reaction was allowed to reflux for 1 hour, cooled to 0° C., and then quenched by the dropwise addition of Rochelle's salt solution. The resulting precipitate was diluted with THF and filtered. The filtrate was then concentrated under reduced pressure, then purified by flash chromatography to give the product (4.83 g, 52.9%) as a white solid. ¹H-NMR (300 MHz, CDCl₃): δ 7.12 (m, 2H), 6.95 (d, 1H), 6.69 (m, 1H), 3.32 (m, 2H), 2.75 (t, 2H), 2.04 (dt, 2H) ppm; MS m/z calculated for $C_9H_{13}NO$ (M+H): 149.1. Found 149.1 (M+H, ESI+).

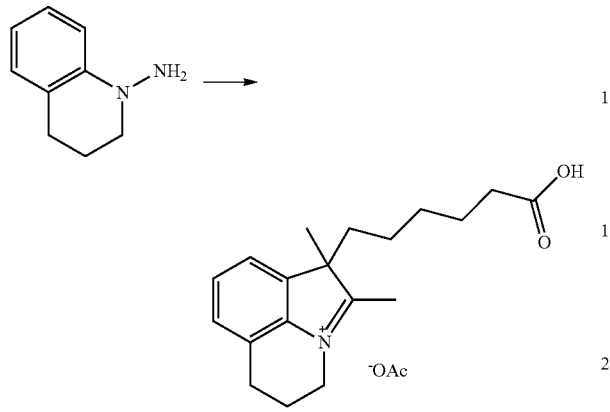

5,6,6-Trimethyl-1,2,3,6-tetrahydropyrrolo[3,2,1-ij]quinolinium acetate. A solution of 3,4-dihydroquinolin-1(2H)-amine (1.0 g, 6.75 mmol) and 7-methyl-8-oxononanoic acid (1.38 g, 7.43 mmol) in 10 mL acetic acid and 2.5 mL concentrated HCl was heated to reflux for 1 hour. The mixture was cooled to room temperature, diluted with water and extracted with CH₂Cl₂. The organic layer was washed with water, dried over Na₂SO₄ and concentrated to give a dark oil that was purified by silica gel chromatography affording the product (685.0 mg, 30.3%) as a dark oil. ¹H-NMR (300 MHz, d₆-DMSO): δ 7.85 (d, 1H), 7.80 (d, 1H), 7.58 (d, 1H), 2.63 (t, 2H), 1.90 (m, 2H), 1.75 (m, 11H), 1.30 (t, 2H), 1.22 (s, 3H), 1.11 (m, 2H) ppm; MS m/z calculated for $Cl_9H_{26}NO_2$ (M+): 300.2. Found 300.2 (M+, ESI+).

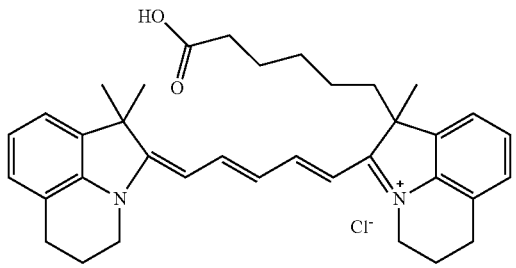

6-(5-Carboxypentyl)-5-((1E,3E,5E)-5-(1,1-dimethyl-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium chloride. A mixture of 5,6,6-trimethyl-1,2,3,6-tetrahydropyrrolo[3,2,1-ij]quinolinium acetate (480.0 mg, 1.86 mmol)and malonaldehyde bis(phenylimine)monohydrochloride (720.0 mg, 2.78 mmol) in 7 mL acetic anhydride and 7 mL acetic acid was refluxed for 2 hours. The reaction mixture was then cooled to room temperature and volatiles removed under reduced pressure. The resulting oil was diluted with CH₂Cl₂ and washed with 2M HCl (aqueous). The organic layer was dried over Na₂SO₄ and concentrated to give a brown solid that was subsequently combined with 645-carboxypentyl)-5,6-dimethyl-1,2,3,6-tetrahydropyrrolo[3,2,1-ij]quinolinium chloride (685.0 mg, 2.04 mmol) in 15 mL acetic anhydride. To this stirring mixture was added 2.5 mL triethylamine. The reaction was heated to 90° C. for 1 hour, yielding a blue solution that was then cooled to room temperature. After the crude product was concentrated under reduced pressure and dissolved in CH₂Cl₂, it was washed with 2 M HCl. The organic phase was then dried over Na₂SO₄ and concentrated to give a blue solid. The product (600.0 mg, 56.6%) was purified by silica gel flash chromatography giving a black solid. ¹H-NMR (300 MHz, CDCl₃): δ 8.49 (s, 2H), 7.07 (m, 8H), 6.22 (t, 1H), 6.10 (m, 2H), 4.13 (m, 2H), 3.94 (m, 2H), 2.84 (m, 4H), 2.22 (m, 4H), 1.67 (s, 9H), 1.23 (m, 4H), 0.83 (m, 4H) ppm; MS m/z calculated for $C_{36}H_{43}N_2O_2$ (M+): 535.7. Found 535.4 (M+, ESI+).

PBI 3525

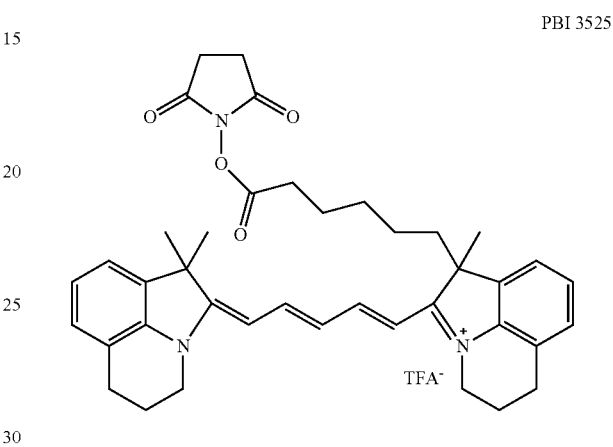

5-((1E,3E,5E)-5-(1,1-dimethyl-5,6-dihydro-1H-pyrrolo[3,2,1-ij]quinolin-2(4H)-ylidene)penta-1,3-dienyl)-6-(6-(2,5-dioxopyrrolidin-1-yloxy)-6-oxohexyl)-6-methyl-1,2,3,6-tetrahydropyrrolo[3,2,1-ij]quinolinium trifluoroacetate (PBI 3525). To the above dye in the free acid form (10 mg, 0.019 mmol) dissolved in 1 mL DMF was added N,N,N',N'-Tetramethyl-O—(N-succinimidyl)uronium tetrafluoroborate (11.3 mg, 0.037 mmol) and 65 µL diisopropylethylamine. The reaction was stirred 1 hour in the dark, diluted with water and purified by RP-HPLC giving the succinimidyl ester (13.7 mg, 98.0%) as a blue solid. MS m/z calculated for $C_{40}H_{46}N_3O_4$ (M+): 632.5 Found 632.6 (M+, ESI+).

Example 2

Preparation of Intermediates and Biological Labels: Compound PBI 3742

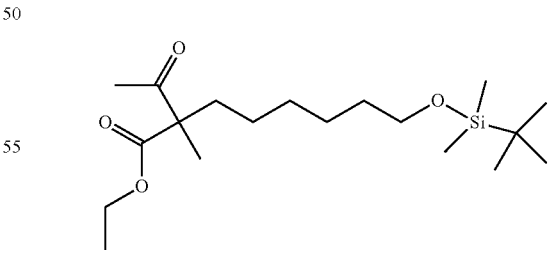

Ethyl 2-acetyl-8-(tert-butyldimethylsilyloxy)-2-methyloctanoate. Ethyl-2-methylacetoacetate (10.0 g, 69.36 mmol) was dissolved in 5 mL DMF and added dropwise to a suspension of NaH (2.77 g, 69.36 mmol) in 20 mL DMF at 0° C. Upon completion of addition, the mixture was allowed to warm to room temperature for 30 minutes giving a clear orange mixture that was cooled to 0° C. To this was added 6-bromohexanoate (23.56 g, 79.77 mmol) dropwise as a solution in 5 mL DMF over 20 minutes. The reaction mixture was warmed to 60° C. overnight, then cooled to room temperature and diluted with ethyl acetate. The organic layer was washed with 1st with dilute NH$_4$Cl solution, followed by water. The separated organic layer was dried over Na$_2$SO$_4$ and concentrated to a yellow oil. This crude product was subjected to silica gel chromatography yielding a colorless oil (13.5 g, 54.3%). $^1$H-NMR (300 MHz, CDCl$_3$): δ 4.16 (m, 2H), 3.56 (t, 2H), 2.11 (s, 3H), 1.84 (m, 1H), 1.74 (m, 1H), 1.46 (m, 2H), 1.25 (m, 6H), 1.14 (M, 2H), 0.86 (d, 9H), 0.01 (d, 6H) ppm; MS m/z calculated for C$_{19}$H$_{39}$O$_4$Si (M+H): 359.26. Found 359.3 (M+H, ESI+).

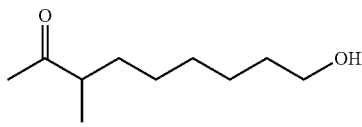

9-Hydroxy-3-methylnonan-2-one. Ethyl 2-acetyl-8-(tert-butyldimethylsilyloxy)-2-methyloctanoate (13.5 g, 37.65 mmol) was dissolved in 10 mL CH$_3$OH to which 5 g NaOH in 50 mL water was then added. The mixture was then heated to 50° C. overnight. The volume of the reaction mixture was reduced to about 50 mL under reduced pressure and acidified to pH 1 by the addition of 2 M HCl. This resulting mixture was heated to 60° C. for 5 hours. After cooling to room temperature the product was extracted into EtOAc. Concentration gave a yellow oil that was subjected to silica gel chromatography affording a colorless oil (4.25 g, 65.5%). $^1$H-NMR (300 MHz, CDCl$_3$): δ 3.60 (t, 2H) 2.46 (m, 1H), 2.09 (s, 3H), 1.54 (m, 4H), 1.30 (m, 6H), 1.04 (d, 3H) ppm; MS m/z calculated for C$_{10}$H$_{20}$O$_2$ (M+H): 173.2. Found 173.1 (M+H, ESI+).

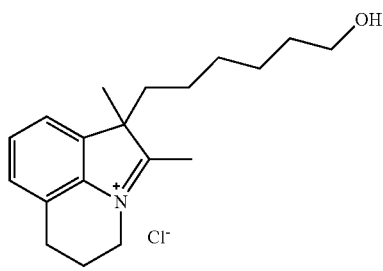

6-(6-Hydroxyhexyl)-5,6-dimethyl-1,2,3,6-tetrahydropyrrolo[3,2,1-ij]quinolinium chloride. A solution of 3,4-dihydroquinolin-1(2H)-amine (1.29 g, 8.71 mmol) and 9-hydroxy-3-methylnonan-2-one (1.65 g, 9.58 mmol) in 15 mL acetic acid and 2.5 mL concentrated HCl was heated to reflux for 1 hour. The mixture was cooled to room temperature, diluted with water and extracted with CH$_2$Cl$_2$. The organic layer was washed with water, dried over Na$_2$SO$_4$ and concentrated to give a dark oil that was purified by silica gel chromatography affording the product (1.84 g, 65.7%) as a dark oil.

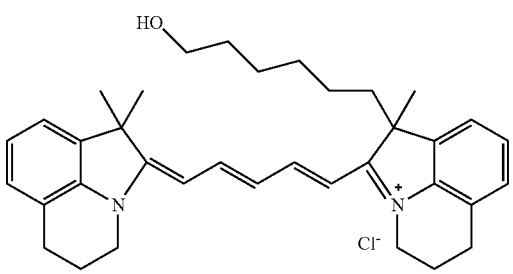

5-((1E,3E,5E)-5-(1,1-Dimethyl-5,6-dihydro-1H-pyrrolo[3,2,1-ij]quinolin-2(4H)-ylidene)penta-1,3-dienyl)-6-(6-hydroxyhexyl)-6-methyl-1,2,3,6-tetrahydropyrrolo[3,2,1-ij]quinolinium chloride. A mixture of 5,6,6-trimethyl-1,2,3,6-tetrahydropyrrolo[3,2,1-ij]quinolinium acetate (1.35 g, 6.29 mmol) and malonaldehyde bis(phenylimine)monohydrochloride (1.63 g, 6.29 mmol) in 10 mL acetic anhydride and 10 mL acetic acid were refluxed for 2 hours. The reaction mixture was then cooled to room temperature at which point the volatiles were removed under reduced pressure. The resulting oil was diluted with CH$_2$Cl$_2$, washed with 2M HCl (aqueous), dried over Na$_2$SO$_4$ and concreted to give a brown solid that was combined with 6-(6-hydroxyhexyl)-5,6-dimethyl-1,2,3,6-tetrahydropyrrolo[3,2,1-ij]quinolinium chloride (1.84 g, 5.73 mmol) in 20 mL acetic anhydride. To this stirring solution was added 5 mL triethylamine. The reaction was heated to 90° C. for 1 hour and then cooled to room temperature. The volatiles were concentrated under reduced pressure to give a dark oil. This oil was refluxed for 3 hours in 70 mL ACN and 70 mL 1 M HCl. The reaction mixture was concentrated to 50 mL and extracted with CH$_2$Cl$_2$. The separated organic phase was dried over Na$_2$SO$_4$ and concentrated to give a blue solid that was purified by silica gel flash chromatography affording the product (2.14 g, 73.7%) as a black solid. $^1$H-NMR (300 MHz, d$_6$DMSO): δ 8.34 (m, 2H), 7.15 (m, 6H), 6.48 (t, 2H), 6.61 (m, 2H), 4.00 (s, 4H), 3.32 (m, 9H), 2.81 (s, 4H), 2.10 (m, 4H), 1.67 (s, 9H), 1.11 (m, 4H) ppm; MS m/z calculated for C$_{36}$H$_{45}$N$_2$O$_2$ (M+): 521.4. Found 521.5 (M+, ESI+).

PBI 3742

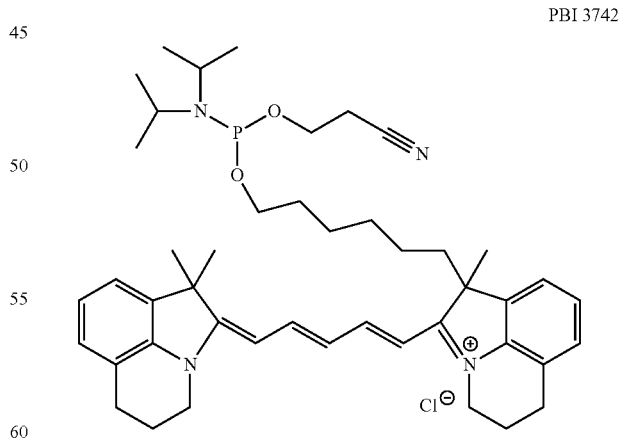

6-(6-((2-Cyanoethoxy)(diisopropylamino)phosphinooxy)hexyl)-5-((1E,3E,5E)-5-(1,1-dimethyl-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium chloride (PBI 3742). To a magnetically stirred solution of above alcohol (200 mg, 0.36 mmol) in 4 mL dry CH$_2$Cl$_2$ was added dry triethylamine (150 μL, 1 mmol), followed by a dropwise addition of 2-cyanoethyl diisopropylchlorophosphoramidite (100 μL, 0.45 mmol), all performed under an inert atmosphere of nitrogen gas. After stirring for 15 minutes, purification of reaction mixture was performed on a 94 gram amine column that was pre-equilibrated in straight CH$_2$Cl$_2$. A slow gradient ramping to 75% acetonitrile over 25 minutes was employed; the desired compound eluted at approximately 40% acetonitrile. Appropriate fractions are pooled and concentrated to yield 250 mg of amidite. $^{31}$P NMR (121 MHz, CDCl$_3$): δ 148.07; MS m/z calculated for C$_{45}$H$_{62}$N$_4$O$_2$P (M+): 721.46. Found 721.5 (M+, ESI+).

Example 3

Preparation of Intermediates and Biological Labels: Compounds PBI 3526, PBI 3665, PBI 3688, PBI 3786, and PBI 3785

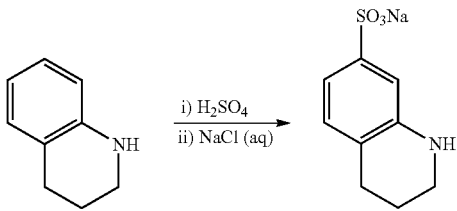

Sodium 1,2,3,4-tetrahydroquinoline-7-sulfonate. 1,2,3,4-tetrahydroquinoline was added dropwise to 40 mL fuming sulfuric acid at 0° C. over 15 minutes. This mixture was then heated to 100° C. for 1 hour with stirring. After cooling to 0° C. saturated NaCl (aqueous) was added drop wise, precipitating the crude product as a white solid. The solid was washed, first with cold isopropanol, followed by diethyl ether, then dried under vacuum to give the desired product as a white solid. $^1$H-NMR (300 MHz, d$_6$ DMSO): δ 7.43 (m, 2H), 7.21 (d, 1H), 3.38 (m, 2H), 2.81 (t, 2H) 1.96 (m, 2H) ppm; MS m/z calculated for C$_9$H$_{10}$NO$_3$S (M−): 212.04. Found 212.0 (M−, ESI−).

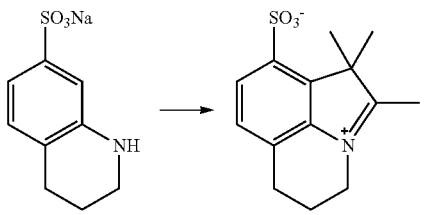

5,6,6-Trimethyl-1,2,3,6-tetrahydropyrrolo[3,2,1-ij]quinolinium-7-sulfonate. Sodium 1,2,3,4-tetrahydroquinoline-7-sulfonate (6.4 g, 30.0 mmol) was suspended in 15 mL glacial acetic acid with stirring. To this was added NaNO$_2$ (2.77 g, 33.0 mmol) in 10 mL water dropwise over 15 minutes. The reaction was then stirred for 45 minutes at room temperature. 3-methyl-2-butanone (4.8 mL, 45 mmol) was subsequently added followed by Zn dust (5.886 g, 90.0 mmol) which was added in small portions to control the exothermic reaction. The reaction mixture was heated to reflux for 1 hour, cooled to room temperature, and volatiles were removed under reduced pressure. Isopropanol was added to the residue which was stirred overnight precipitating the product. A grey solid (1.3 g, 15.5%) was collected by vacuum filtration. $^1$H-NMR (300 MHz, d$_6$-DMSO): δ 7.81 (d, 1H), 7.38 (d, 1H), 4.30 (t, 2H), 3.50 (s, 3H), 2.90 (t, 2H), 2.20 (s, 6H) ppm; MS m/z calculated for C$_{14}$H$_{18}$NO$_3$S (M+): 280.1 Found 280.1 (M+, ESI+).

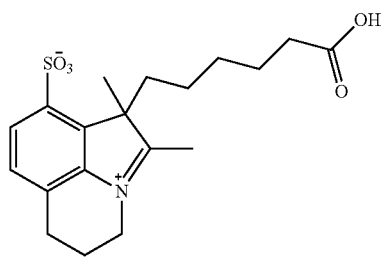

6-(5-Carboxypentyl)-5,6-dimethyl-1,2,3,6-tetrahydropyrrolo[3,2,1-ij]quinolinium-7-sulfonate. Sodium 1,2,3,4-tetrahydroquinoline-7-sulfonate (1.72 g, 7.30 mmol) was suspended in 8 mL glacial acetic acid with stirring. To this was added NaNO$_2$ (611.0 mg, 8.86 mmol) in 10 mL water dropwise over 15 minutes. The reaction was stirred for 45 minutes at room temperature. 7-methyl-8-oxononanoic acid (4.8 mL, 45 mmol) was subsequently added followed by Zn dust (1.58 g, 24.2 mmol) which was added in small portions. The reaction mixture was heated to reflux for 1 hour, cooled to room temperature, and volatiles were removed under reduced pressure. Isopropanol was added to the residue which was stirred overnight precipitating the product. A grey solid (500 mg, 18.4%) that was collected by vacuum filtration. $^1$H-NMR (300 MHz, CD$_3$OD): δ 8.00 (d, 1H), 7.50 (d, 1H), 4.50 (m, 2H), 3.35 (m, 3H), 3.10 (m, 2H), 3.05 (t, 2H), 2.25 (m, 2H), 1.81 (s, 3H), 1.40 (m, 2H), 1.15 (m, 2H), 0.60 (m, 2H) ppm; MS m/z calculated for C$_{19}$H$_{26}$NO$_5$S (M+2H): 382.2. Found 383.2 (M+2H, ESI+).

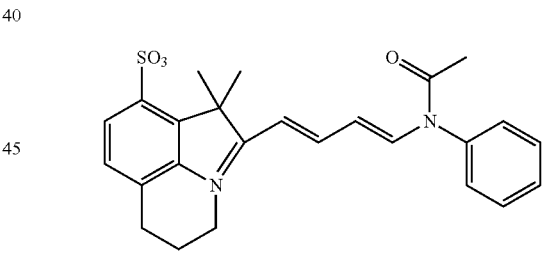

6,6-Dimethyl-5-((1E,3E)-4-(N-phenylacetamido)buta-1,3-dienyl)-1,2,3,6-tetrahydropyrrolo[3,2,1-ij]quinolinium-7-sulfonate. A mixture of 6-(5-carboxypentyl)-5,6-dimethyl-1,2,3,6-tetrahydropyrrolo[3,2,1-ij]quinolinium-7-sulfonate (1.3 g, 4.65 mmol) and malonaldehyde bis(phenylimine) monohydrochloride (1.60 g, 5.58 mmol) in 5 mL acetic anhydride and 5 mL acetic acid were heated to reflux for 4 hours with vigorous stirring. The mixture was cool and volatiles were removed under reduced pressure. The resulting solid was triturated with EtOAc and dried under hi-vac to give the hemi-cyanine as a red-brown solid (592.1 mg, 28.3%). $^1$H-NMR (300 MHz, CD$_3$OD): δ 8.65 (d, 1H), 8.28 (d, 1H), 7.93 (d, 1H), 7.61 (m, 2H), 7.37 (m, 2H), 6.58 (d, 1H), 5.57 (m, 1H), 4.25 (m, 2H), 2.97 (t, 2H), 2.21 (m, 2H), 2.10 (s, 3H), 1.95 (s, 6H) ppm; MS m/z calculated for C$_{25}$H$_{27}$N$_2$O$_4$S (M+): 451.17. Found 451.3 (M+, ESI+).

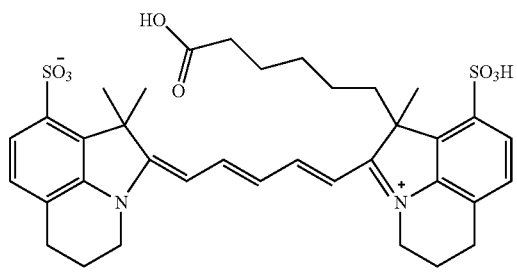

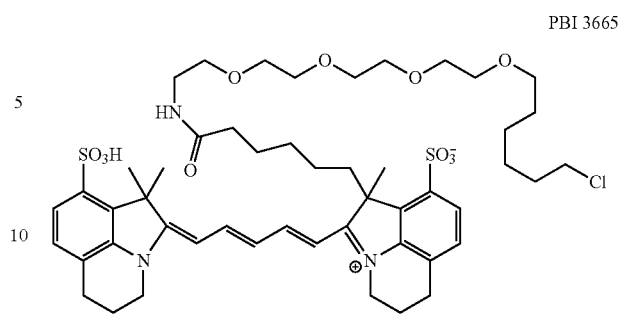

(E)-2-((2E,4E)-5-(6-(5-Carboxypentyl)-6-methyl-7-sulfo-1,2,3,6-tetrahydropyrrolo[3,2,1-ij]quinolinium-5-yl)penta-2,4-dienylidene)-1,1-dimethyl-2,4,5,6-tetrahydro-1H-pyrrolo[3,2,1-ij]quinoline-9-sulfonate. To a stirring mixture of 6,6-dimethyl-5-((1E,3E)-4-(N-phenylacetamido)buta-1,3-dienyl)-1,2,3,6-tetrahydropyrrolo[3,2,1-ij]quinolinium-7-sulfonate and 6-(5-carboxypentyl)-5,6-dimethyl-1,2,3,6-tetrahydropyrrolo[3,2,1-ij]quinolinium-7-sulfonate in 5 mL acetic anhydride was added 5 mL pyridine. The reaction was heated to 110° C. for 2 hours. After cooling to room temperature the product was precipitated with ethyl acetate, washed with Et$_2$O, and isolated by vacuum filtration. The final product was purified by reverse-phase HPLC yielding a blue solid. MS m/z calculated for $C_{36}H_{43}N_2O_8S_2$ (M+H): 695.25. Found 695.3 (M+H, ESI+).

6-(25-chloro-6-oxo-10,13,16,19-tetraoxa-7-azapentacosyl)-5-((1E,3E,5E)-5-(1,1-dimethyl-9-sulfo-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium-7-sulfonate (PBI 3665). To the above dye in the free acid form (170 mg, 0.24 mmol) dissolved in 5 mL DMF was added N,N,N',N'-Tetramethyl-O—(N-succinimidyl)uronium tetrafluoroborate (73.5 mg, 0.24 mmol) and diisopropylethylamine (85 μL, 0.49 mmol). N,18-dichloro-3,6,9,12-tetraoxaoctadecan-1-amine was added as a 0.5 M solution (0.5 mL, 0.24 mmol). The reaction was stirred overnight in the dark, diluted with water and purified by reverse-phase HPLC giving the product as a dark solid (36.4 mg, 15%). MS m/z calculated for $C_{50}H_{71}ClN_3O_{11}S_2$ (M+H): 988.4. Found 988.3 (M+H, ESI+).

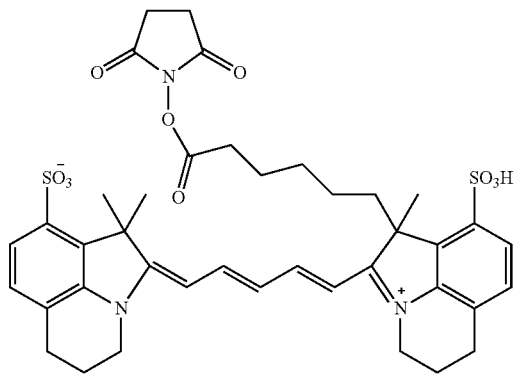

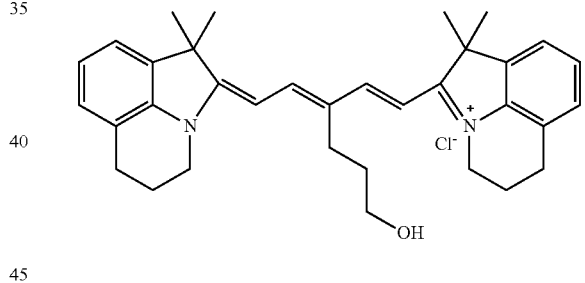

(E)-2-((2E,4E)-5-(6-(6-(2,5-Dioxopyrrolidin-1-yloxy)-6-oxohexyl)-6-methyl-7-sulfo-1,2,3,6-tetrahydropyrrolo[3,2,1-ij]quinolinium-5-yl)penta-2,4-dienylidene)-1,1-dimethyl-2,4,5,6-tetrahydro-1H-pyrrolo[3,2,1-ij]quinoline-9-sulfonate (PBI 3526). To the above dye in the free acid form (160 mg, 0.23 mmol) dissolved in 6 mL DMF was added N,N,N',N'-Tetramethyl-O—(N-succinimidyl)uronium tetrafluoroborate (104.0 mg, 0.35 mmol) and 195 μL diisopropylethylamine. The reaction was stirred 1 hour in the dark, diluted with water and purified by RP-HPLC giving the succinimidyl ester (85.0 mg, 46.7%) as a blue solid. MS m/z calculated for $C_{40}H_{45}N_3O_{10}S_2$ (M+): 791.25 Found 790.8 (M+, ESI+).

5-((1E,3E)-3-(E)-2-(1,1-Dimethyl-5,6-dihydro-1H-pyrrolo[3,2,1-ij]quinolin-2(4H)-ylidene)ethylidene)-6-hydroxyhex-1-enyl)-6,6-dimethyl-1,2,3,6-tetrahydropyrrolo[3,2,1-ij]quinolinium chloride (PBI 3688). To a stirred solution of 5,6,6-trimethyl-1,2,3,6-tetrahydropyrrolo[3,2,1-ij]quinolinium acetate (500.0 mg, 1.93 mmol) in 5 mL EtOH was added 5,6-dihydro-4H-pyran-3-carbaldehyde (93 mg, 0.83 mmol) and 2.5 mL acetic acid The resulting solution was heated to 50° C. for 2 hours. After cooling the volatiles were removed under reduced pressure. The subsequent residue was dissolved in 5 mL ethanol/2 mL triethylamine. This mixture was heated to reflux for 2.5 hours, cooled to room temperature, diluted with CH$_2$Cl$_2$, washed with 2 M HCl (aqueous) and concentrated. The residue was purified by silica gel chromatography, giving the product as a blue solid. $^1$H-NMR (CDCl$_3$, 300 MHz): δ 7.54 (d, 2H), 7.10 (m, 6H), 6.32 (d, 2H), 4.14 (t, 4H), 3.76 (t, 2H), 2.81 (m, 6H), 2.25 (m, 4H), 1.80 (m, 2H), 1.67 (s, 12H) ppm; MS m/z calculated for $C_{34}H_{41}N_2O$ (M+): 493.3. Found 493.4 (M+, ESI+).

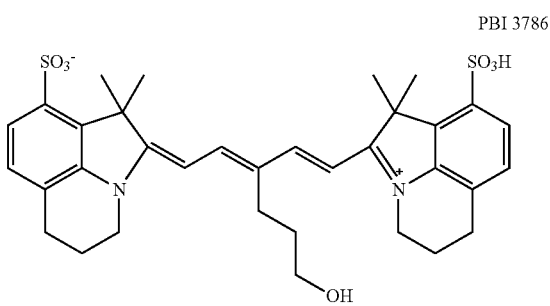

PBI 3786

(E)-2-((E)-3-((E)-2-(6,6-Dimethyl-7-sulfo-1,2,3,6-tetrahydropyrrolo[3,2,1-ij]quinolinium-5-yl)vinyl)-6-hydroxyhex-2-enylidene)-1,1-dimethyl-2,4,5,6-tetrahydro-1H-pyrrolo[3,2,1-ij]quinoline-9-sulfonate (PBI 3786). To a stirred solution of 5,6,6-trimethyl-1,2,3,6-tetrahydropyrrolo[3,2,1-ij]quinolinium-7-sulfonate (3.80 g, 13.55 mmol) in 30 mL EtOH was added 5,6-dihydro-4H-pyran-3-carbaldehyde (690.0 mg, 6.16 mmol) and 8 mL acetic acid The resulting solution was heated to 50° C. for 2.5 hours. After cooling the volatiles were removed under reduced pressure. The residue was dissolved in 30 mL ethanol/5 mL triethylamine. This mixture was heated to reflux for 3 hours, cooled to room temperature acidified with 2 M HCl (aqueous) and concentrated. The resulting solid was stirred in isopropanol to give the product as a blue solid that was collected by vacuum filtration. MS m/z calculated for $C_{34}H_{41}N_2O_7S_2$ (M+): 653.24. Found 653.2 (M+, ESI+).

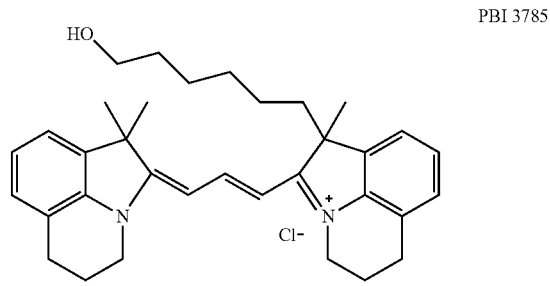

PBI 3785

5-((1E,3E)-3-(1,1-Dimethyl-5,6-dihydro-1H-pyrrolo[3,2,1-ij]quinolin-2(4H)-ylidene)prop-1-enyl)-6-(6-hydroxyhexyl)-6-methyl-1,2,3,6-tetrahydropyrrolo[3,2,1-ij]quinolinium chloride (PBI 3785). A mixture of 5,6,6-trimethyl-1,2,3,6-tetrahydropyrrolo[3,2,1-ij]quinolinium acetate (1.0 g, 3.19 mmol) and N,N'-diphenylformamidine (939.6 mg, 4.79 mmol) in 10 mL acetic anhydride and 10 mL acetic acid were refluxed for 2 hours. After cooling to room temperature the volatiles were removed under reduced pressure. The resulting oil was diluted with $CH_2Cl_2$, washed with 2M HCl (aqueous), dried over $Na_2SO_4$ and concreted to give a brown solid. This solid was combined with 6-(6-hydroxyhexyl)-5,6-dimethyl-1,2,3,6-tetrahydropyrrolo[3,2,1-ij]quinolinium chloride (1.13 g, 3.51 mmol) in 15 mL acetic anhydride. To this stirring mixture was added 2.5 mL triethylamine. The reaction was heated to 90° C. for 1 hour yielding a dark mixture. After cooling to room temperature the volatiles were removed under reduced pressure. The residue was dissolved in $CH_2Cl_2$ and was washed with 2 M HCl. The separated organic phase was dried over $Na_2SO_4$ and concentrated to give a red solid. This was subsequently dissolved in 75 mL ACN/75 mL 1 M HCl (aqueous) and refluxed for 2.5 hours. The volume of the mixture was reduced to about 50 mL and the product was extracted with $CH_2Cl_2$. Evaporation of solvent gave a dark solid that was subjected to silica gel chromatography affording the product as a red solid. MS m/z calculated for $C_{34}H_{43}N_2O$ (M+): 495.3. Found 495.5 (M+, ESI+).

Example 4

Preparation of Intermediates and Biological Labels: Compounds PBI 3845 and PBI 3838

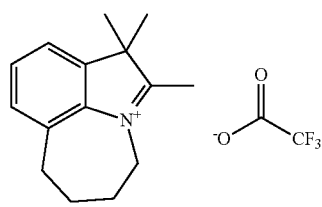

1

6,7,7-Trimethyl-2,3,4,7-tetrahydro-1H-azepino[3,2,1-hi]indolium trifluoroacetate (1): To a solution of 1-aminotetrahydrobenzo[b]azepine (Prepared as in *J. Med. Chem.* 36, 3693-3699, 1993) (0.85 g) in EtOH (35 mL) was added methylisopropylketone (0.84 mL). This reaction was heated to reflux for 90 min, cooled, and concentrated. The crude hydrazone was dissolved in AcOH (20 mL) and concentrated HCl (2 mL) and heated to reflux for 45 min. Solvent was removed, and the resulting dark solid was purified by silica gel chromatography (9/1 $CH_2Cl_2$/MeOH) followed by reverse phase preparative HPLC to provide the desired product (0.6 g) as a light purple solid: $^1$H NMR (DMSO-$d_6$) δ 7.61 (d, 1H), 7.45 (t, 1H), 7.35 (d, 1H), 4.54-4.50 (m, 2H), 3.12 (t, 2H), 2.72 (s, 3H), 2.15-2.09 (m, 2H), 2.05-1.98 (m, 2H), 1.49 (s, 6H); MS m/z calculated for $C_{15}H_{20}N^+$: (M+), 214.3. Found 214 (M+, ESI+).

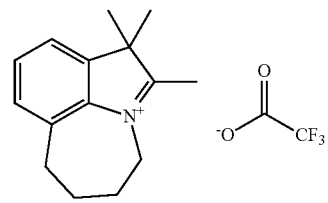

4,4,5-Trimethyl-4,7,8,9,10,11-hexahydroazocino[3,2,1-hi]indolium trifluoroacetate: In an analogous procedure to compound I, the title compound was synthesized from 1-aminohexahydrobenzo[b]azocine (Prepared as in *J. Med. Chem.* 36, 3693-3699, 1993): $^1$H NMR (DMSO-$d_6$) δ 7.69 (d, 1H), 7.52 (t, 1H), 7.38 (d, 1H), 4.69 (t, 2H), 3.17 (s, 2H), 2.81 (s, 3H), 2.10-2.01 (m, 2H), 1.85-1.79 (m, 2H), 1.53 (s, 6H) 1.40-1.31 (m, 2H); MS m/z calculated for $C_{16}H_{22}N^+$: (M+): 228. Found 228.

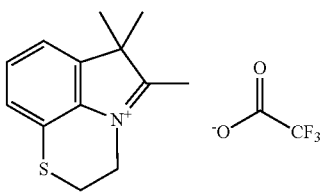

5,6,6-Trimethyl-3,6-dihydro-2H-[1,4]thiazino[2,3,4-hi]indol-4-ium trifluoroacetate: In an analogous procedure to compound I, the title compound was synthesized from 1-aminobenzothiomorpholine (Prepared as in *J. Med. Chem.* 36, 3693-3699, 1993): $^1$H NMR (DMSO-$d_6$) δ 7.53-7.41 (m, 3H), 4.59 (br s, 2H), 3.50 (br s, 2H), 2.71 (s, 3H), 1.51 (s, 6H); MS m/z calculated for $C_{13}H_{16}NS^+$ (M+): 218. Found 218 (M+, ESI+).

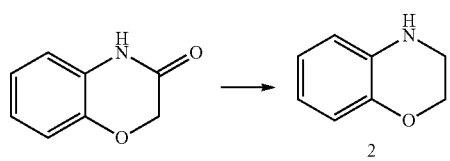

3,4-Dihydro-2H-benzo[b][1,4]oxazine (2). A solution of LAH (970 mg, 25.6 mmol) was refluxed in THF 50 mL under nitrogen atmosphere. A solution of 2H-1,4-Benzoaxin-3(4H)-one (1.88 g, 12.6 mmol) was added dropwise over 10 minutes. After 1 hour, the reaction was cooled in an ice bath and slowly quenched with a solution of Rochelle's salt, triturated with EtOAc and filtered through a plug of celite. The solvent was evaporated and the crude product purified by column chromatography on silica (1:1 heptane: EtOAc) to give 1.2 g of the desired product. $^1$H-NMR (300 MHz, $CD_2Cl_2$) δ: 6.76 (m, 2H), 6.61 (m, 2H), 4.22 (m, 2H), 3.80 (bs, NH), 3.39 (m, 2H); MS m/z calculated for $C_8H_{10}NO$ (M+H) 136.08. Found 136.1 (M+H, ESI+).

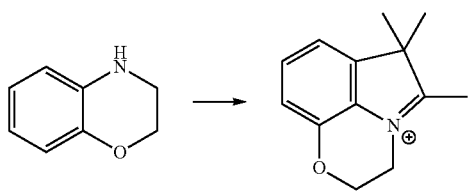

5,6,6-Trimethyl-3,6-dihydro-2H-[1,4]oxazino[2,3,4-hi]indol-4-ium (3). 3,4-Dihydro-2H-benzo[b][1,4]oxazine (1.15 g, 8.5 mmol) was stirred in acetic acid (10 mL) in a 100 mL round-bottomed flask at RT. A solution of $NaNO_2$ (646 mg, 9.4 mmol) in water (2 mL) was added and the solution was stirred for 2 h. 3-methyl-2-butanone (2.2 g, 25.5 mmol) was added followed by slow addition of Zn (1.67 g, 25.5 mmol). The reaction was refluxed at 100° C. for 1 h, cooled to RT and evaporated to give a brownish residue which was purified by column chromatography on silica (1:9 MeOH: DCM) to give the desired product (380 mg, 17.1%). $^1$H-NMR (300 MHz, $CD_2Cl_2$) δ: 6.75 (m, 1H), 6.65 (m, 2H), 4.39 (m, 2H), 3.54 (bs, 2H), 2.04 (s, 3H), 1.40 (s, 6H); MS m/z calculated for $C_{13}H_{16}NO$ (M+) 202.12. Found 202.1 (M+).

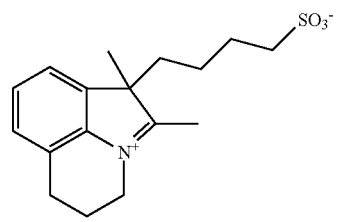

4-(5,6-Dimethyl-1,2,3,6-tetrahydropyrrolo[3,2,1-ij]quinolinium-6-yl)butane-1-sulfonate. 3,4-Dihydroquinolin-1(2H)-amine (2.0 g, 13.5 mmol) and 5-methyl-6-oxoheptane-1-sulfonic acid (prepared as in U.S. 2006/0239922 (Cooper et al.)) (4.216 g, 20.2 mmol) were refluxed in 15 mL acetic acid and 1.5 mL concentrated HCl for 1 hr. The mixture was cooled and volatiles were removed under reduced pressure giving a brown residue that was purified by flash chromatography to give the product (3.4 g, 78.4%) as a yellow solid. $^1$H-NMR (300 MHz, $D_2O$) δ: 7.53 (m, 2H), 7.42 (m, 1H), 4.44 (m, 2H), 3.02 (t, J=6 Hz, 2H), 2.74 (m, 5H), 2.33-2.21 (m, 4H), 1.59 (m, 5H), 0.93 (m, 2H).

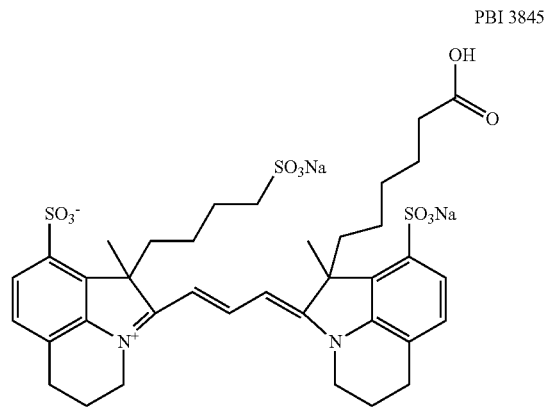

PBI 3845

Sodium 2-((1E,3Z)-3-(1-(5-carboxypentyl)-1-methyl-9-sulfonato-5,6-dihydro-1H-pyrrolo[3,2,1-ij]quinolin-2(4H)-ylidene)prop-1-enyl)-1-methyl-1-(4-sulfonatobutyl)-1,4,5,6-tetrahydropyrrolo[3,2,1-ij]quinolinium-9-sulfonate (PBI 3845). A mixture of 5,6-dimethyl-6-(4-sulfobutyl)-1,2,3,6-tetrahydropyrrolo[3,2,1-ij]quinolinium-7-sulfonate (250 mg, 0.59 mmol) and N,N'-diphenylformamidine (139.0 mg, 0.71 mmol) in 2 mL acetic anhydride and 2 mL acetic acid were refluxed for 2 hr. After cooling to room temperature the volatiles were removed under reduced pressure. The resulting oil was triturated with ethyl acetate to give a brown solid that was collect by vacuum filtration and dried under hi-vacuum. This solid was combined with 645-carboxypentyl)-5,6-dimethyl-1,2,3,6-tetrahydropyrrolo[3,2,1-ij]quinolinium-7-sulfonate (0.21 mg, 0.55 mmol) in 2 mL acetic anhydride, 2 mL pyridine and 0.5 mL triethylamine. The reaction was heated to 90° C. for 1 hr yielding a dark mixture. After cooling to room temperature the volatiles were removed under reduced pressure and the residue was subjected RP-HPLC affording the product (156.4 mg, 30.8 mmol) as a red solid.

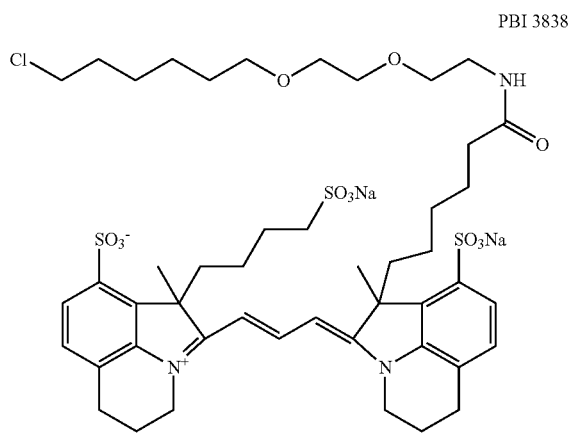

PBI 3838

Sodium 2-((1E,3Z)-3-(1-(6-(2-(2-(6-chlorohexyloxy)ethoxy)ethylamino)-6-oxohexyl)-1-methyl-9-sulfonato-5,6-dihydro-1H-pyrrolo[3,2,1-ij]quinolin-2(4H)-ylidene)prop-1-enyl)-1-methyl-1-(4-sulfonatobutyl)-1,4,5,6-tetrahydropyrrolo[3,2,1-ij]quinolinium-9-sulfonate (PBI 3838). To the above dye in the free acid form (60 mg, 0.078 mmol) dissolved in 5 mL DMF was added N,N,N',N'-Tetramethyl-O—(N-succinimidyl)uronium tetrafluoroborate (32.4 mg, 0.11 mmol) and 37.5 μL diisopropylethylamine. The reaction was stirred 0.5 hr in the dark before the addition of 2-(2-(6-chlorohexyloxy)ethoxy)ethanaminium chloride (28.0 mg, 0.11 mmol). The reaction was stirred for 4 hrs, diluted with water and purified by RP-HPLC giving desired product (85.0 mg, 46.7%) as a blue solid. MS m/z calculated for $C_{47}H_{66}Cl_3N_3Na_2O_{12}S_3$ (M+HCl): 1076.3 Found 1076.5 (M+HCl, ESI+).

Example 5

Biological Labels: Compounds PBI 3846, PBI 3847, PBI 3848, PBI 3855, and PBI 3856

The following compounds have been prepared using the methods described above and the appropriate corresponding starting materials.

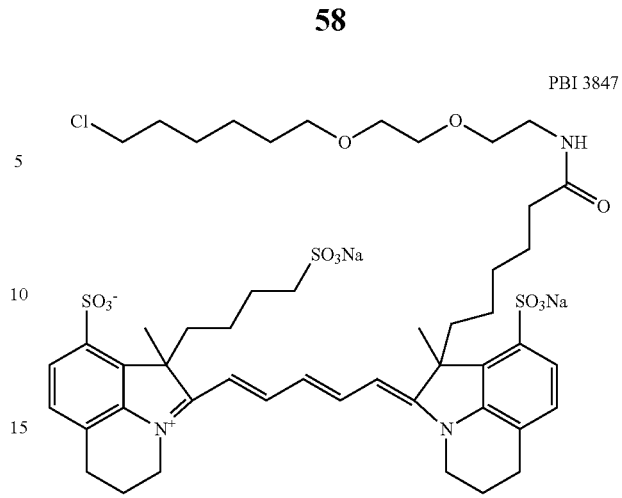

PBI 3847

Sodium 2-((1E,3E,5Z)-5-(1-(6-(2-(2-(6-chlorohexyloxy)ethoxy)ethylamino)-6-oxohexyl)-1-methyl-9-sulfonato-5,6-dihydro-1H-pyrrolo[3,2,1-ij]quinolin-2(4H)-ylidene)penta-1,3-dienyl)-1-methyl-1-(4-sulfonatobutyl)-1,4,5,6-tetrahydropyrrolo[3,2,1-ij]quinolinium-9-sulfonate (PBI 3847).

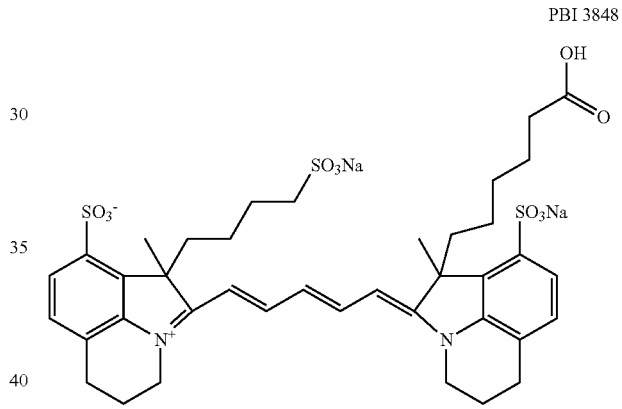

PBI 3848

Sodium 5-((1E,3E,5Z)-5-(1-(5-carboxypentyl)-1-methyl-9-sulfonato-5,6-dihydro-1H-pyrrolo[3,2,1-ij]quinolin-2(4H)-ylidene)penta-1,3-dienyl)-6-methyl-6-(4-sulfonatobutyl)-1,2,3,6-tetrahydropyrrolo[3,2,1-ij]quinolinium-7-sulfonate (PBI 3848).

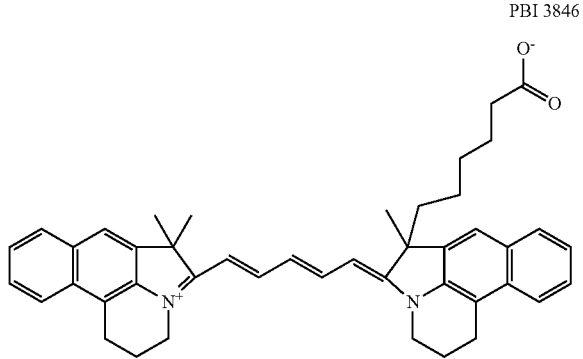

PBI 3846

6-((Z)-5-((2E,4E)-5-(6,6-Dimethyl-1,2,3,6-tetrahydrobenzo[f]pyrrolo[3,2,1-ij]quinolinium-5-yl)penta-2,4-dienylidene)-6-methyl-2,3,5,6-tetrahydro-1H-benzo[f]pyrrolo[3,2,1-ij]quinolin-6-yl)hexanoate (PBI 3846).

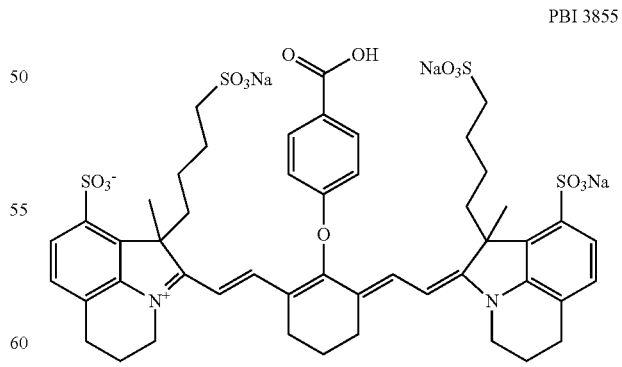

PBI 3855

Sodium 5-((E)-2-((E)-2-(4-carboxyphenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl)vinyl)-6-methyl-6-(4-sulfonatobutyl)-1,2,3,6-tetrahydropyrrolo[3,2,1-ij]quinolinium-7-sulfonate (PBI 3855).

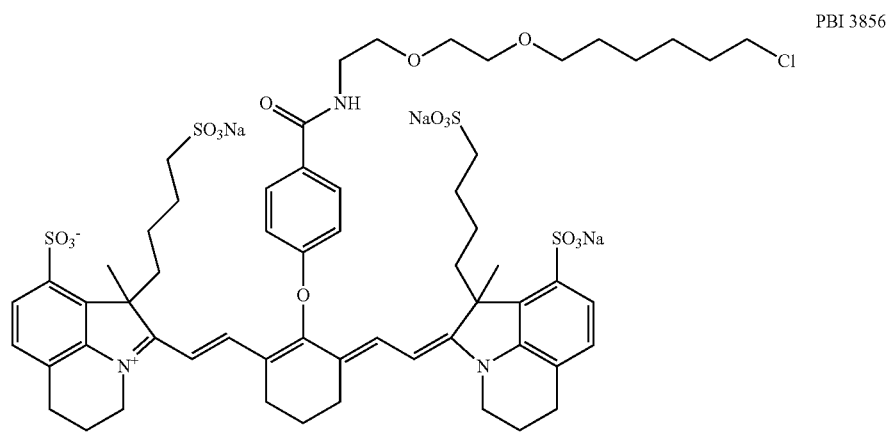

Sodium 2-((E)-2-((E)-2-(4-(2-(2-(6-chlorohexyloxy)ethoxy)ethylcarbamoyl)phenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl)vinyl)-1-methyl-1-(4-sulfonatobutyl)-1,4,5,6-tetrahydropyrrolo[3,2,1-ij]quinolinium-9-sulfonate (PBI 3856).

a red solid. MS m/z calculated for $C_{48}H_{56}N_5O_{11}S_4$ (M+H): 1006.3. Found: 1006.3 (M+H).

Example 7

Synthesis of PBI 4011

Example 6

Synthesis of PBI 3956

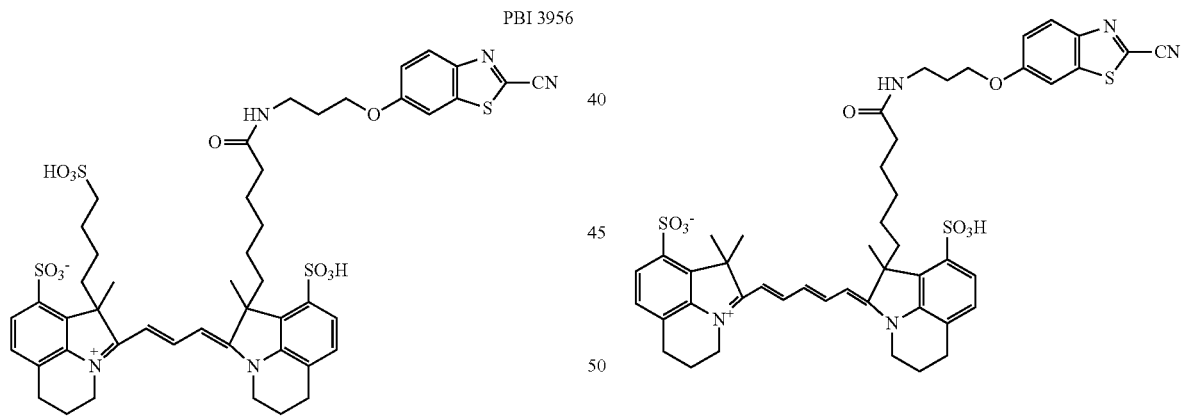

2-((1E,3Z)-3-(1-(6-((3-((2-cyanobenzo[d]thiazol-6-yl)oxy)propyl)amino)-6-oxohexyl)-1-methyl-9-sulfo-5,6-dihydro-1H-pyrrolo[3,2,1-ij]quinolin-2(4H)-ylidene)prop-1-en-1-yl)-1-methyl-1-(4-sulfobutyl)-1,4,5,6-tetrahydropyrrolo[3,2,1-ij]quinolin-3-ium-9-sulfonate (PBI 3956): To compound 3845 (30.0 mg, 0.038 mmol) dissolved in 1 ml DMF was added N—N—N'—N'-Tetramethyl-O—(N-succinimidyl)uronium tetrafluoroborate (34.3 mg, 0.11 mmol) and 66.2 μL diisopropylethylamine. The reaction was stirred 0.5 hr in the dark before the addition of 3-((2-cyanobenzo[d]thiazol-6-yl)oxy)propan-1-aminium trifluoroacetate (20.4 mg, 0.38 mmol). The reaction was stirred for 1 hr, diluted with water and purified by RP-HPLC giving the desired product as 2-((1E,3E,5Z)-5-(1-(6-((3-((2-cyanobenzo[d]thiazol-6-yl)oxy)propyl)amino)-6-oxohexyl)-1-methyl-9-sulfo-5,6-dihydro-1H-pyrrolo[3,2,1-ij]quinolin-2(4H)-ylidene)penta-1,3-dien-1-yl)-1,1-dimethyl-1,4,5,6-tetrahydropyrrolo[3,2,1-ij]quinolin-3-ium-9-sulfonate (PBI 4011): To compound 3526 (17.0 mg, 0.21 mmol) dissolved in 1 mL DMF was added 34(2-cyanobenzo[d]thiazol-6-yl)oxy)propan-1-aminium trifluoroacetate (9.0 mg, 0.26 mmol) and 11.2 uL diisopropyethylamine. The reaction was stirred in the dark for 4 hrs, diluted with water and purified by RP-HPLC giving the product as a dark solid. MS m/z calculated for $C_{47}H_{51}N_5O_8S_3$ (M−): 910.1. Found 910.7 (M−).

Example 8

Synthesis of PBI 3957

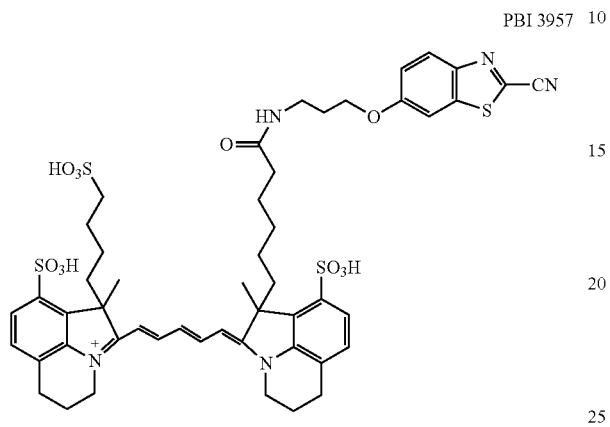

PBI 3957

2-((1E,3E,5Z)-5-(1-(6-((3-((2-cyanobenzo[d]thiazol-6-yl)oxy)propyl)amino)-6-oxohexyl)-1-methyl-9-sulfo-5,6-dihydro-1H-pyrrolo[3,2,1-ij]quinolin-2(4H)-ylidene)penta-1,3-dien-1-yl)-1-methyl-9-sulfo-1-(4-sulfobutyl)-1,4,5,6-tetrahydropyrrolo[3,2,1-ij]quinolin-3-ium (PBI 3957): To compound 3848 (65.0 mg, 0.08 mmol) dissolved in 1.5 mL DMF was added N—N—N'—N'-Tetramethyl-O—(N-succinimidyl)uronium tetrafluoroborate (113.5 mg, 0.38 mmol) and 0.13 mL diisopropylethylamine. The reaction was stirred for 2 hrs, diluted with water and purified by RP-HPLC to give the succinimidyl ester as a blue solid. To this compound (68.9 mg, 0.08 mmol) dissolved in 1.5 mL DMF was added 3-((2-cyanobenzo[d]thiazol-6-yl)oxy)propan-1-aminium trifluoroacetate (52.4 mg, 0.15 mmol) and 39 µL diisopropylethylamine. The reaction was stirred for 2 hrs in the dark, diluted with water and purified by RP-HPLC giving the desired product (10.0 mg) as a blue solid. MS m/z calculated for $C_{50}H_{58}N_5O_{11}S_4$ (M+H): 1032.3. Found 1032.3 (M+H).

Example 9

General Procedure for Use of N-Hydroxysuccinimidyl Esters of Tricyclic Cyanines

1 µmole scale. The 5'-amino labeled oligonucleotide was synthesized on an ABI 394 DNA synthesizer (1 µmole) using a 5' Amino modifier C6 TFA amidite from Glen Research. Deprotection in concentrated ammonium hydroxide overnight at 60° C. yielded the 5'-aminohexyl labeled oligonucleotide. The resulting oligonucleotide was evaporated to dryness, redissolved in 1 mL 0.5M NaCl and desalted on a NAP-10 size exclusion cartridge (GE Healthcare). After desalting, the oligonucleotide was evaporated to dryness followed by re-dissolution in 200 µL 0.5M sodium carbonate buffer, pH 9.0. The tricyclic cyanine succinimidyl ester (3526, 3525) was dissolved in DMF at a concentration of 20 µL/mg. Two×20 µL aliquots of the dye/DMF solution were added to the dissolved oligonucleotide, 30 minutes apart. After the second addition, the reaction was mixed for 1 hour. After one hour, it was diluted to 1 mL with water and desalted on a NAP-10 column (GE Healthcare). The NAP-10 eluate was purified by reversed phase HPLC on a Phenomonex Jupiter C18 column using an acetonitrile/0.1M TEAA buffer system. The HPLC purified oligonucleotide was evaporated to dryness, redissolved in 0.01M triethylammonium bicarbonate and desalted on a NAP-10 column. After final desalt step, the oligonucleotide was evaporated to dryness.

100 µmole scale. The 5'-amino labeled oligonucleotide was synthesized on an AKTA OligoPilot (100 µmole) DNA synthesizer using a 5' Amino modifier C6 TFA amidite from Glen Research. Deprotection in concentrated ammonium hydroxide overnight at 60° C. yielded the 5'-aminohexyl labeled oligonucleotide. The resulting oligonucleotide was evaporated to dryness, redissolved in 75 mL 2M NaCl and desalted on a 500 mL G-25 column (GE Healthcare). After desalting, the oligonucleotide was evaporated to dryness followed by re-dissolution in 50 mL 0.5M sodium carbonate buffer, pH 9.0. The tricyclic cyanine succinimidyl ester was dissolved in DMF at a concentration of 20 µL/mg. 2400 µL of the dye/DMF solution was added dropwise to the dissolved oligonucleotide. The reaction was mixed for 1 hour. The dye conjugated oligonucleotide was neutralized with sodium acetate, pH 5.5 solution and precipitated from 2× volume of ethanol. The precipitated oligonucleotide was centrifuged at 9000 rpm for 60 minutes. The supernate was decanted to waste. The resulting solid was dissolved in 70 mL water and purified by ion-exchange chromatography. The oligonucleotide was concentrated and desalted using tangential flow ultrafiltration and subsequently evaporated to dryness.

Example 10

General Procedure for Use of Phosphoramidites of Tricyclic Cyanines

1 µmole scale. The 5'-tricyclic cyanine labeled oligonucleotide was synthesized on an ABI 394 DNA synthesizer (1 µmole) using a cyanine amidite (3742) from Promega Biosciences, LLC, dissolved to 0.1M in acetonitrile. Deprotection in t-butylamine/MeOH/water (25/25/50) for two hours at 60° C. yielded the 5'-tricyclic cyanine labeled oligonucleotide (Pac-dA, ipPAc-dG and Ac-dC amidites were required for mild deprotection conditions). The resulting oligonucleotide was evaporated to dryness, redissolved in 0.01M triethylammonium bicarbonate and purified by reversed phase HPLC on a Phenomonex Jupiter C18 column using an acetonitrile/0.1M TEAA buffer system. The HPLC purified oligonucleotide was evaporated to dryness, redissolved in 0.01M triethylammonium bicarbonate and desalted on a NAP-10 column (GE Healthcare). After final desalt step, the oligonucleotide was evaporated to dryness.

100 µmole scale. The 5'-tricyclic cyanine labeled oligonucleotide was synthesized on an AKTA OligoPilot DNA synthesizer (100 µmole) using cyanine amidite (3742) from Promega Biosciences, LLC, dissolved to 0.1M in acetonitrile. Deprotection in t-butylamine/MeOH/water (25/25/50) for two hours at 60° C. yielded the 5'-tricyclic cyanine labeled oligonucleotide (Pac-dA, ipPAc-dG and Ac-dC amidites were required for mild deprotection conditions). The resulting oligonucleotide was evaporated to dryness, redissolved in 0.01M triethylammonium bicarbonate and purified by ion-exchange HPLC. The resulting purified oligonucleotide was concentrated and desalted using tangential flow ultrafiltration and evaporated to dryness.

Example 11

Use of Cyanine Dye in Multiplex PCR

A DNA template was amplified simultaneously at the individual short tandem repeat (STR) loci Amelogenin, D3S1358, TH01, D2S11, D18S51, D10S1248, D1S1656, D2S1338, D16S539, D22S1045, vWA, D8S1179, FGA, D12S391 and D19S433 in a single reaction vessel. The PCR amplification was performed using 5 μL of PowerPlex® ESX 16 Master Mix (Promega), 2.5 μL PowerPlex® ESX 16 10× Primer Mix (Promega), 0.5 ng template DNA and 4.0 units GoTaq® Hot Start Polymerase (Promega) to a final volume 25 μl with water. One primer of each primer pair for each STR loci was labeled as indicated in Table 1.

TABLE 1

| STR Loci | Label |
|---|---|
| Amelogenin | Fluorescein |
| D3S1359 | Fluorescein |
| D19S433 | Fluorescein |
| D2S1338 | Fluorescein |
| D22S1045 | Fluorescein |
| D16S539 | JOE |
| D18S51 | JOE |
| D1S1656 | JOE |
| D10S1248 | JOE |
| D2S441 | JOE |
| TH01 | TMR-ET |
| vWA | TMR-ET |
| D21S11 | TMR-ET |
| D12S391 | TMR-ET |
| D8S1179 | CXR-ET |
| FGA | CXR-ET |

The DNA template was amplified using a GeneAmp® PCR System 9700 Thermal Cycler with the following amplification protocol: 96° C. for 2 minutes, 30 cycles of 96° C. for 30 seconds, 59° C. for 2 minutes, 72° C. for 90 seconds, followed by a hold at 60° C. for 45 minutes.

Figure 3:
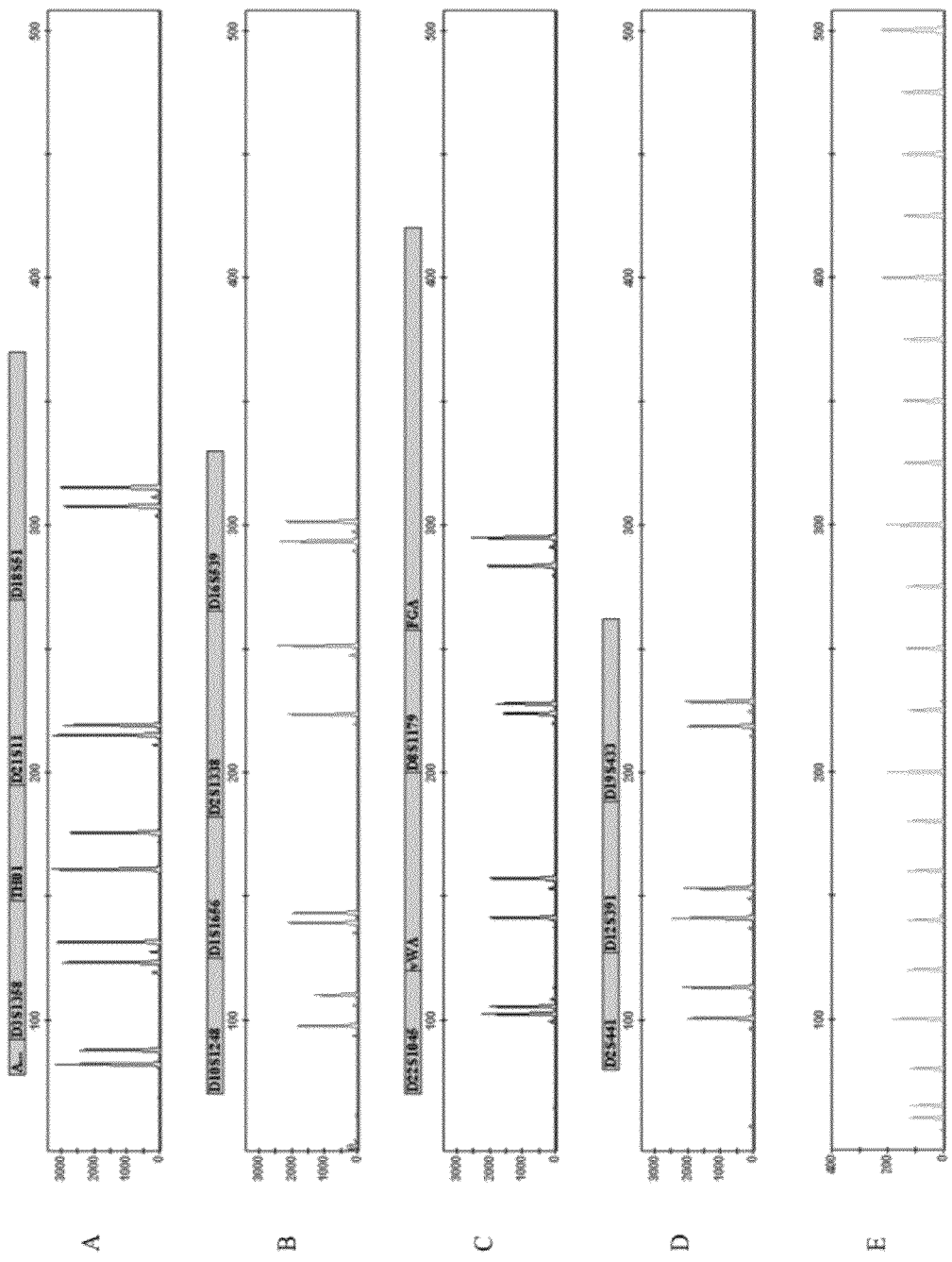
FIG. 3 illustrates an electropherogram showing the PowerPlex® ESX 16 System.
Figure 4:
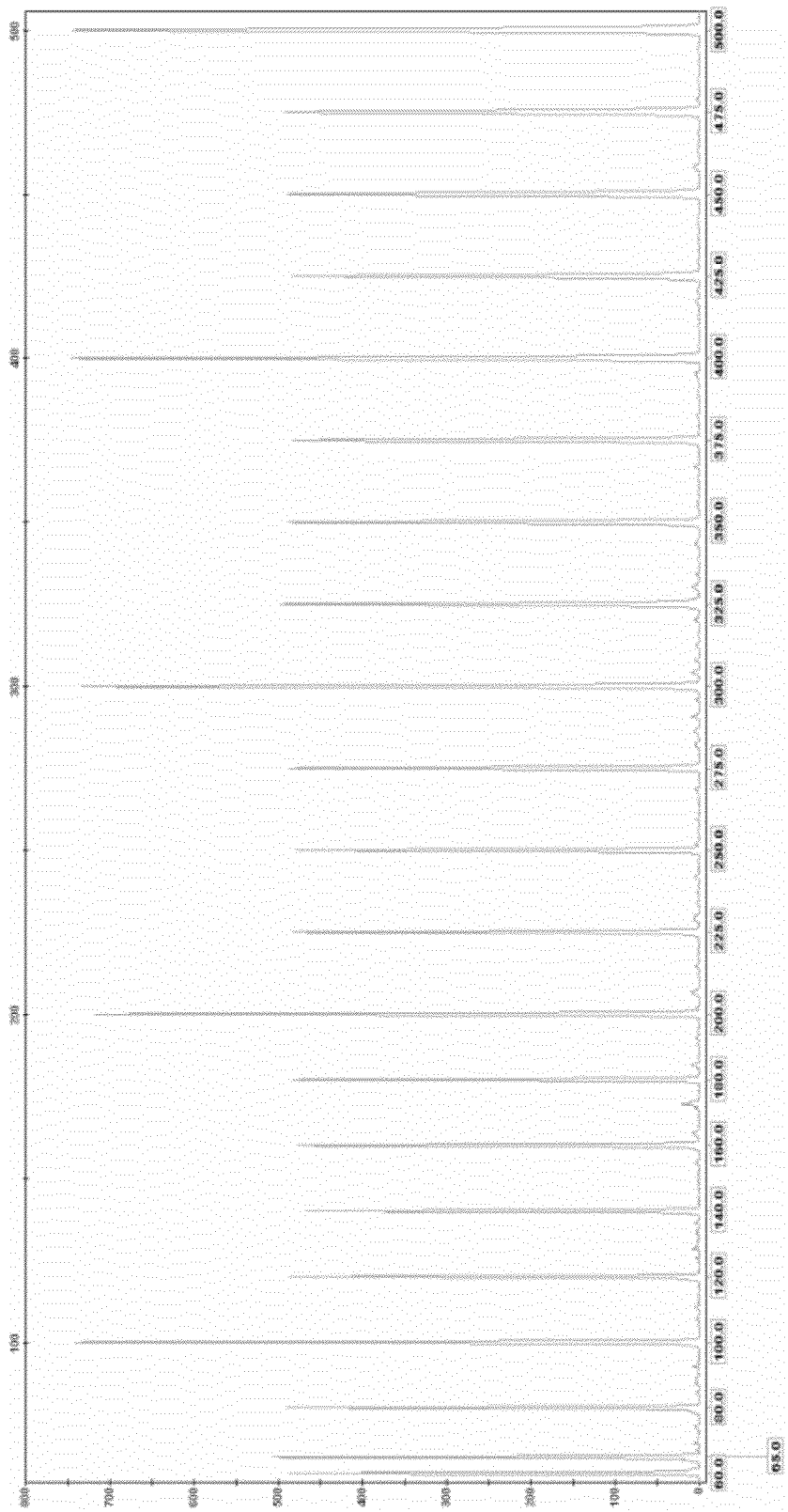
FIG. 4 illustrates an electropherogram showing the CC5 Internal Lane Standard 500 fragments.

Amplified products were combined with HiDi™ Formamide and CC5 Internal Lane Standard 500 (DG1521), and then visualized by capillary electrophoresis on an Applied Biosystems 3130 Genetic Analyzer using 3 Kv, 5 second injection. Analysis was performed using Applied Biosystems' Gene Mapper® ID Software v3.2. Results from the amplification and CC5 Internal Lane Standard 500 are shown in FIGS. 3 and 4, respectively.

Example 12

Labeling Mammalian Cells Expressing HaloTag with Ligand PBI 3847

Figure 5:
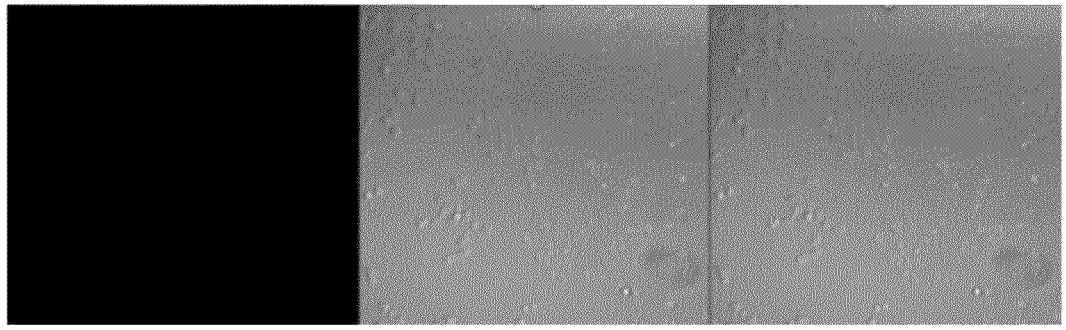
FIG. 5 illustrates HaloTag expressing-cells labeled with PBI 3847.
Figure 5:
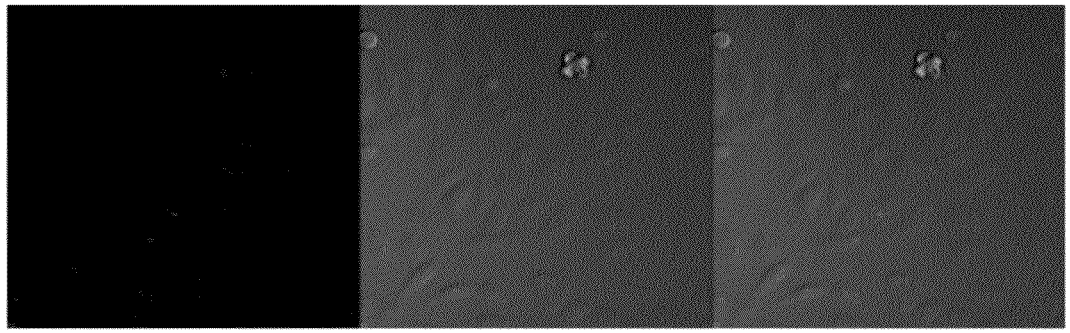
Figure 5:
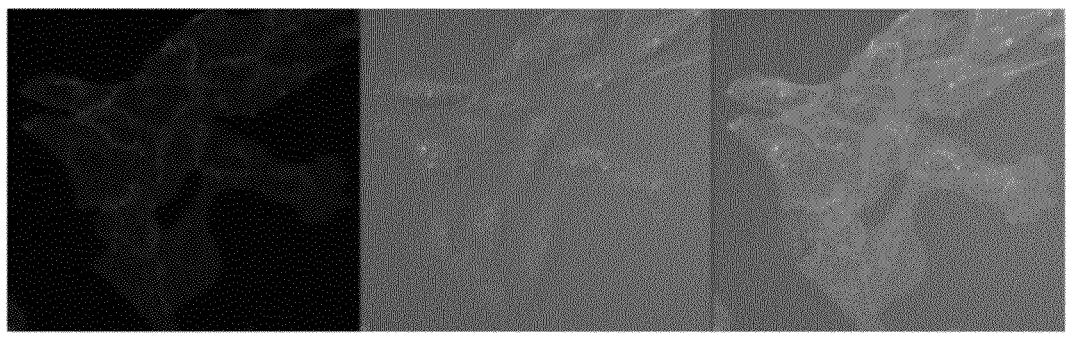

Compound 3847 was first diluted in DMSO to a working concentration of 1 mM and stored at −20° C. One day prior to imaging, untransfected CHO K1 cells, U2OS cells stably expressing either HaloTag-ECS (Extracellular Surface to display HaloTag® on the cell surface) or HaloTag-NLS (Nuclear Localization Sequence for a nuclear HaloTag® protein) were each plated on 8-chambered coverslips and incubated overnight. The following day, ligand PBI 3847 was diluted to 1:200 in warm, complete culture media resulting in a 5× working stock (F12+10% FBS and McCoy's 5A+10% FBS were used for CHO K1 and U2OS cells, respectively). One fifth of cell media was replaced with 5× working stock of ligand PBI 3847 for a final labeling concentration of 1 μM, and cells were incubated for 15 minutes at 37° C. and 5% $CO_2$. Following 15 minutes of labeling, the media containing ligand PBI 3847 was replaced twice with an equal volume of warm, fresh, complete media, and cells then placed at 37° C. and 5% $CO_2$ for 30 minutes to wash out unbound ligand. Following washing, media was replaced with an equal volume of warm, fresh, complete media, and the cells imaged. All imaging was done using an Olympus FV500 confocal microscope equipped with a 37° C. and 5% $CO_2$ environmental chamber, a Red HeNe laser (λ633) and appropriate filter sets. (See FIG. 5).

Example 13

Site-Specific Protein Labeling Using Compound PBI 3956

Site-specific labeling of proteins containing an N-terminal Cysteine (Cys) residue was demonstrated using a fusion protein construct having a HaloTag protein at the amino terminus, a TEV protease cleavage site followed by a cysteine residue, and the coding region for beetle luciferase (Luc). The construct was transfected into *E. coli* cells and then frozen. The frozen, transfected *E. coli* cells were lysed by sonication, and the cell debris removed by centrifugation. The clarified lysates were passed through a HaloLink resin column (Promega) thereby capturing the fusion protein. The resins were washed 50 mM HEPES pH 7.0 and 1M HEPES pH 7.0 buffer containing ProTEV protease (Promega) was applied to the resin columns cleaving the fusion construct at the TEV protease site. The released fusion protein, Cys-Luc, was collected, and the ProTEV protease removed using the Ni-based affinity resin, HisLink™ Protein Purification Resin (Promega). Concentration of the released proteins was determined by a Coomassie protein assay, and SDS PAGE gel analysis was performed on the protein solutions. The solutions were found to contain essentially one protein, Cys-Luc. Following purification and analysis, 10 ul of 2 mM PBI 3956 in DMSO was diluted to 200 ul with water, and 10 ul placed into a reaction tube. A 50 ul sample of Cys-Luc (protein conc. 5.6 mg/ml) and 250 ul of 100 mM HEPES pH 7.5 were mixed, and 20 ul of this solution was added to the reaction tube containing PBI 3956. A 0.5 ml sample of Tris-Glycine SDS Sample Buffer was mixed with 50 ul cystamine (20 mM) and 50 ul of 100 mM 2-mercaptoethanol, and 10 ul of this mixture was added to the reaction tube. The mixture was incubated at room temperature for 90 minutes. Cysteine (20 mM in Tris-Glycine SDS Sample Buffer) was then added to the reaction mixture for 10 minutes to quench any excess cyanobenzothiazole. After this step, the reaction mixture was processed over a Zeba spin column yielding 80 to 90% purified labeled protein.

Any embodiment described herein can be combined with any other suitable embodiment described herein to provide additional embodiments.

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

All references disclosed herein are specifically incorporated by reference in their entirety.

Reference to a "step" in the application is used for convenience purposes only and does not categorize, define or limit the invention as set forth herein.

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A compound of Formula I:

(I)

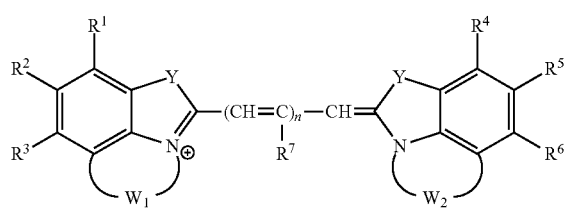

or Formula II:

(II)

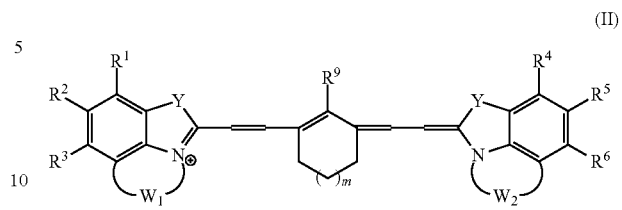

wherein
$R^1$, $R^2$, $R^3$, $R^4$, $R^5$, and $R^6$ are each independently H, alkyl, cycloalkyl, aryl, (aryl)alkyl, heteroaryl, amino, hydroxy, halo, sulfo, or -L-$R^x$; or
two adjacent groups of $R^1$, $R^2$, $R^3$, $R^4$, $R^5$, or $R^6$ taken together with the atoms to which they are attached form a fused benzo ring that is optionally substituted with 1, 2, 3, or 4 alkyl, cycloalkyl, aryl, (aryl)alkyl, heteroaryl, amino, hydroxy, halo, sulfo, or -L-$R^x$ groups;
each $W_1$ and $W_2$ taken together with the atoms to which it is attached is independently a 5-, 6-, 7-, or 8-membered heterocyclic ring, wherein the ring optionally includes a second heteroatom selected from O, S, or N, wherein the N, if present, is substituted by H, alkyl, (aryl)alkyl, or -L-$R^x$, and wherein at least one carbon atom of $W_1$ or $W_2$ is optionally substituted by $R^7$;
each Y is independently $CR^7R^7$, S, O, $CF_2$, or $NR^7$;
each $R^7$ is independently H, ($C_1$-$C_8$)alkyl, aryl, (aryl)alkyl, oxo, or -L-$R^x$;
each L is independently a direct bond or a linker, wherein the linker is a divalent radical of the formula -A-B-Z- wherein A is a direct bond or a ($C_1$-$C_{12}$)alkyl chain optionally comprising one or more unsaturations, optionally substituted by one or more oxo groups, and optionally interrupted by one or more O atoms; B is a direct bond or a —NHC(=O)—, —C(=O)NH—, —OC(=O)—, —C(=O)O—, —O—, or —N($R^8$)— group; and Z is a direct bond or a ($C_1$-$C_{20}$)alkyl chain optionally comprising one or more unsaturations, optionally substituted by one or more oxo groups, and optionally interrupted by one or more O atoms;
each $R^8$ is independently H, ($C_1$-$C_6$)alkyl, or a nitrogen protecting group;
$R^9$ is -L-$R^x$, —O-Ph-$R^x$, —O-Ph-L-$R^x$;
each $R^x$ is independently an activated ester of a carboxylic acid, a maleimide, an amine, an alcohol, a sulfonyl halide, a mercaptan, a boronate, a phosphoramidite, an isocyanate, a haloacetamide, an aldehyde, an azide, an acyl nitrile, a photoactivatable group, a 4-cyanobenzothiazole, a ($C_1$-$C_8$)alkylhalide, or a sulfo group;
provided that at least one -L-$R^x$ group is present and provided that at least one $R^x$ is not a sulfo group;
wherein any alkyl, cycloalkyl, aryl, (aryl)alkyl, or heteroaryl is optionally substituted with one, two, or three halo, hydroxy, or sulfo groups;
m is 0 or 1;
n is 0, 1, or 2; and
an organic or inorganic anion, present when the compound of Formula I or II is cationic.

2. The compound of claim 1 wherein $R^x$ is: an activated ester of a carboxylic acid that includes a —C(=O)O— group covalently bonded to a succinimidyl, a sulfosuccinimidyl, a maleimide, or a 1-oxybenzotriazolyl group; —$NH_2$; —OH; —$SO_2Cl$; —$SO_2Br$; —SH; —B(OH)$_2$; —B(OR)$_2$ wherein R is alkyl or aryl; —O—P(N(alkyl)₂)(O-alkylene-CN); —N=C=O; —C(=O)—Cl; —C(=O)—Br; —C(=O)—I; —C(=O)H; —N₃; —C(=O)CN; a maleimide group; a diazirinyl group; an azidoaryl group; a psoralen derivative; a benzophenone; a 6'-O-linked-4-cyanobenzothiazole; a ($C_1$-$C_7$)alkyl-methylene chloride; a ($C_1$-$C_7$)alkyl-methylene bromide; a ($C_1$-$C_7$)alkyl-methylene iodide; —CO₂H; a ($C_1$-$C_7$) alkyl-methylene iodide; or SO₃H.

3. The compound of claim 1 wherein $R^1$, $R^2$, $R^3$, $R^4$, $R^5$, and $R^6$ are each independently H, F, or sulfo.

4. The compound of claim 1 wherein $W_1$ forms a 6-membered ring having a —CH₂—, —O—, —S—, or —NH— para to the N of the $W_1$ ring in Formula I or II.

5. The compound of claim 1 wherein $W_2$ forms a 6-membered ring having a —CH₂—, —O—, —S—, or —NH— para to the N of the $W_2$ ring in Formula I or II.

6. The compound of claim 1 wherein $W_1$, $W_2$, or both, are substituted on a carbon of the ring with —(CH₂)$_m$—OH, where m is 1 to about 12.

7. The compound of claim 1 wherein each Y is $CR^7R^7$, one $R_7$ of Y is methyl, and the other $R^7$ of Y is -L-$R^x$.

8. The compound of claim 1 wherein at least one L is ($C_1$-$C_{12}$)alkyl or ($C_1$-$C_{12}$)alkyl-B—(CH₂CH₂O)$_n$(CH₂)$_m$— wherein n is 1-6, m is 1-8, and B is —NHC(=O)—, —C(=O)NH—, —OC(=O)—, —C(=O)O—, —O—, —NH—, or a direct bond.

9. The compound of claim 8 wherein at least one L is ($C_1$-$C_{10}$)alkyl or ($C_1$-$C_{12}$)alkyl-C(=O)NH—(CH₂CH₂O)n (CH₂)m- wherein n is 1-6 and m is 1-8.

10. The compound of claim 1 wherein $R^9$ of Formula II is —OPh-NH—($C_1$-$C_{12}$)alkyl-$R^x$, or —OPh-C(=O)NH—(CH₂CH₂O)$_n$(CH₂)$_m$—$R^x$, wherein n is 1-6, m is 1-8.

11. The compound of claim 1 wherein m of Formula II is 1.

12. The compound of claim 1 wherein n of Formula I is 1 or 2.

13. The compound of claim 1 wherein two, three, or four -L-$R^x$ group are present.

14. The compound of claim 1 wherein the inorganic anion is a halo anion.

15. A compound selected from the group consisting of
5-((1E,3E,5E)-5-(1,1-dimethyl-5,6-dihydro-1H-pyrrolo[3,2,1-ij]quinolin-2(4H)-ylidene)penta-1,3-dienyl)-6-(6-(2,5-dioxopyrrolidin-1-yloxy)-6-oxohexyl)-6-methyl-1,2,3,6-tetrahydropyrrolo[3,2,1-ij]quinolinium trifluoroacetate (3525);
6-(6-((2-Cyanoethoxy)(diisopropylamino)phosphinooxy)hexyl)-5-((1E,3E,5E)-5-(1,1-dimethyl-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium chloride (3742);
(E)-2-((2E,4E)-5-(6-(6-(2,5-Dioxopyrrolidin-1-yloxy)-6-oxohexyl)-6-methyl-7-sulfo-1,2,3,6-tetrahydropyrrolo[3,2,1-ij]quinolinium-5-yl)penta-2,4-dienylidene)-1,1-dimethyl-2,4,5,6-tetrahydro-1H-pyrrolo[3,2,1-ij]quinoline-9-sulfonate (3526);
6-(25-chloro-6-oxo-10,13,16,19-tetraoxa-7-azapentacosyl)-5-((1E,3E,5E)-5-(1,1-dimethyl-9-sulfo-5,6-dihydro-1H-pyrrolo[3,2,1-ij]quinolin-2(4H)-ylidene)penta-1,3-dienyl)-6-methyl-1,2,3,6-tetrahydropyrrolo[3,2,1-ij]quinolinium-7-sulfonate (3665);
5-((1E,3E)-3-((E)-2-(1,1-Dimethyl-5,6-dihydro-1H-pyrrolo[3,2,1-ij]quinolin-2(4H)-ylidene)ethylidene)-6-hydroxyhex-1-enyl)-6,6-dimethyl-1,2,3,6-tetrahydropyrrolo[3,2,1-ij]quinolinium chloride (3688);
(E)-2-((E)-3-((E)-2-(6,6-Dimethyl-7-sulfo-1,2,3,6-tetrahydropyrrolo[3,2,1-ij]quinolinium-5-yl)vinyl)-6-hydroxyhex-2-enylidene)-1,1-dimethyl-2,4,5,6-tetrahydro-1H-pyrrolo[3,2,1-ij]quinoline-9-sulfonate (3786);
5-((1E,3E)-3-(1,1-Dimethyl-5,6-dihydro-1H-pyrrolo[3,2,1-ij]quinolin-2(4H)-ylidene)prop-1-enyl)-6-(6-hydroxyhexyl)-6-methyl-1,2,3,6-tetrahydropyrrolo[3,2,1-ij]quinolinium chloride (3785);
Sodium 2-((1E,3Z)-3-(1-(5-carboxypentyl)-1-methyl-9-sulfonato-5,6-dihydro-1H-pyrrolo[3,2,1-ij]quinolin-2(4H)-ylidene)prop-1-enyl)-1-methyl-1-(4-sulfonatobutyl)-1,4,5,6-tetrahydropyrrolo[3,2,1-ij]quinolinium-9-sulfonate (3845);
Sodium 2-((1E,3Z)-3-(1-(6-(2-(2-(6-chlorohexyloxy)ethoxy)ethylamino)-6-oxohexyl)-1-methyl-9-sulfonato-5,6-dihydro-1H-pyrrolo[3,2,1-ij]quinolin-2(4H)-ylidene)prop-1-enyl)-1-methyl-1-(4-sulfonatobutyl)-1,4,5,6-tetrahydropyrrolo[3,2,1-ij]quinolinium-9-sulfonate (3838);
6-((Z)-5-((2E,4E)-5-(6,6-Dimethyl-1,2,3,6-tetrahydrobenzo[f]pyrrolo[3,2,1-ij]quinolinium-5-yl)penta-2,4-dienylidene)-6-methyl-2,3,5,6-tetrahydro-1H-benzo[f]pyrrolo[3,2,1-ij]quinolin-6-yl)hexanoate (3846);
Sodium 2-((1E,3E,5Z)-5-(1-(6-(2-(2-(6-chlorohexyloxy)ethoxy)ethylamino)-6-oxohexyl)-1-methyl-9-sulfonato-5,6-dihydro-1H-pyrrolo[3,2,1-ij]quinolin-2(4H)-ylidene)penta-1,3-dienyl)-1-methyl-1-(4-sulfonatobutyl)-1,4,5,6-tetrahydropyrrolo[3,2,1-ij]quinolinium-9-sulfonate (3847);
Sodium 5-((1E,3E,5Z)-5-(1-(5-carboxypentyl)-1-methyl-9-sulfonato-5,6-dihydro-1H-pyrrolo[3,2,1-ij]quinolin-2(4H)-ylidene)penta-1,3-dienyl)-6-methyl-6-(4-sulfonatobutyl)-1,2,3,6-tetrahydropyrrolo[3,2,1-ij]quinolinium-7-sulfonate (3848);
Sodium 5-((E)-2-((E)-2-(4-carboxyphenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl)vinyl)-6-methyl-6-(4-sulfonatobutyl)-1,2,3,6-tetrahydropyrrolo[3,2,1-ij]quinolinium-7-sulfonate (3855);
Sodium 2-((E)-2-((E)-2-(4-(2-(2-(6-chlorohexyloxy)ethoxy)ethylcarbamoyl)phenoxy)-3-((E)-2-(1-methyl-9-sulfonato-1-(4-sulfonatobutyl)-5,6-dihydro-1H-pyrrolo[3,2,1-ij]quinolin-2(4H)-ylidene)ethylidene)cyclohex-1-enyl)vinyl)-1-methyl-1-(4-sulfonatobutyl)-1,4,5,6-tetrahydropyrrolo[3,2,1-ij]quinolinium-9-sulfonate (3856); or
5-((E)-2-((E)-3-((Z)-2-(1-(25-Chloro-6-oxo-10,13,16,19-tetraoxa-7-azapentacosyl)-1-methyl-9-sulfo-5,6-dihydro-1H-pyrrolo[3,2,1-ij]quinolin-2(4H)-ylidene)ethylidene)-2-(4-sulfophenoxy)cyclohex-1-enyl)vinyl)-6-methyl-6-(4-sulfobutyl)-1,2,3,6-tetrahydropyrrolo[3,2,1-ij]quinolinium-7-sulfonate (3921).

16. A method to detect a selected molecule in a sample, comprising:
a) contacting a sample suspected of having a selected molecule with a composition comprising a conjugate comprising a compound of claim 1 and a ligand for the selected molecule so as to yield a mixture; and
b) detecting the presence or amount of the compound in the mixture.

17. The method of claim 16 wherein the conjugate comprises a compound of claim 1 wherein -L-$R^x$ is -linker-A-X, wherein the linker is a multiatom straight or branched carbon chain that optionally includes one or more N, S, or O atoms; wherein -A-X is a substrate for a dehalogenase, and X is a halogen.

18. The method of claim 16 wherein the ligand is an oligonucleotide.

19. The method of claim 16 wherein the ligand is a cyanobenzothiazole moiety.

20. The method of claim 16 wherein the cyanobenzothiazole moiety is a cyanobenzothiazole moiety of formula (VIII):

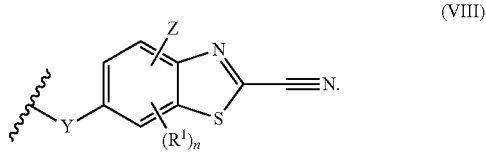

(VIII)

wherein Z is H, F, Cl, Br, I, CN, amino, alkylamino, dialkylamino, alkyl ester, carboxy, carboxylic acid salt, alkyl amide, phosphate, alkyl phosphonate, sulfate, alkyl sulfonate, nitro, or $(C_1-C_{10})$alkyl optionally unsaturated and optionally substituted with amino, hydroxy, oxo (=O), nitro, thiol, or halo;

wherein each $R^1$ is independently H, F, Cl, Br, I, CN, $(C_1-C_6)$alkyl, $(C_1-C_6)$alkoxy, or $(C_1-C_6)$alkylthio, wherein each alkyl, alkoxy, or alkylthio is optionally substituted with F, Cl, Br, I, amino, alkenyl, alkynyl, cycloalkyl, aryl, alkyl sulfonate, or $CO_2M$ wherein M is H, an organic cation, or an inorganic cation; wherein n is 0, 1, or 2; and wherein Y is a linking group comprising $(C_1-C_{16})$alkyl optionally substituted with one or more halo, hydroxy, oxo, $(C_1-C_6)$alkyl, or $(C_1-C_6)$alkoxy, and optionally interrupted with one or more $N(R^1)$, O, S, or —N—C (=O)— groups, or Y can be absent.

21. A kit comprising a conjugate comprising a dye conjugate used to label a molecule in a sample comprising a compound of claim 1 and a ligand for the molecule.

* * * * *